United States Patent
Frigault et al.

(10) Patent No.: US 10,800,840 B2
(45) Date of Patent: Oct. 13, 2020

(54) COMPOSITIONS AND METHODS FOR GENERATING A PERSISTING POPULATION OF T CELLS USEFUL FOR THE TREATMENT OF CANCER

(71) Applicant: THE TRUSTEES OF THE UNIVERSITY OF PENNSYLVANIA, Philadelphia, PA (US)

(72) Inventors: Matthew J. Frigault, Philadelphia, PA (US); Yangbing Zhao, Cherry Hill, NJ (US); John Scholler, Narberth, PA (US); Carl H. June, Merion Station, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 16/014,804

(22) Filed: Jun. 21, 2018

(65) Prior Publication Data

US 2018/0371068 A1    Dec. 27, 2018

Related U.S. Application Data

(63) Continuation of application No. 14/375,015, filed as application No. PCT/US2013/027337 on Feb. 22, 2013, now Pat. No. 10,040,846.

(60) Provisional application No. 61/601,890, filed on Feb. 22, 2012.

(51) Int. Cl.
| | |
|---|---|
| *C07K 16/18* | (2006.01) |
| *C12N 5/0783* | (2010.01) |
| *C07K 16/30* | (2006.01) |
| *C12N 15/86* | (2006.01) |
| *C07K 14/725* | (2006.01) |
| *C07K 14/705* | (2006.01) |

(52) U.S. Cl.
CPC .......... *C07K 16/18* (2013.01); *C07K 14/7051* (2013.01); *C07K 14/70521* (2013.01); *C07K 16/30* (2013.01); *C12N 5/0636* (2013.01); *C12N 15/86* (2013.01); *C07K 2319/33* (2013.01); *C12N 2510/00* (2013.01); *C12N 2740/15041* (2013.01); *C12N 2840/00* (2013.01)

(58) Field of Classification Search
CPC .... C07K 16/18; C07K 16/30; C07K 14/7051; C07K 14/70521; C12N 15/86; C12N 6/0636; C12N 2840/00; C12N 2740/15041; C12N 2319/33; C12N 2510/00
USPC ....... 424/93.21, 93.7, 134.1, 138.1; 435/456, 435/372.3
See application file for complete search history.

(56) References Cited

U.S. PATENT DOCUMENTS

| | | |
|---|---|---|
| 5,143,854 A | 9/1992 | Pirrung et al. |
| 5,350,674 A | 9/1994 | Boenisch et al. |
| 5,384,261 A | 1/1995 | Winkler et al. |
| 5,399,346 A | 3/1995 | Anderson et al. |
| 5,424,186 A | 6/1995 | Fodor et al. |
| 5,445,934 A | 8/1995 | Fodor et al. |
| 5,580,859 A | 12/1996 | Felgner et al. |
| 5,585,362 A | 12/1996 | Wilson et al. |
| 5,589,466 A | 12/1996 | Felgner et al. |
| 5,677,195 A | 10/1997 | Winkler et al. |
| 5,708,153 A | 1/1998 | Dower et al. |
| 5,744,305 A | 4/1998 | Fodor et al. |
| 5,770,358 A | 6/1998 | Dower et al. |
| 5,789,162 A | 8/1998 | Dower et al. |
| 5,800,992 A | 9/1998 | Fodor et al. |
| 5,856,174 A | 1/1999 | Lipshutz et al. |
| 5,858,358 A | 1/1999 | June et al. |
| 5,883,223 A | 3/1999 | Gray |
| 5,922,591 A | 7/1999 | Anderson et al. |
| 6,040,193 A | 3/2000 | Winkler et al. |
| 6,326,193 B1 | 12/2001 | Liu et al. |
| 6,352,694 B1 | 3/2002 | June et al. |
| 6,534,055 B1 | 3/2003 | June et al. |
| 6,692,964 B1 | 2/2004 | June et al. |
| 6,797,514 B2 | 9/2004 | Berenson et al. |
| 6,867,041 B2 | 3/2005 | Berenson et al. |
| 6,887,466 B2 | 5/2005 | June et al. |
| 6,905,680 B2 | 6/2005 | June et al. |
| 6,905,681 B1 | 6/2005 | June et al. |
| 6,905,874 B2 | 6/2005 | Berenson et al. |
| 7,067,318 B2 | 6/2006 | June et al. |
| 7,144,575 B2 | 12/2006 | June et al. |
| 7,172,869 B2 | 2/2007 | June et al. |
| 7,175,843 B2 | 2/2007 | June et al. |

(Continued)

FOREIGN PATENT DOCUMENTS

| | | |
|---|---|---|
| CN | 1726047 A | 1/2006 |
| CN | 101400785 A | 4/2009 |

(Continued)

OTHER PUBLICATIONS

Ang et al. (2009) Mol. Ther. vol. 17(Supp. 1), pp. S25-S26.*
Shirasu et al. (2010) Anticanc. Res., vol. 30, 2731-2738.*
Chinese Patent Application No. 201380010725.2 Notification of First Office Action and Search Report dated Oct. 27, 2015—English translation.

(Continued)

*Primary Examiner* — Anne Marie S Wehbe
(74) *Attorney, Agent, or Firm* — Saul Ewing Arnstein & Lehr LLP; Kathryn Doyle

(57) ABSTRACT

The present invention provides compositions and methods for generating a genetically modified T cells comprising a chimeric antigen receptor (CAR) having an antigen binding domain, a transmembrane domain, a costimulatory signaling region, and a CD3 zeta signaling domain, wherein the T cell exhibits prolonged exponential expansion in culture that is ligand independent and independent of the addition of exogenous cytokines or feeder cells.

14 Claims, 20 Drawing Sheets

Specification includes a Sequence Listing.

(56) References Cited

U.S. PATENT DOCUMENTS

| | | | |
|---|---|---|---|
| 7,232,566 B2 | 6/2007 | June et al. | |
| 7,354,762 B2 * | 4/2008 | Jensen | C07H 21/04 424/134.1 |
| 9,714,278 B2 | 7/2017 | June et al. | |
| 10,040,806 B2 * | 8/2018 | Rajan | A01N 55/08 |
| 2004/0101519 A1 | 5/2004 | June et al. | |
| 2006/0034810 A1 | 2/2006 | Riley et al. | |
| 2006/0121005 A1 | 6/2006 | Berenson et al. | |
| 2009/0202547 A1 | 8/2009 | Yayon et al. | |
| 2010/0068192 A1 | 3/2010 | Enoki et al. | |
| 2013/0287748 A1 * | 10/2013 | June | A61P 37/02 424/93.21 |
| 2014/0099340 A1 | 4/2014 | June et al. | |
| 2014/0271635 A1 | 9/2014 | Brogdon et al. | |
| 2014/0322212 A1 | 10/2014 | Brogdon et al. | |
| 2014/0322275 A1 | 10/2014 | Brogdon et al. | |
| 2015/0017141 A1 | 1/2015 | June et al. | |
| 2015/0038684 A1 * | 2/2015 | Jensen | C07K 14/71 530/391.9 |

FOREIGN PATENT DOCUMENTS

| | | |
|---|---|---|
| CN | 101842490 A | 9/2010 |
| WO | 9954440 A1 | 10/1999 |
| WO | 0129058 A1 | 4/2001 |
| WO | 0196584 A2 | 12/2001 |
| WO | 2004052396 A1 | 6/2004 |
| WO | 2009026723 A1 | 3/2009 |
| WO | 2009091826 A9 | 9/2009 |
| WO | 2010025177 A1 | 3/2010 |
| WO | 2011056894 A2 | 5/2011 |
| WO | 2013040557 A2 | 3/2013 |
| WO | 2013074916 A1 | 5/2013 |
| WO | 2013123061 A1 | 8/2013 |

OTHER PUBLICATIONS

Chinese Patent Application No. 2013800107252—Second Office Action dated Jun. 12, 2016.
Eurasian Patent Application No. 201491572/28 Office Action dated Dec. 15, 2015—English translation.
European Patent Application No. 13751162.2—Extended European Search Report dated Apr. 1, 2016.
European Patent Application No. 13751162.2 Partial European Search Report dated Dec. 2, 2015.
International application No. PCT/US13/27337—International Search Report dated Jun. 19, 2013.
Mexican Patent Application No. MX/a/2014/010583—Office Action dated Mar. 7, 2018.
Singapore Patent Application No. 11201404285V—Notice of Eligibility for Grant and Examination Report dated Mar. 29, 2016.
Adlersberg, et al., The Immunoglobulin Hinge (Interdomain) Region, La Ricerca Clin Lab 1976; 6:191-205.
Alvarez-Vallina, et al., Antigen-specific targetingof CD28-mediated T cell co-stimulation using chimeric single-chain antibody variable fragment-CD28 receptors., 1996, Eur J Immunol 26:2304-2309 (Abstract).
Ang, et al., Conditional Activation of T Cells to Specifically Target c-Met under Hypoxia, 2009, Mol Ther 17: Supp 1: S25-S26.
Arakawa, et al., Targeting of T Cells to CEA-expressing Tumor Cells by Chimeric Immune Receptors with a Highly Specific Single-chain Anti-CEA Activity, 2002, Anticancer Research 22:4285-4289.
Berge, et al., Selective Expansion of a Peripheral Blood CD8+ Memory T Cell Subset Expressing Both Granzyme B and L-Selectin During Primary Viral Infection in Renal Allograft Recipients., Transplant Proc. 30(8):3975-3977, 1998.
Bierer, et al., Cyclosporin A and FK506: molecular mechanisms of immunosuppression and probes for transplantation biology., Curr. Opin. Immun. 5:763-773, 1993.
Bonini, et al., Genetic Modification of T Cells, 2011, Biol Blood Marrow Transplant 17(1 Suppl):S15-20.
Brentjens, et al., Genetically Targeted T Cells Eradicate Systemic Acute Lymphoblastic Leukemia Xenografts, 2007, Clin Cancer Res 13:5426-5435.
Brentjens, et al., Safety and persistence of adoptively transferred autologous CD19-targeted T cells in patients with relapsed or chemotherapy refractory B-cell leukemias., 2011, Blood 118:4817-4828.
Bridgeman, et al., The optimal antigen response of chimeric antigen receptors harboring the CD3zeta transmembrane domain is dependent upon incorporation of the receptor into the endogenous TCR/CD3 complex, J Immunol, 2010, 184(12):6938-49.
Carpenito, et al., Control of large, established tumor xenografts with genetically retargeted human T cells containing CD28 and CD137 domains, 2009, PNAS 106(9):3360-3365.
Cooper, et al., Innovative T Cell-Targeted Therapy for Ovarian Cancer, Annual Report for Grant W81XWH-11-1-0459, 2012.
Crisanti, et al., The HDAC inhibitor panobinostat (LBH589) inhibits mesothelioma and lung cancer cells in vitro and in vivo with particular efficacy for small cell lung cancer., 2009, Mol Cancer Ther 8:2221-2231.
Curran, et al., Chimeric antigen receptors for T cell immunotherapy: current understanding and future directions., J Gene Med 14(6):405-415 (2012).
Ertl, et al., Considerations for the Clinical Application of Chimeric Antigen Receptor T Cells: Observations from a Recombinant DNA Advisory Committee Symposium Held Jun. 15, 2010., 2011, Cancer Res 71:3175-3181.
Feldhaus, et al., A CD2/CD28 chimeric receptor triggers the CD28 signaling pathway in CTLL.2 cells, 1997, Gene Ther 4:833-838.
Finney, et al., Activation of Resting Human Primary T Cells with Chimeric Receptors: Costimulation from CD28, Inducible Costimulator, CD134, and CD137 in Series with Signals from the TCR-zeta Chain, 2004, J Immunol 172:104-113.
Finney, et al., Chimeric Receptors Providing Both Primary and Costimulatory Signaling in T Cells from a Single Gene Product, 1998, Journal of Immunology 161:2791-2797.
Fodor, et al., Light-directed, spatially addressable parallel chemical synthesis., 1991, Science, 251:767-777 (Abstract).
Friedmann-Morvinski, et al., Redirected primary T cells harboring a chimeric receptor require costimulation for their antigen-specific activation., 2005, Blood 105:3087-3093.
Garland, et al., The use of Teflon cell culture bags to expand functionally active CD8+ cytotoxic T lymphocytes., J. Immunol Meth. 227(1-2):53-63, 1999.
Geiger, et al., Integrated src kinase and costimulatory activity enhances signal transduction through single-chain chimeric receptors in T lymphocytes., 2001, Blood 98:2364-2371.
Good, et al., Constitute Dephosphorylation and Activation of a Member of the Nuclear Factor of Activated T Cells, NF-AT1, in Tax-expressing and Type I Human T-cell Leukemia Virus-infected Human T Cells., 1997, J Biol Chem 272 (3):1425-1428.
Goronzy, et al., Signaling pathways in aged T cells—a reflection of T cell differentiation, cell senescence and host environment., 2012, Semin Immunol 24(5):365-72.
Guedan, et al., European Society of Gene and Cell Therapy French Society of Cell and Gene Therapy Collaborative Congress, 23(10): A1-A173 (2012).
Gyobu, et al., Generation and Targeting of Human Tumor-Specific Tc1 and Th1 Cells Transduced with a Lentivirus Containing a Chimeric Immunoglobulin T-Cell Receptor., 2004, Cancer Res 64:1490-1495.
Haanen, et al., Selective Expansion of Cross-reacitve CD8+ Memory T Cells by Viral Variants., J. Exp. Med. 190 (9):13191328, 1999.
Haynes, et al., Rejection of Syngeneic Colon Carcinoma by CTLs Expressing Single-Chain Antibody Receptors Codelivering CD28 Costimulation., J Immunol 2002; 169:5780-5786.
Heemskerk, et al., Adoptive Cell Therapy for Patients with Melanoma, Using Tumor-Infiltrating Lymphocytes Genetically Engineered to Secrete Interleukin-2, 2008, Human Gene Therapy 19:496-510.

(56) References Cited

OTHER PUBLICATIONS

Henderson, et al., Comparison of the effects of FK-506, cyclosporin A and rapamycin on IL-2 production., Immun. 73:316-321, 1991.
Hombach, et al., Tumor-Specific T Cell Activation by Recombinant Immunoreceptors: CD3☐zeta Signaling and CD28 Costimulation Are Simultaneously Required for Efficient IL-2 Secretion and Can Be Integrated Into One Combined CD28/CD3-zeta Signaling Receptor Molecule, J Immunol, 2004, 173(1):695.
Hsu, et al., Cytokine-independent growth and clonal expansion of a primary human CD8+ T-cell clone following retroviral transduction with the IL-15 gene, 2007, Blood 109:5168-5177.
Huang, et al., Stable gene transfer and expression in human primary T cells by the Sleeping Beauty transposon system., 2006, Blood 107:483-491.
Jena, et al., Redirecting T-cell specificity by introducing a tumor-specific chimeric antigen receptor., 2010, Blood. 116:1035-1044.
Jin, et al., MetMAb, the One-Armed 5D5 Anti-c-Met Antibody, Inhibits Orthotopic Pancreatic Tumor Growth and Improves Survival., Cancer Res 68(11):4360-4368 (2008).
June, et al., T-Cell Proliferation Involving the CD28 Pathway Is Associated with Cyclosporine-Resistant Interleukin 2 Gene Expression., 1987, Mol Cell Biol 7(12):4472-4481.
Kalos, et al., T Cells with Chimeric Antigen Receptors Have Potent Antitumor Effects and Can Establish Memory in Patients with Advanced Leukemia., 2011, Sci Transl Med 3:95ra73.
Kochenderfer, et al., Eradication of B-lineage cells and regression of lymphoma in a patient treated with autologous T cells genetically engineered to recognize CD19., 2010, Blood 116:4099-4102.
Kohn, et al., CARs on Track in the Clinic., 2011, Mol Ther 19:432-438.
Kowolik, et al., CD28 Costimulation Provided through a CD19-Specific Chimeric Antigen Receptor Enhances In vivo Persistence and Antitumor Efficacy of Adoptively Transferred T Cells, 2006, Cancer Res 66:10995-11004.
Krause, et al., Antigen-dependent CD28 Signaling Selectively Enhances Survival and Proliferation in Genetically Modified Activated Human Primary T Lymphocytes., 1998, J Exp Med 188:619-626.
Lal, et al., Targeting the c-Met Pathway Potentiates Glioblastoma Responses to gamma-Radiation., 2005, Clin Cancer Res 11:4479-4486.
Liu, et al., Calcineurin Is a Common Target of Cyclophilin-Cyclosporin A and FKBP-FK506 Complexes., Liu et al., Cell 66:807-815, 1991.
Loskog, et al., Addition of the CD28 signaling domain to chimeric T-cell receptors enhances chimeric T-cell resistance to T regulatory cells, 2006, Leukemia 20:1819-1828.
Lukens, et al., Comparisons of telomere lengths in peripheral blood and cerebellum in Alzheimer's disease, 2009, Alzheimers Dement 5:463-469.
Maher, et al., Human T-lymphocyte cytotoxicity and proliferation directed by a single chimeric TCR-zeta/CD28 receptor., 2002, Nature Biotechnology 20:70-75.
Milone, et al., Chimeric Receptors Containing C137 Signal Transduction Domains Mediate Enhanced Survival of T Cells and Increased Antileukemic Efficacy In Vivo., 2009, Mol Ther 17:1453-1464.
Moeller, et al., A functional role for CD28 costimulation in tumor recognition by single-chain receptor-modified T cells, 2004, Cancer Gene Ther 11:371-379.
Mumtaz, et al., Design of liposomes for circumventing the reticuloendothelial cells., 1991 Glycobiology 5: 505-10.
Newrzela, et al., Retroviral Insertional Mutagenesis Can Contribute to Immortalization of Mature T Lymphocytes, 2011, Mol Med 17:1223-1232.
Nguyen, et al., Identitication of a murine CD28 dileucine motif that suppresses single-chain chimeric T-cell receptor expression and function, 2003, Blood 102(13):4320-5.

Porter, et al., Chimeric Antigen Receptor-Modified T Cells in Chronic Lymphoid Leukemia., 2011, N Engl J Med 365:725-733.
Pule, et al., A Chimeric T Cell Antigen Receptor That Augments Cytokine Release and Supports Clonal Expansion of Primary Human T Cells, 2005, Molecular Therapy 12:933-941.
Restifo, et al., Adoptive immunotherapy for cancer: harnessing the T cell response., 2012, Nat Rev Immunol 12:269-281.
Savolodo, et al., CD28 costimulation improves expansion and persistence of chimeric antigen receptor-modified T cells in lymphoma patients., 2011, J Clin Invest 121:1822-1825.
Shibaguchi, et al., A Fully Human Chimeric Immune Receptor for Retargeting T-cells to CEA-expressing Tumor Cells, 2006, Anticancer Res 26:4067-4072.
Singh, et al., Redirecting Specificity of T-Cell Populations for CD19 Using the Sleeping Beauty System, 2008, Cancer Research 68:2961-2971.
Skibinski, et al., The role of hepatocyte growth factor and its receptor c-met in interactions between lymphocytes and stromal cells in secondary human lymphoid organs, 2001, Immunology 102:506-514.
Tammana, et al., 4-1BB and CD28 Signaling Plays a Synergistic Role in Redirecting Umbilical Cord Blood T Cells Agains B-Cell Malignancies., 2010, Hum Gene Ther 21:75-86.
Teng, et al., Adoptive Transfer of Chimeric Fc-epsilon-RI Gene-Modified Human T Cells for Cancer Immunotherapy., 2006, Human Gene Therapy 17:1134-1143.
Teng, et al., Immunotherapy of Cancer Using Systemically Delivered Gene-Modified Human T Lymphocytes., 2004, Hum Gene Ther 15:699-708.
Till, et al., Adoptive immunotherapy for indolent non-Hodgkin lymphoma and mantle cell lymphoma using genetically modified autologous CD20-specific T cells., 2012, Blood 119:3940-3950.
Ui-Tei, et al., Sensitive assay of RNA interference in *Drosophila* and Chinese hamster cultured cells using firefly luciferase gene as target., 2000 FEBS Letters 479: 79-82.
Voehringer, et al., Lack of proliferative capacity of human effector and memory T cells expressing killer cell lectinlike receptor GI (KLRGI)., 2002, Blood 100:3698-3702.
Westwood, et al., Adoptive transfer of T cells modified with a humanized chimeric receptor gene inhibits growth of Lewis-Y-expressing tumors in mice., 2005, Proc Natl Acad Sci USA 102:19051-19056.
Willemsen, et al., T Cell Retargeting with MHC Class I-Restricted Antibodies: The CD28 Costimulatory Domain Enhances Antigen-Specific Cytotoxicity and Cytokine Production., 2005, J Immunol 174:7853-7858.
Yeh, et al., Regulation of a Late Phase of T Cell Polarity and Effector Functions by Crtam., 2008, Cell 132:846-859.
Yu, et al., The Role of B7 Costimulation in CD4/CD8 T Cell Homeostasis., 2000, J Immunol 164:3543-3553.
Zhao, et al., A Herceptin-Based Chimeric Antigen Receptor with Modified Signaling Domains Leads to Enhanced Survival of Transduced T Lymphocytes and Antitumor Activity., J Immunol 183(9):5563-5574 (2009).
Zhao, et al., High-Efficiency Transfection of Primary Human and Mouse T Lymphocytes Using RNA Electroporation., 2006, Mol Ther 13:151-159.
Zhao, et al., Multiple injections of electroporated autologous T cells expressing a chimeric antigen receptor mediate regression of human disseminated tumor., 2010, Cancer Res 70:9062-9072.
Canadian Patent Application No. 2,863,799—Office Action dated Jan. 15, 2019.
Kochenderfer, et al., Construction and Pre-clinical Evaluation of an Anti-CD19 Chimeric Antigen Receptor, J Immunother 32(7) ,2009 ,689-702.

\* cited by examiner

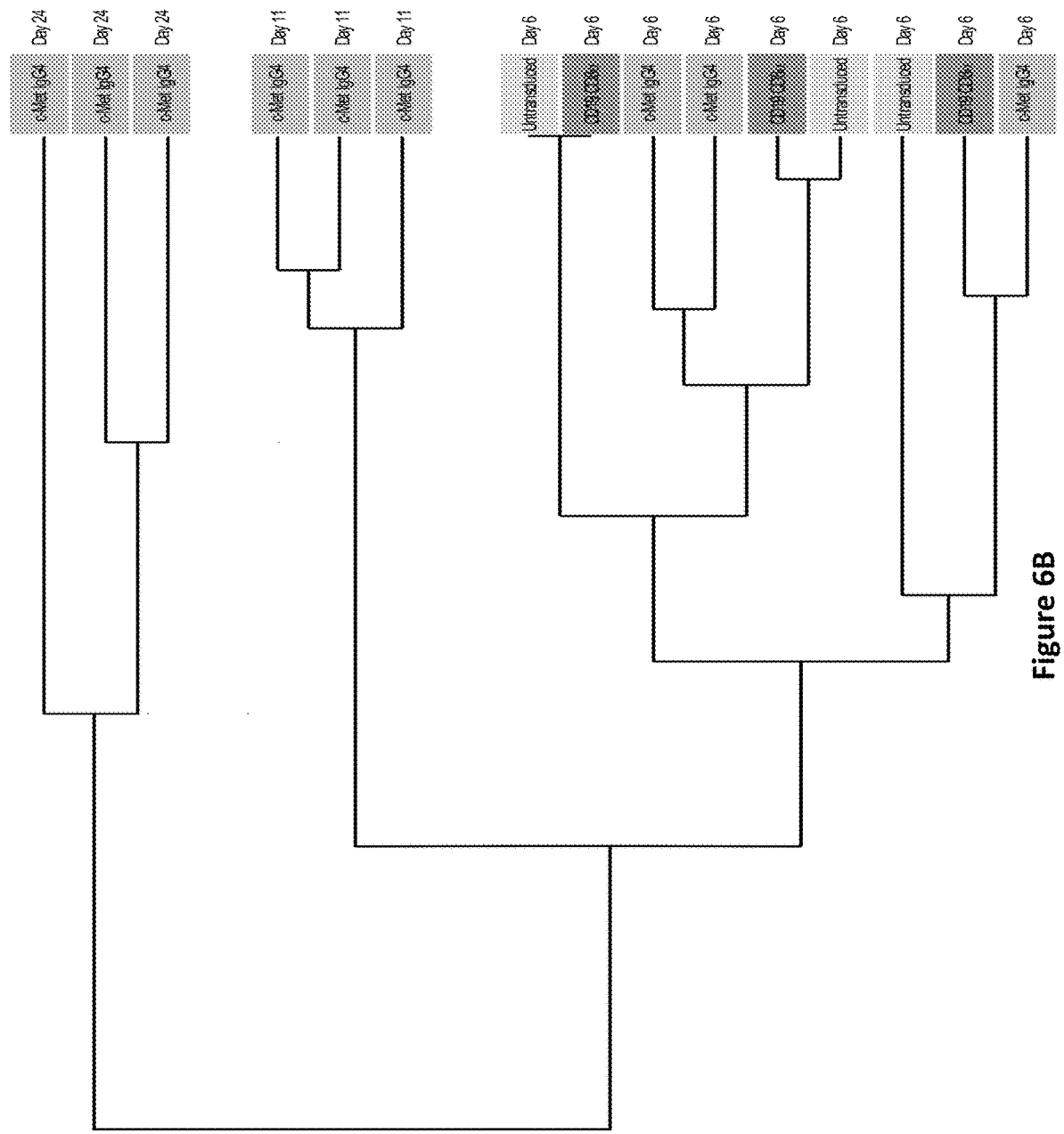

SEQUENCE LISTING

```
<160> NUMBER OF SEQ ID NOS: 3

<210> SEQ ID NO 1
<211> LENGTH: 2025
<212> TYPE: DNA
<213> ORGANISM: Artificial sequence
<220> FEATURE:
<223> OTHER INFORMATION: Chemically synthesized

<400> SEQUENCE: 1
atgctgctgc tggtgaccag cctgctgctg tgtgagctgc cccacccgc ctttctgctg       60 atccccgaca tccagatgac ccagagcccc agcagcgtga gcgccagcgt gggcgaccgg      120
gtgaccatca cctgccgggc cagccagggc atcaacacct ggctggcctg gtatcagcag      180
aagcccggca aggcccccaa gctgctgatc tacgccgcca gcagcctgaa gagcggcgtg      240
cccagccggt ttagcggctc tggctctggc gccgacttca ccctgaccat cagcagcctg      300
cagcccgagg acttcgccac ctactactgc cagcaggcca acagcttccc cctgaccttt      360
ggcggcggaa caaaggtgga gatcaagggc agcacctccg gcagcggcaa gcctggcagc      420
ggcgagggca gcaccaaggg ccaggtgcag ctggtgcaga gcggagccga ggtgaagaag      480
cctggcgcct ccgtcaaggt gtcctgcgag gccagcggct acaccttcac cagctacggc      540
ttcagctggg tgcggcaggc accaggccag ggcctcgaat ggatgggctg gatcagcgcc      600
agcaacggca acacctacta cgcccagaag ctgcagggca gggtcaccat gaccaccgac      660
accagcacca gcagcgccta catggaactg cggagcctga aagcgacga caccgccgtg      720 tactactgcg ccagggtgta cgccgactac gccgattact ggggccaggg cacctggtg      780 accgtgagca gcgagagcaa gtacggccct ccctgccccc cttgccctgc ccccgagttc      840
ctgggcggac ccagcgtgtt cctgttcccc ccaagccca aggacaccct gatgatcagc      900 cggaccccg aggtgacctg tgtggtggtg gacgtgtccc aggaggaccc cgaggtccag      960
ttcaactggt acgtggacgg cgtggaggtg cacaacgcca agaccaagcc ccgggaggag     1020
cagttcaata gcacctaccg ggtggtgtcc gtgctgaccg tgctgcacca ggactggctg     1080
aacggcaagg aatacaagtg taaggtgtcc aacaagggcc tgcccagcag catcgagaaa     1140
accatcagca aggccaaggg ccagcctcgg gagcccagg tgtacaccct gcccctagc     1200 caagaggaga tgaccaagaa ccaggtgtcc ctgacctgcc tggtgaaggg cttctacccc     1260
agcgacatcg ccgtggagtg ggagagcaac ggccagcccg agaacaacta caagaccacc     1320 cccctgtgc tggacagcga cggcagcttc ttcctgtaca gccggctgac cgtggacaag     1380
agccggtggc aggagggcaa cgtctttagc tgctccgtga tgcacgaggc cctgcacaac     1440
```

| | |
|---|---|
| cactacaccc agaagagcct gagcctgtcc ctgggcaaga tgttctgggt gctggtcgtt | 1500 |
| gtgggcggcg tgctggcctg ctacagcctg ctggtgacag tggccttcat catcttttgg | 1560 |
| gtgaggagca agcggagcag actgctgcac agcgactaca tgaacatgac ccccggagg | 1620 |
| cctggcccca cccggaagca ctaccagccc tacgcccctc caggatttt cgccgcctac | 1680 |
| cggagccggg tgaagttcag ccggagcgcc gacgcccctg cctaccagca gggccagaac | 1740 |
| cagctgtaca cgagctgaa cctgggccgg agggaggagt acgacgtgct ggacaagcgg | 1800 |
| agaggccggg accctgagat gggcggcaag ccccggagaa agaaccccca ggagggcctg | 1860 |
| tataacgaac tgcagaaaga caagatggcc gaggcctaca cgagatcgg catgaagggc | 1920 |
| gagcggaggc ggggcaaggg ccacgacggc ctgtaccagg gcctgagcac cgccaccaag | 1980 |
| gatacctacg acgccctgca catgcaggcc ctgcccccca gatga | 2025 |

<210> SEQ ID NO 2
<211> LENGTH: 2028
<212> TYPE: DNA
<213> ORGANISM: Artificial sequence
<220> FEATURE:
<223> OTHER INFORMATION: Chemically synthesized

<400> SEQUENCE: 2

| | |
|---|---|
| atggccttac cagtgaccgc cttgctcctg ccgctggcct tgctgctcca cgccgccagg | 60 |
| ccgggatccc agtacaaact gcagcagtct gggcctgagc tggagaagcc tggcgcttca | 120 |
| gtgaagatat cctgcaaggc ttctggttac tcattcactg ctacaccat gaactgggtg | 180 |
| aagcagagcc atgaaagag ccttgagtgg attggactta ttactcctta caatggtgct | 240 |
| tctagctaca accagaagtt caggggcaag gccacattaa ctgtagacaa gtcatccagc | 300 |
| acagcctaca tggacctcct cagtctgaca tctgaagact ctgcagtcta tttctgtgca | 360 |
| agggggggtt acgacgggag gggttttgac tactggggcc aagggaccac ggtcaccgtc | 420 |
| tcctcaggtg gaggcggttc aggcggcggt ggctctagcg tggtggatc ggacatcgag | 480 |
| ctcactcagt ctccagcaat catgtctgca tctccagggg agaaggtcac catgacctgc | 540 |
| agtgccagct caagtgtaag ttacatgcac tggtaccagc agaagtcagg cacctccccc | 600 |
| aaaagatgga tttatgacac atccaaactg gcttctggag tcccaggtcg cttcagtggc | 660 |
| agtgggtctg gaaactctta ctctctcaca atcagcagcg tggaggctga agatgatgca | 720 |
| acttattact gccagcagtg gagtaagcac cctctcacgt acggtgctgg gacaaagttg | 780 |
| gaaatcaaaa gcagcgagag caagtacggc cctcccgcc cccttgccc tgccccgag | 840 |
| ttcctgggcg gacccagcgt gttcctgttc cccccaagc caaggacac cctgatgatc | 900 |
| agccggaccc ccgaggtgac ctgtgtggtg gtggacgtgt cccaggagga ccccgaggtc | 960 |
| cagttcaact ggtacgtgga cggcgtggag gtgcacaacg ccaagaccaa gccccgggag | 1020 |
| gagcagttca atagcaccta ccgggtggtg tccgtgctga ccgtgctgca ccaggactgg | 1080 |
| ctgaacggca aggaatacaa gtgtaaggtg tccaacaagg gcctgccag cagcatcgag | 1140 |
| aaaaccatca gcaaggccaa gggccagcct cgggagcccc aggtgtacac cctgccccct | 1200 |
| agccaagagg agatgaccaa gaaccaggtg tccctgacct gcctggtgaa gggcttctac | 1260 |
| cccagcgaca tcgccgtgga gtgggagagc aacggccagc ccgagaacaa ctacaagacc | 1320 |
| acccccctg tgctggacag cgacggcagc ttcttcctgt acagccggct gaccgtggac | 1380 |
| aagagccggt ggcaggaggg caacgtcttt agctgctccg tgatgcacga ggccctgcac | 1440 |
| aaccactaca cccagaagag cctgagcctg tccctgggca gatgttctg ggtgctggtc | 1500 |

```
gttgtgggcg gcgtgctggc ctgctacagc ctgctggtga cagtggcctt catcatcttt    1560
tgggtgagga gcaagcggag cagactgctg cacagcgact acatgaacat gacccccgg     1620 aggcctggcc ccacccggaa gcactaccag ccctacgccc ctcccaggga tttcgccgcc    1680
taccggagcc gggtgaagtt cagccggagc gccgacgccc tgcctacca gcagggccag     1740 aaccagctgt acaacgagct gaacctgggc cggagggagg agtacgacgt gctggacaag    1800
cggagaggcc gggaccctga gatgggcggc aagccccgga gaaagaaccc ccaggagggc    1860
ctgtataacg aactgcagaa agacaagatg gccgaggcct acagcgagat cggcatgaag    1920
ggcgagcgga ggcggggcaa gggccacgac ggcctgtacc agggcctgag caccgccacc    1980
aaggatacct acgacgccct gcacatgcag gccctgcccc ccagatga                2028

<210> SEQ ID NO 3
<211> LENGTH: 2028
<212> TYPE: DNA
<213> ORGANISM: Artificial sequence
<220> FEATURE:
<223> OTHER INFORMATION: Chemically synthesized

<400> SEQUENCE: 3
atggccttac cagtgaccgc cttgctcctg ccgctggcct tgctgctcca cgccgccagg      60
ccggacatcc agatgacaca gactacatcc tccctgtctg cctctctggg agacagagtc     120
accatcagtt gcagggcaag tcaggacatt agtaaatatt taaattggta tcagcagaaa     180
ccagatggaa ctgttaaact cctgatctac catacatcaa gattacactc aggagtccca     240
tcaaggttca gtggcagtgg gtctggaaca gattattctc tcaccattag caacctggag     300
caagaagata ttgccactta cttttgccaa cagggtaata cgcttccgta cacgttcgga     360
gggggaccaa gctggagat cacaggtggc ggtggctcgg cggtggtgg gtcgggtggc      420 ggcggatctg aggtgaaact gcaggagtca ggacctggcc tggtggcgcc ctcacagagc     480
ctgtccgtca catgcactgt ctcagggggtc tcattacccg actatggtgt aagctggatt    540
cgccagcctc cacgaaaggg tctggagtgg ctgggagtaa tatgggggtag tgaaaccaca    600 tactataatt cagctctcaa atccagactg accatcatca aggacaactc caagagccaa    660
gttttcttaa aaatgaacag tctgcaaact gatgacacag ccatttacta ctgtgccaaa    720
cattattact acggtggtag ctatgctatg gactactggg gccaaggaac ctcagtcacc    780
gtctcctcaa gcagcgagag caagtacggc cctccctgcc ccccttgccc tgcccccgag    840
ttcctgggcg gacccagcgt gttcctgttc ccccccaagc caaggacac cctgatgatc     900 agccggaccc ccgaggtgac ctgtgtggtg gtggacgtgt cccaggagga ccccgaggtc     960
cagttcaact ggtacgtgga cggcgtggag gtgcacaacg ccaagaccaa gccccgggag   1020
gagcagttca atagcaccta ccgggtggtg tccgtgctga ccgtgctgca ccaggactgg   1080
ctgaacggca aggaatacaa gtgtaaggtg tccaacaagg gcctgcccag cagcatcgag   1140
aaaaccatca gcaaggccaa gggccagcct cgggagcccc aggtgtacac cctgcccccct 1200 agccaagagg agatgaccaa gaaccaggtg tccctgacct gcctggtgaa gggcttctac   1260
cccagcgaca tcgccgtgga gtgggagagc aacggccagc cgagaacaa ctacaagacc    1320 acccccctg tgctggacag cgacggcagc ttcttcctgt acagccggct gaccgtggac    1380
aagagccggt ggcaggaggg caacgtcttt agctgctccg tgatgcacga ggccctgcac   1440
aaccactaca cccagaagag cctgagcctg tccctgggca agatgttctg ggtgctggtc    1500
```

-continued

```
gttgtgggcg gcgtgctggc ctgctacagc ctgctggtga cagtggcctt catcatcttt    1560
tgggtgagga gcaagcggag cagactgctg cacagcgact acatgaacat gacccccgg     1620 aggcctggcc ccaccggaa gcactaccag ccctacgccc ctcccaggga tttcgccgcc     1680
taccggagcc gggtgaagtt cagccggagc gccgacgccc ctgcctacca gcagggccag    1740
aaccagctgt acaacgagct gaacctgggc cggagggagg agtacgacgt gctggacaag    1800
cggagaggcc gggaccctga gatgggcggc aagccccgga gaaagaaccc ccaggagggc    1860
ctgtataacg aactgcagaa agacaagatg gccgaggcct acagcgagat cggcatgaag    1920
ggcgagcgga ggcggggcaa gggccacgac ggcctgtacc agggcctgag caccgccacc    1980
aaggatacct acgacgccct gcacatgcag gccctgcccc ccagatga                2028
```

COMPOSITIONS AND METHODS FOR GENERATING A PERSISTING POPULATION OF T CELLS USEFUL FOR THE TREATMENT OF CANCER

CROSS-REFERENCE TO RELATED APPLICATION

The present application is a continuation of U.S. patent application Ser. No. 14/375,015, filed Jul. 28, 2014, issued as U.S. Pat. No. 10,040,846, which is a 35 U.S.C. § 371 national phase application from, and claims priority to, International Application No. PCT/US2013/027337, filed Feb. 22, 2013, which claims priority to U.S. Provisional Application Ser. No. 61/601,890, filed Feb. 22, 2012, all of which applications are incorporated by reference herein in their entireties.

STATEMENT REGARDING FEDERALLY SPONSORED RESEARCH OR DEVELOPMENT

This invention was made with government support under grant 1R01CA120409 awarded by the National Cancer Institute. The government has certain rights in the invention.

BACKGROUND OF THE INVENTION

The generation of tumor-specific T lymphocytes by genetic modification to express chimeric antigen receptors (CARs) is gaining traction as a form of synthetic biology generating powerful antitumor effects (Jena et al., 2010, Blood. 116:1035-1044; Bonini et al., 2011, Biol Blood Marrow Transplant 17(1 Suppl):S15-20; Restifo et al., 2012, Nat Rev Immunol 12:269-281; Kohn et al., 2011, Mol Ther 19:432-438; Savoldo et al., 2011, J Clin Invest 121:1822-1825; Ertl et al., 2011, Cancer Res 71:3175-3181). Because the specificity is conferred by antibody fragments, the CAR T cells are not MHC restricted and are therefore more practical than approaches based on T cell receptors that require MHC matching.

Clinical data from patients treated with CD19-specific CAR$^+$ T cells indicates that robust in vivo proliferation of the infused T cells is a key requirement for immunoablation of tumors (Porter et al., 2011, N Engl J Med 365:725-733; Kalos et al., 2011, Sci Transl Med 3:95ra73). Therefore, efforts have been made to incorporate the signaling endodomains of co-stimulatory molecules such as CD28, OX40, and 4-1BB into CARs. In 1998 it was first reported that the use of gene-engineered T cells expressing chimeric single-chain (scFv) receptors capable of co-delivering CD28 costimulation and T cell receptor/CD3 zeta chain (CD3ζ) activation signals increased the function and proliferation of CAR T cells (Krause et al, 1998, J Exp Med 188:619-626; Finney et al., 1998, Journal of Immunology 161:2791-2797). A number of laboratories have confirmed that incorporation of CD28 signaling domains enhances the function of CARs in pre-clinical studies compared to CD3ζ or FcεR1 (Geiger et al., 2001, Blood 98:2364-2371; Arakawa et al., 2002, Anticancer Research 4285-4289; Haynes et al., 2002, J Immunol 169(10):5780-6; Maher et al., 2002, Nature Biotechnology 20:70-75; Finney et al, 2004, J Immunol 172:104-113; Gyobu et al., 2004, Cancer Res 64:1490-1495; Moeller et al., 2004, Cancer Gene Ther 11:371-379; Teng et al., 2004, Hum Gene Ther 15:699-708; Friedmann-Morvinski et al., 2005, Blood 105:3087-3093; Pule et al., 2005, Molecular Therapy 12:933-941; Westwood et al., 2005, Proc Natl Acad Sci USA 102:19051-19056; Willemsen et al., 2005, J Immunol 174:7853-7858; Kowolik et al, 2006, Cancer Res 66:10995-11004; Loskog et al., 2006, Leukemia 20:1819-1828; Shibaguchi et al., 2006, Anticancer Res 26:4067-4072; Brentjens et al., 2007, Clin Cancer Res 13:5426-5435; Teng et al., 2006, Human Gene Therapy 17:1134-1143). In a study in patients with B-cell malignancies, CD28:CD3ζ CARs had improved survival compared to CARs endowed only with the CD3ζ signaling domain (Savoldo et al., 2011, J Clin Invest 121:1822-1825).

However, there is still a need in the art to better improve construction of CARs that permit extensive T-cell proliferation. The present invention satisfies this need in the art.

SUMMARY OF THE INVENTION

The present invention provides an isolated nucleic acid sequence encoding a chimeric antigen receptor (CAR), wherein the CAR comprises an antigen binding domain, a hinge domain, a transmembrane domain, a costimulatory signaling region, and a CD3 zeta signaling domain, and further wherein when the CAR is transduced into a T cell, the CAR contributes to at least one of: increased antigen-independent activation of the transduced T cell, increased mean cell volume (MCV) of the transduced T cell, increased cell population expansion of the transduced T cell, increased proliferation of the transduced T cell, increased numbers of progeny of the transduced T cell, increased effector cytokine secretion, sustained expression of granzyme, increased persistence of the transduced T cell population in vitro, or increased persistence of the transduced T cell population in vivo.

In one embodiment, the hinge domain is an IgG4 hinge domain.

In one embodiment, the antigen binding domain is an anti-cMet binding domain, the hinge domain is IgG4, the transmembrane domain is a CD28 transmembrane domain, and the costimulatory signaling region is a CD28 signaling region. In one embodiment, the CAR comprises the amino acid sequence of SEQ ID NO: 1.

In one embodiment, the antigen binding domain is an anti-mesothelin binding domain, the hinge domain is an IgG4 hinge domain, the transmembrane domain is a CD28 transmembrane domain, and the costimulatory signaling region is a CD28 signaling region. In one embodiment, the CAR comprises the amino acid sequence of SEQ ID NO: 2.

In one embodiment, the antigen binding domain is an anti-CD19 binding domain, the hinge domain is an IgG4 hinge domain, the transmembrane domain is an CD28 transmembrane domain, and the costimulatory signaling region is a CD28 signaling region. In one embodiment, the CAR comprises the amino acid sequence of SEQ ID NO: 3.

In one embodiment, the antigen binding domain is an antibody or an antigen-binding fragment thereof.

The invention also provides a T cell comprising a nucleic acid sequence encoding a chimeric antigen receptor (CAR), the CAR comprising an antigen binding domain, a hinge domain, a transmembrane domain, a costimulatory signaling region, and a CD3 zeta signaling domain, and wherein when the CAR is transduced into a T cell, the CAR contributes to at least one of: increased antigen-independent activation of the transduced T cell, increased mean cell volume (MCV) of the transduced T cell, increased cell population expansion of the transduced T cell, increased proliferation of the transduced T cell, increased effector cytokine secretion, increased expression of granzyme, increased numbers of progeny of the transduced T cell, increased persistence of the transduced T cell population in vitro, or increased persistence of the transduced T cell population in vivo.

The invention also provides a vector comprising a nucleic acid sequence encoding a chimeric antigen receptor (CAR), the CAR comprising an antigen binding domain, a hinge domain, a transmembrane domain, a costimulatory signaling region, and a CD3 zeta signaling domain, and wherein when the CAR is transduced into a T cell, the CAR contributes to at least one of: increased antigen-independent activation of the transduced T cell, increased mean cell volume (MCV) of the transduced T cell, increased cell population expansion of the transduced T cell, increased proliferation of the transduced T cell, increased numbers of progeny of the transduced T cell, increased persistence of the transduced T cell population in vitro, or increased persistence of the transduced T cell population in vivo.

The invention also provides a persisting population of genetically modified T cells, wherein the T cells comprise a nucleic acid sequence encoding a chimeric antigen receptor (CAR), the CAR comprising an antigen binding domain, a hinge domain, a transmembrane domain, a costimulatory signaling region, and a CD3 zeta signaling domain, and wherein when the CAR is transduced into a T cell, the CAR contributes to at least one of: increased antigen-independent activation of the transduced T cell, increased mean cell volume (MCV) of the transduced T cell, increased cell population expansion of the transduced T cell, increased proliferation of the transduced T cell, increased numbers of progeny of the transduced T cell, increased persistence of the transduced T cell population in vitro, or increased persistence of the transduced T cell population in vivo.

In one embodiment, the genetically modified T cells exhibit an anti-tumor immunity when the antigen binding domain binds to its corresponding antigen.

In one embodiment, the persisting population of genetically modified T cells of exhibit a cytokine signature comprising at least one cytokine selected from the group consisting of IFN-γ, TNF-α, IL-17A, IL-2, IL-3, IL-4, GM-CSF, IL-10, IL-13, Granzyme B, Perforin, and any combination thereof.

In one embodiment, the T cells proliferate in the absence of exogenous cytokine or feeder cells.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1A shows a representation of CAR constructs depicting the various scFv, hinge regions, transmembrane and cytosolic domains. All CARs contain the CD28 and CD3ζ intracellular signaling domain except for the CART19 CAR which contains the 4-1BB rather than CD28 intracellular domain.

FIG. 1B demonstrates that the surface expression of each CAR construct in (FIG. 1A) was analyzed 6 days following lentiviral transduction to quantify relative expression levels.

FIG. 2A shows the in vitro proliferation of human CD4+ T cells following 5 days of αCD3/C1)28 coated magnetic bead stimulation and lentiviral transduction with the indicated CAR constructs (left panel). The c-Met IgG4 CAR and both SS1 CARs exhibit constitutive proliferation for 60 days. No cytokines were added to culture media at any point during expansion. The CAR T cells with constitutive proliferation also maintain a larger mean cell volume (right panel). Results are representative of n>10 normal human donors.

FIGS. 2B and 2C demonstrate that CD4+ and CD8+ T cells were stimulated as in (FIG. 2A), with or without exogenous IL-2. FIG. 2D demonstrates that CD4+ T cells from 3 healthy donors were isolated, stimulated and transduced with lentivirus encoding the c-Met IgG4, CD19 CD8-α, and CART19 CAR constructs or mock transduced, and cultured with addition of fresh media and no exogenous cytokines. Error bars denote standard deviation.

FIG. 3A depicts serial measurements of cytokine production by various CAR constructs following αCD3/CD28 stimulation and expansion. At each noted time point c-Met IgG4, CD19 CD8-α CAR transduced, and untransduced CD4+ T cells were collected from culture, washed and re-plated at 1×10$^6$/mL. Cells were kept in culture for 24 hrs at which time supernatant from each culture was collected. Supernatants were analyzed via luminex assay and values plotted as log(10) fold change from the pre-stimulated cells (baseline). Baseline values (pg/ml) for each analyte were: IFN-γ: 3.66 pg/mL; TNF-α: 0.29 pg/mL; IL-2: 0.51 pg/mL; GM-CSF: 4.58 pg/mL; IL13: 4.79 pg/mL; IL-10: 1.29 pg/mL.

FIG. 3B show supernatant from CARs displaying the growth phenotype induces activation of naive unstimulated T cells. Culture supernatant from c-Met IgG4 CAR T cell culture harvested on day 56 of culture was added to unstimulated naive CD4+ T cells at a final concentration of 12.5%, 25%, or 50% c-Met IgG4 supernatant relative to starting media. As controls, media with and without 100IU of IL-2 were also included, as well as CD3/CD28 bead stimulated cells kept in culture with initial stimulation on day 0 and re-stimulation on day 12. MCVs were determined and cell media was added every two days to maintain the supernatant concentration and IL-2 concentration within control group as described elsewhere herein.

FIG. 4A depict cytokines, perforin and granzyme expression. Microarray analysis comparing cytokine expression of c-Met IgG4, CD19 CD8-α, CART19 CARs and untransduced T cells at baseline and on days 6, 22 and 24 of culture; only the c-Met IgG4 culture was analyzed on day 24 because the other cultures were terminated due to cell death. No exogenous cytokines were added to the culture media. Normalized absolute $\log_2$ gene expression intensities are plotted for IFN-γ, TNF-α, IL-17A, IL-2, IL-3, IL-4, GM-CSF, IL-10, IL-13, Granzyme B and Perforin.

FIG. 4B demonstrates that CAR T cells with a constitutive growth phenotype display distinct transcription factors. Expression of genes important for T cell polarization, growth and survival: T-bet, Eomes, GATA-3, RORc, FoxP3, Bcl-xL, KLRG1, and hTERT. Normalized absolute log(2) gene expression intensities are plotted. Data is compilation of normal donor triplicates analyzed prior to stimulation, and on days 6, 11 and 24; only the c-Met IgG4 culture is analyzed on day 24 because the other cultures were terminated due to cell death. Each dot denotes a single donor within each time point expressing either the c-Met IgG4 CAR, CD19 CD8α CAR, or untransduced control. Box plots representing upper $75^{th}$ and lower $25^{th}$ percentile with median. Whiskers denote upper $90^{th}$ and lower $10^{th}$ percentile. Comparison of c-Met IgG4 CAR vs CD19 CD8α CAR (red) on day 11 by ANOVA: T-bet (p=0.888); Eomes (p=0.003); GATA-3 (p<0.001); FoxP3 (p=0.122); RORc (p=0.089); KLRG1 (P=0.076); hTERT (p=0.405); and Bcl-xL (p<0.001).

FIG. 5A shows a representative FACS histograms displaying enrichment of c-Met IgG4 CAR (+) T cells during culture from day 10 to day 30 of culture.

FIG. 5B depicts PhosFlow plots of CD4+ T cells stimulated and transduced with the c-Met IgG4 or CD19 CD8α CARs. On days 6, 10 and 25 cells were fixed, permeabilized and stained using PE anti-Erk1/2 (pT202/pY204), PE anti-Akt (pS473), PE anti-NF-kB p65 (pS529) and PE anti-S6 (pS235/pS236); the CD19 CD8α CAR culture did not continue to proliferate to day 25, and therefore is only analyzed on days 6 and 10. Positive controls were samples from each condition stimulated for 10 min using PMA/Ionomycin prior to fixation, while negative controls cells were fully stimulated T cells stained using PE conjugated IgG2b κ isotype control.

FIGS. 6A-6C are a series of images summarizing results from a genome-wide microarray analysis of CAR T cells with constitutive proliferation.

FIG. 6A demonstrates that CD4+ T cells from 3 donors expressing continuous c-Met IgG4 or classic CD19 CD8α CARs, or mock transduced cells were subjected to microarray analysis and hierarchical clustering from day 0 to day 24 of culture. Clustering was done using the euclidean distance of median normalized absolute log(2) gene expression intensities with average linkage. The plots are based on unbiased whole genome clustering. On day 11, CD19 CD8α CAR T cells and untransduced cells cluster more similarly to resting T cells, while day 11 and day 24 c-Met IgG4 CAR T cells remain activated and closely cluster.

FIG. 6B shows a distinct gene expression signature of CAR T cells with constitutive proliferation. The gene expression signatures from the 3 donor T cell cultures on day 6 is compared to day 11 and day 24 cultures. CAR T cells on day 6 are similar to mock transduced T cells. In contrast, on day 11 and day 24 the continuous c-Met IgG4 cells display a unique RNA signature that differs from the fully activated day 6 phenotype.

FIG. 6C shows the differences in expression of genes between c-Met CAR and CD19 CAR.

FIG. 7A demonstrates that population doublings were determined for both CMV and EF-1α driven c-MET CAR cells. After ~12 days in culture, CMV-c-MET CAR cells were unable to sustain proliferation and died, while EF-1α c-MET CAR T cell continue to proliferate.

FIG. 7B demonstrates that Mean cell volume (MCV) was also determined. The CMV-c-MET CAR T cells decreased in cell size after 10 days, indicative of the cells resting down.

FIG. 7C depicts a comparison of the level of expression between CARs expressed with the CMV and EF-1α promoters at day 6 post-transduction. The mean fluorescence intensity is indicated.

Figure 12:
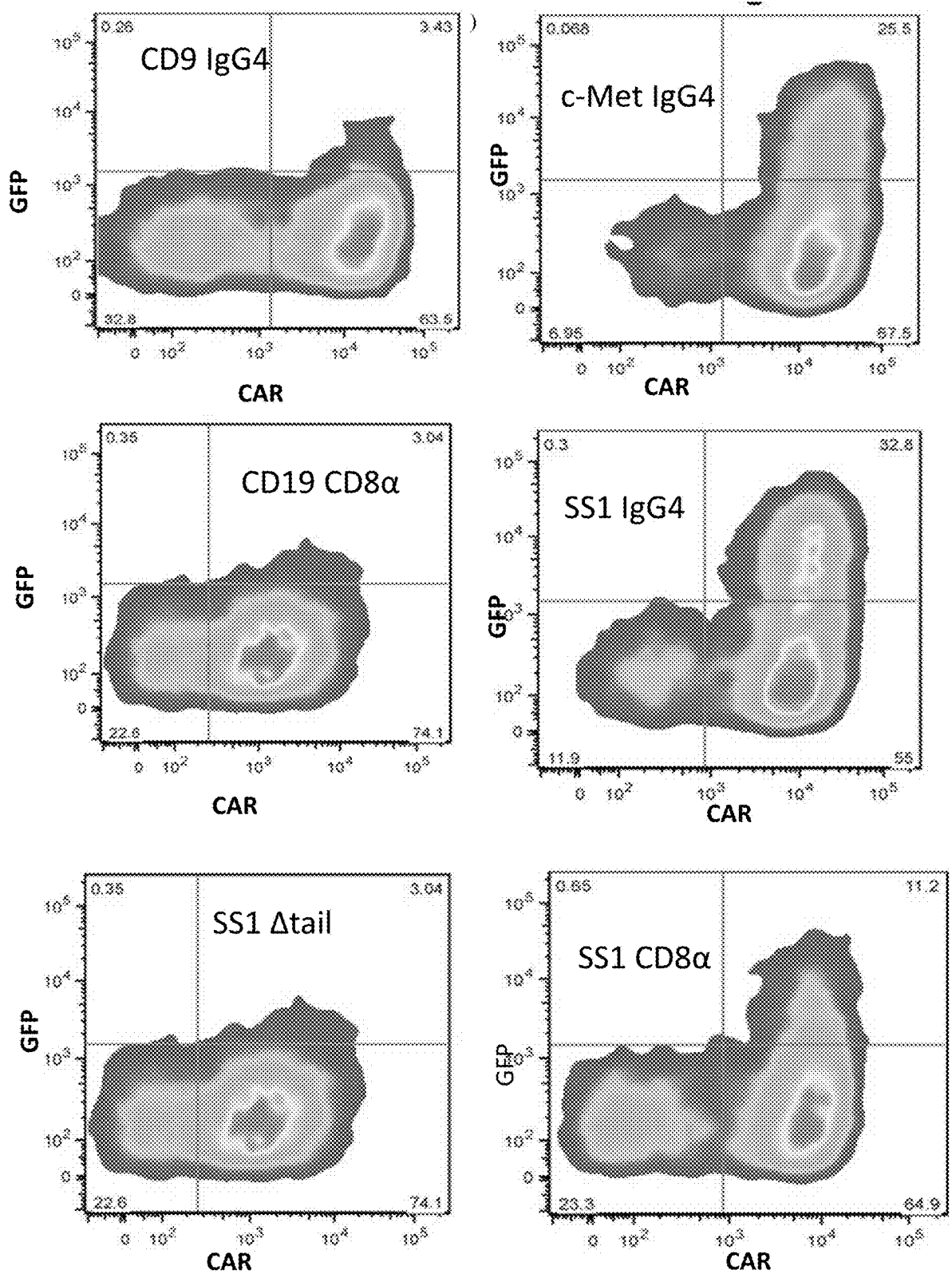
FIG. 12 is an image demonstrating that CAR T cells with constitutive proliferation have ligand-independent NFAT activation. Jurkat T cells engineered to express GFP under the control of the NFAT promoter were transduced with lentivirus encoding CARs for continuous c-Met IgG4, SS1 IgG4, SS1 CD8α, and classic CARs encoding CD19 IgG4, CD19 CD8α, and SS1 CD8aΔtail. Cells were analyzed 3 days following transduction for GFP and CAR expression

Companion CD4 T cells were isolated via negative depletion and stimulated concurrently with the CAR T cells shown in FIG. 12. Pre-stimulation cells were cryopreserved for later analysis. Cell samples were isolated for analysis at day 6, 24 hours following bead removal, and on day 14. Cells were thawed simultaneously with the CAR T cells and rested overnight without additional of growth factors or cytokines. Cells were analyzed for CAR expression as well as CD25, CD70, PD-1, CD27, CD28, CD62L, CCR7 and Crtam.

Figure 15:
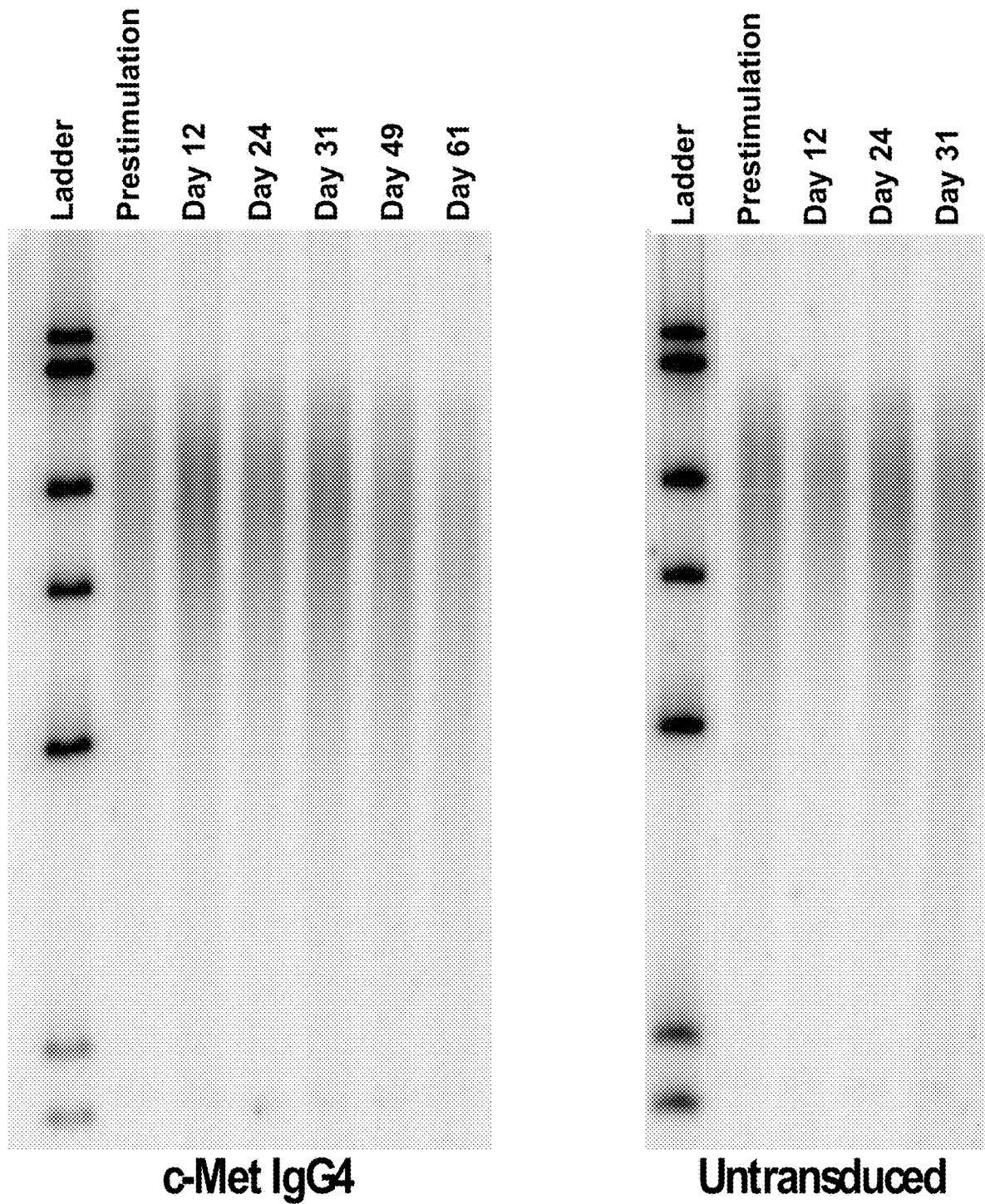

FIG. 15 is an image depicting temporal patterns of telomere restriction fragment length (TRF) in continuous CAR T cells and mock transduced T cells. CD4 T cells transduced with the continuous c-Met IgG4 CAR or mock transduced cells were cultured for the indicated duration. DNA was isolated from the T cells and terminal telomeric restriction fragment length assessed by electrophoretic separation of HinfI/RsaI digested DNA followed by in-gel hybridization to a telomere repeat probe. The continuous CAR T cells proliferated for at least 61 days in culture while the mock transduced T cells ceased proliferation after 31 days. The ladder is 32P-labeled mixture of full-length and HindIII-digested lambda DNA.

Figure 16:
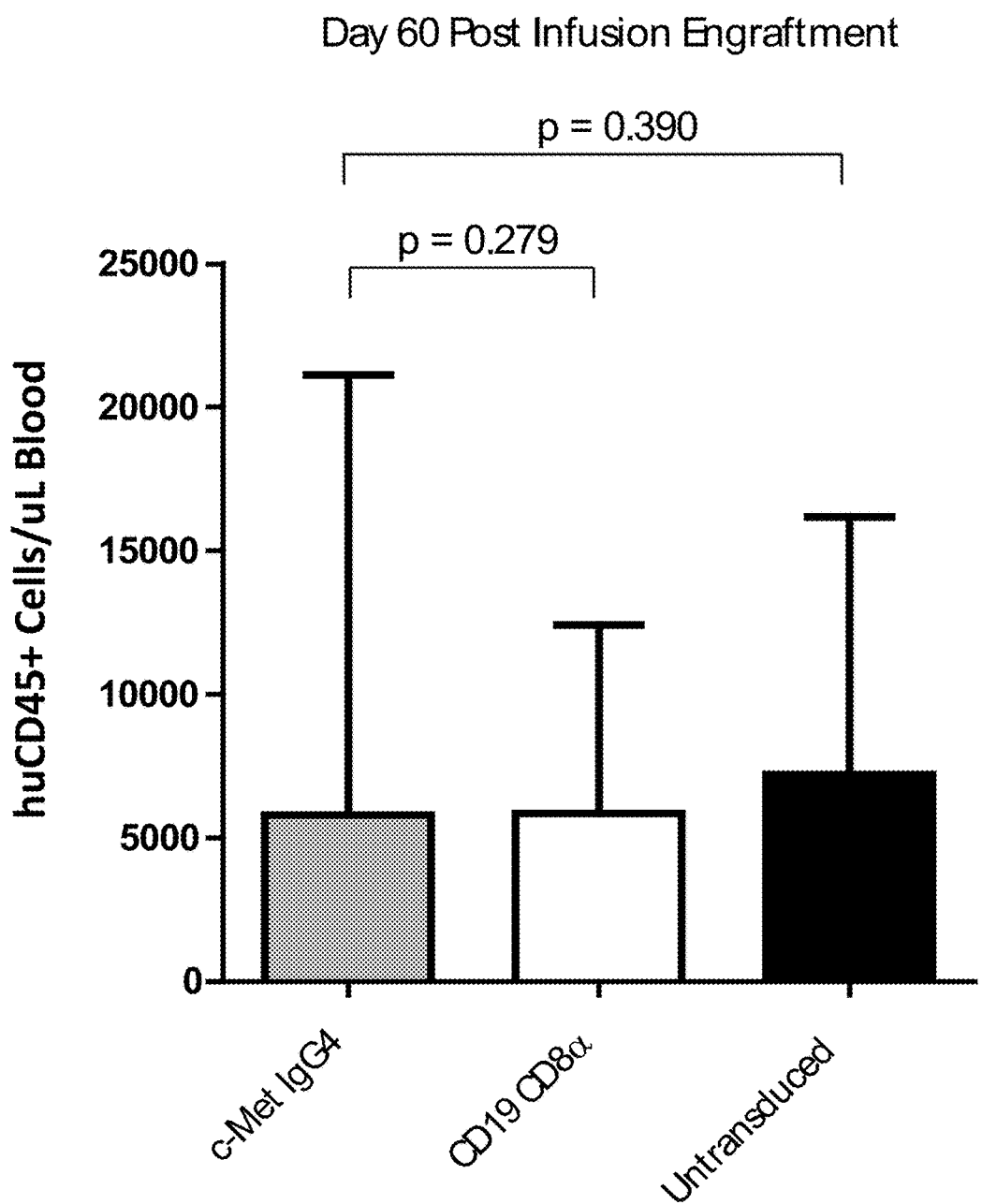

FIG. 16 is an image depicting engraftment and proliferation of continuous CAR T cells in NSG mice. Human CD4 T cells ($10^6$) expressing the continuous c-Met IgG4 CAR, the classic CD19 CD8α CAR (adjusted to 50% CAR positivity) or mock transduced T cells were infused into NSG mice (n=10 mice per group). Mice were analyzed 60 days following infusion by peripheral blood TruCounts to quantify huCD45+ cells per uL of mouse blood. Sample means were not different (two tailed Mann-Whitney p=0.39); the bars denote S.D.

DETAILED DESCRIPTION

The invention relates to the discovery that particular chimeric antigen receptors (CARs) transduced into T cells contribute at least to increased antigen-independent activation of the transduced T cells, increased mean cell volume (MCV) of the transduced T cells, increased cell population expansion of the transduced T cells, increased proliferation of the transduced T cells, increased numbers of progeny of the transduced T cells, and increased persistence of the transduced T cell population both in vitro and in vivo. Thus, the invention relates to compositions and methods for treating cancer, including, but not limited, to hematologic malignancies and solid tumors, by the administration of T cells transduced with CARs that contribute to increased activation and persistence of the transduced T cell population. The present invention relates to a strategy of adoptive cell transfer of T cells transduced to express a chimeric antigen receptor (CAR). CARs are molecules that combine antibody-based specificity for a desired antigen (e.g., tumor antigen) with a T cell receptor-activating intracellular domain to generate a chimeric protein that exhibits a specific anti-tumor cellular immune activity.

The invention provides a method for identification of CAR designs that permit extensive T-cell proliferation without exogenous cytokine administration or feeder cells. In one aspect, the invention provides compositions and methods for generating CARs that endow T cells with the ability to undergo long-term autonomous proliferation. In one aspect the long-term proliferation and expansion of CAR T cells are independent of antigen stimulation and do not require the addition of exogenous cytokines or feeder cells.

In one aspect, the long-term proliferation and expansion of CAR T cells is partially mediated by constitutive cytokine production. Accordingly, the invention provides a unique molecular signature of CAR T cells having a constitutive proliferative phenotype. In one aspect, the unique molecule signature of CAR T cells include the expression of one or more of IFN-γ, TNF-α, IL-17A, IL-2, IL-3, IL-4, GM-CSF, IL-10, IL-13, Granzyme B and Perforin.

In another embodiment, the invention provides a method of generating a CAR T cell exhibiting a continuous growth phenotype. In one aspect, the continuous growth phenotype involves continuous ligand-independent signal transduction involving canonical TCR and CD28 signal transduction pathways. In another aspect, the continuous proliferation phenotype of the CAR T cells can be identified by evaluating the level of scFv surface expression on the CAR T cells, as CARs expressed brightly at the cell surface sustained proliferation, while CARs expressing at lower level of scFv surface expressing did not exhibit sustained proliferation and cytokine secretion.

In one embodiment, the CAR of the invention comprises an extracellular domain having an antigen recognition domain, a transmembrane domain, and a cytoplasmic domain. In one embodiment, the transmembrane domain that naturally is associated with one of the domains in the CAR is used. In another embodiment, the transmembrane domain can be selected or modified by amino acid substitution to avoid binding of such domains to the transmembrane domains of the same or different surface membrane proteins to minimize interactions with other members of the receptor complex. Preferably, the hinge domain is an IgG4 or CD8α hinge domain.

In various embodiments, the persisting CAR T cells of the invention can be generated by introducing a lentiviral vector comprising a desired CAR that contributes to at least one of increased antigen-independent activation of the transduced T cells, increased mean corpuscular volume (MCV) of the transduced T cells, increased cell population expansion of the transduced T cells, increased proliferation of the transduced T cells, increased numbers of progeny of the transduced T cells, and increased persistence of the transduced T cell population both in vitro and in vivo. By way of example, the CAR of the invention comprises an anti-c-Met, IgG4 hinge, CD28 transmembrane and CD28 and CD3zeta signaling domains. By way of another example, the CAR of the invention comprises an anti-mesothelin (SS1), IgG4 hinge, CD28 transmembrane and CD28 and CD3zeta signaling domains. By way of another example, the CAR of the invention comprises an anti-mesothelin, CD8a hinge, CD28 transmembrane domain and CD28 and CD3zeta signaling domains. By way of another example, the CAR of the invention comprises an anti-CD19, IgG4 hinge, CD28 transmembrane, and CD28 and CD3zeta signaling domains. By way of another example, the CAR of the invention comprises an anti-CD19, CD8a hinge domain, CD28 transmembrane and CD28 and CD3zeta signaling domains. The CAR T cells of the invention are able to replicate in vivo resulting in long-term persistence that can lead to sustained tumor control.

In one embodiment the invention relates to administering a genetically modified T cell expressing a CAR for the treatment of a patient having cancer or at risk of having cancer using lymphocyte infusion. Preferably, autologous lymphocyte infusion is used in the treatment. Autologous PBMCs are collected from a patient in need of treatment and T cells are activated and expanded using the methods described herein and known in the art and then infused back into the patient.

Definitions

Unless defined otherwise, all technical and scientific terms used herein have the same meaning as commonly understood by one of ordinary skill in the art to which the invention pertains. Although any methods and materials similar or equivalent to those described herein can be used in the practice of and/or for the testing of the present invention, the preferred materials and methods are described herein. In describing and claiming the present invention, the following terminology will be used according to how it is defined, where a definition is provided.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or in some instances ±10%, or in some instances ±5%, or in some instances ±1%, or in some instances ±0.1% from the specified value, as such variations are appropriate to perform the disclosed methods.

"Activation," as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The an antibody in the present invention may exist in a variety of forms where the antigen binding portion of the antibody is expressed as part of a contiguous polypeptide chain including, for example, a single domain antibody fragment (sdAb), a single chain antibody (scFv) and a humanized antibody (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antibody fragment" refers to at least one portion of an intact antibody and refers to the antigenic determining variable regions of an intact antibody. Examples of antibody fragments include, but are not limited to, Fab, Fab', F(ab')2, and Fv fragments, linear antibodies, sdAb (either $V_L$ or $V_H$), camelid $V_{HH}$ domains, scFv antibodies, and multi-specific antibodies formed from antibody fragments. The term "scFv" refers to a fusion protein comprising at least one antibody fragment comprising a variable region of a light chain and at least one antibody fragment comprising a variable region of a heavy chain, wherein the light and heavy chain variable regions are contiguously linked via a short flexible polypeptide linker, and capable of being expressed as a single chain polypeptide, and wherein the scFv retains the specificity of the intact antibody from which it was derived. Unless specified, as used herein an scFv may have the $V_L$ and $V_H$ variable regions in either order, e.g., with respect to the N-terminal and C-terminal ends of the polypeptide, the scFv may comprise $V_L$-linker-$V_H$ or may comprise $V_H$-linker-$V_L$.

An "antibody heavy chain," as used herein, refers to the larger of the two types of polypeptide chains present in antibody molecules in their naturally occurring conformations, and which normally determines the class to which the antibody belongs.

An "antibody light chain," as used herein, refers to the smaller of the two types of polypeptide chains present in antibody molecules in their naturally occurring conformations. Kappy (κ) and lambda (λ) light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to encode polypeptides that elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid. The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

The term "auto-antigen" means, in accordance with the present invention, any self-antigen which is mistakenly recognized by the immune system as being foreign. Auto-antigens comprise, but are not limited to, cellular proteins, phosphoproteins, cellular surface proteins, cellular lipids, nucleic acids, glycoproteins, including cell surface receptors.

The term "autoimmune disease" as used herein is defined as a disorder that results from an autoimmune response. An autoimmune disease is the result of an inappropriate and excessive response to a self-antigen. Examples of autoimmune diseases include but are not limited to, Addision's disease, alopecia greata, ankylosing spondylitis, autoimmune hepatitis, autoimmune parotitis, Crohn's disease, diabetes (Type I), dystrophic epidermolysis bullosa, epididymitis, glomerulonephritis, Graves' disease, Guillain-Barr syndrome, Hashimoto's disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjogren's syndrome, spondyloarthropathies, thyroiditis, vasculitis, vitiligo, myxedema, pernicious anemia, ulcerative colitis, among others.

As used herein, the term "autologous" is meant to refer to any material derived from the same individual to which it is later to be re-introduced into the individual.

"Allogeneic" refers to a graft derived from a different animal of the same species.

"Xenogeneic" refers to a graft derived from an animal of a different species.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

"Co-stimulatory ligand," as the term is used herein, includes a molecule on an antigen presenting cell (e.g., an aAPC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class I molecule, BTLA and a Toll ligand receptor.

A "co-stimulatory signal", as used herein, refers to a signal, which in combination with a primary signal, such as TCR/CD3 ligation, leads to T cell proliferation and/or upregulation or downregulation of key molecules.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

An "effective amount" as used herein, means an amount which provides a therapeutic or prophylactic benefit.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared X 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

The term "immunoglobulin" or "Ig," as used herein is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

The terms "microarray" and "array" refers broadly to both "DNA microarrays" and "DNA chip(s)," and encompasses all art-recognized solid supports, and all art-recognized methods for affixing nucleic acid molecules thereto or for synthesis of nucleic acids thereon. Preferred arrays typically comprise a plurality of different nucleic acid probes that are coupled to a surface of a substrate in different, known locations. These arrays, also described as "microarrays" or colloquially "chips" have been generally described in the art, for example, U.S. Pat. Nos. 5,143,854, 5,445,934, 5,744, 305, 5,677,195, 5,800,992, 6,040,193, 5,424,186 and Fodor et al., 1991, Science, 251:767-777, each of which is incorporated by reference in its entirety for all purposes. Arrays may generally be produced using a variety of techniques, such as mechanical synthesis methods or light directed synthesis methods that incorporate a combination of photolithographic methods and solid phase synthesis methods.

Techniques for the synthesis of these arrays using mechanical synthesis methods are described in, e.g., U.S. Pat. Nos. 5,384,261, and 6,040,193, which are incorporated herein by reference in their entirety for all purposes. Although a planar array surface is preferred, the array may be fabricated on a surface of virtually any shape or even a multiplicity of surfaces. Arrays may be nucleic acids on beads, gels, polymeric surfaces, fibers such as fiber optics, glass or any other appropriate substrate. (See U.S. Pat. Nos. 5,770,358, 5,789, 162, 5,708,153, 6,040,193 and 5,800,992, which are hereby incorporated by reference in their entirety for all purposes.) Arrays may be packaged in such a manner as to allow for diagnostic use or can be an all-inclusive device; e.g., U.S. Pat. Nos. 5,856,174 and 5,922,591 incorporated in their entirety by reference for all purposes. Arrays are commercially available from, for example, Affymetrix (Santa Clara, Calif.) and Applied Biosystems (Foster City, Calif.), and are directed to a variety of purposes, including genotyping, diagnostics, mutation analysis, marker expression, and gene expression monitoring for a variety of eukaryotic and prokaryotic organisms. The number of probes on a solid support may be varied by changing the size of the individual features. In one embodiment the feature size is 20 by 25 microns square, in other embodiments features may be, for example, 8 by 8, 5 by 5 or 3 by 3 microns square, resulting in about 2,600,000, 6,600,000 or 18,000,000 individual probe features.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

The term "overexpressed" tumor antigen or "overexpression" of the tumor antigen is intended to indicate an abnormal level of expression of the tumor antigen in a cell from a disease area like a solid tumor within a specific tissue or organ of the patient relative to the level of expression in a normal cell from that tissue or organ. Patients having solid tumors or a hematological malignancy characterized by overexpression of the tumor antigen can be determined by standard assays known in the art.

"Parenteral" administration of an immunogenic composition includes, e.g., subcutaneous (s.c.), intravenous (i.v.), intramuscular (i.m.), or intrasternal injection, or infusion techniques.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-$\beta$, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

The term "therapeutic" as used herein means a treatment and/or prophylaxis. A therapeutic effect is obtained by suppression, remission, or eradication of a disease state.

The term "therapeutically effective amount" refers to the amount of the subject compound that will elicit the biological or medical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

To "treat" a disease as the term is used herein, means to reduce the frequency or severity of at least one sign or symptom of a disease or disorder experienced by a subject.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention relates to compositions and methods of transducing T cells with chimeric antigen receptors (CARs) that generate a persisting population of T cells that exhibit increased antigen-independent activation, increased mean cell volume (MCV), increased cell population expansion, increased proliferation, increased numbers of progeny, induction of constitutive cytokine secretion, and increased persistence of the transduced T cell population both in vitro and in vivo, as compared with their untransduced counterparts. Thus, the present invention includes compositions and methods for treating cancer among other diseases. The cancer may be a hematological malignancy, a solid tumor, a primary or a metastasizing tumor. Other diseases treatable using the compositions and methods of the invention include viral, bacterial and parasitic infections as well as autoimmune diseases.

In one embodiment, the invention provides a cell (e.g., T cell) engineered to express a CAR that contributes to increased activation or proliferation of the transduced T cell and wherein the CAR T cell exhibits an antitumor property. The CAR of the invention can be engineered to comprise an extracellular domain having an antigen binding domain fused to an intracellular signaling domain of the T cell antigen receptor complex zeta chain (e.g., CD3 zeta). The CAR of the invention when expressed in a T cell is able to redirect antigen recognition based on the antigen binding specificity. Exemplary antigens include cMet, mesothelin and CD19. However, the invention is not limited to targeting cMet, mesothelin and CD19. Rather, the invention includes any antigen binding moiety that when bound to its cognate antigen, affects a tumor cell so that the tumor cell fails to grow, is prompted to die, or otherwise is affected so that the tumor burden in a patient is diminished or eliminated. The antigen binding moiety is preferably fused with an intracellular domain from one or more of a costimulatory molecule and a zeta chain. Preferably, the antigen binding moiety is fused with one or more intracellular domains selected from the group of a CD137 (4-1BB) signaling domain, a CD28 signaling domain, a CD3-zeta signaling domain, and any combination thereof.

Compositions

The present invention provides chimeric antigen receptor (CAR) comprising an extracellular and intracellular domain. The extracellular domain comprises a target-specific binding element otherwise referred to as an antigen binding moiety. In some embodiment, the extracellular domain also comprises a hinge domain. The intracellular domain or otherwise the cytoplasmic domain comprises, a costimulatory signaling region and a zeta chain portion. The costimulatory signaling region refers to a portion of the CAR comprising the intracellular domain of a costimulatory molecule. Costimulatory molecules are cell surface molecules other than antigens receptors or their ligands that are required for an efficient response of lymphocytes to antigen.

Between the extracellular domain and the transmembrane domain of the CAR, or between the cytoplasmic domain and the transmembrane domain of the CAR, there may be incorporated a spacer domain. As used herein, the term "spacer domain" generally means any oligo- or polypeptide that functions to link the transmembrane domain to, either the extracellular domain or, the cytoplasmic domain in the polypeptide chain. A spacer domain may comprise up to 300 amino acids, preferably 10 to 100 amino acids and most preferably 25 to 50 amino acids.

Antigen Binding Moiety

In one embodiment, the CAR of the invention comprises a target-specific binding element otherwise referred to as an antigen binding moiety. The choice of moiety depends upon the type and number of ligands that define the surface of a target cell. For example, the antigen binding domain may be chosen to recognize a ligand that acts as a cell surface marker on target cells associated with a particular disease state. Thus examples of cell surface markers that may act as ligands for the antigen moiety domain in the CAR of the invention include those associated with viral, bacterial and parasitic infections, autoimmune disease and cancer cells.

In one embodiment, the CAR of the invention can be engineered to target a tumor antigen of interest by way of engineering a desired antigen binding moiety that specifically binds to an antigen on a tumor cell. In the context of the present invention, "tumor antigen" or "hyperporolifera-tive disorder antigen" or "antigen associated with a hyper-proliferative disorder," refers to antigens that are common to specific hyperproliferative disorders such as cancer. The antigens discussed herein are merely included by way of example. The list is not intended to be exclusive and further examples will be readily apparent to those of skill in the art.

Tumor antigens are proteins that are produced by tumor cells that elicit an immune response, particularly T-cell mediated immune responses. The selection of the antigen binding moiety of the invention will depend on the particular type of cancer to be treated. Tumor antigens are well known in the art and include, for example, a glioma-associated antigen, carcinoembryonic antigen (CEA), β-human chori-onic gonadotropin, alphafetoprotein (AFP), lectin-reactive AFP, thyroglobulin, RAGE-1, MN-CA IX, human telom-erase reverse transcriptase, RU1, RU2 (AS), intestinal car-boxyl esterase, mut hsp70-2, M-CSF, prostase, prostate-specific antigen (PSA), PAP, NY-ESO-1, LAGE-1a, p53, prostein, PSMA, Her2/neu, survivin and telomerase, pros-tate-carcinoma tumor antigen-1 (PCTA-1), MAGE, ELF2M, neutrophil elastase, ephrinB2, CD22, insulin growth factor (IGF)-I, IGF-II, IGF-I receptor and mesothelin.

In one embodiment, the tumor antigen comprises one or more antigenic cancer epitopes associated with a malignant tumor. Malignant tumors express a number of proteins that can serve as target antigens for an immune attack. These molecules include but are not limited to tissue-specific antigens such as MART-1, tyrosinase and GP 100 in mela-noma and prostatic acid phosphatase (PAP) and prostate-specific antigen (PSA) in prostate cancer. Other target mol-ecules belong to the group of transformation-related molecules such as the oncogene HER-2/Neu/ErbB-2. Yet another group of target antigens are onco-fetal antigens such as carcinoembryonic antigen (CEA). In B-cell lymphoma the tumor-specific idiotype immunoglobulin constitutes a truly tumor-specific immunoglobulin antigen that is unique to the individual tumor. B-cell differentiation antigens such as CD19, CD20 and CD37 are other candidates for target antigens in B-cell lymphoma. Some of these antigens (CEA, HER-2, CD19, CD20, idiotype) have been used as targets for passive immunotherapy with monoclonal antibodies with limited success.

The type of tumor antigen referred to in the invention may also be a tumor-specific antigen (TSA) or a tumor-associated antigen (TAA). A TSA is unique to tumor cells and does not occur on other cells in the body. A TAA associated antigen is not unique to a tumor cell and instead is also expressed on a normal cell under conditions that fail to induce a state of immunologic tolerance to the antigen. The expression of the antigen on the tumor may occur under conditions that enable the immune system to respond to the antigen. TAAs may be antigens that are expressed on normal cells during fetal development when the immune system is immature and unable to respond or they may be antigens that are normally present at extremely low levels on normal cells but which are expressed at much higher levels on tumor cells.

Non-limiting examples of TSA or TAA antigens include the following: Differentiation antigens such as MART-1/MelanA (MART-I), gp100 (Pmel 17), tyrosinase, TRP-1, TRP-2 and tumor-specific multilineage antigens such as MAGE-1, MAGE-3, BAGE, GAGE-1, GAGE-2, p15; over-expressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, p185erbB2, p180erbB-3, cMet, nm-23H1, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCAS1, SDCCAG16, TA-90\Mac-2 binding protein\cyclophilin C-associated pro-tein, TAAL6, TAG72, TLP, and TPS.

In a preferred embodiment, the antigen binding moiety portion of the CAR targets an antigen that includes but is not limited to cMet, CD19, CD20, CD22, ROR1, Mesothelin, CD33/IL3Ra, cMet, PSMA, Glycolipid F77, EGFRvIII, GD-2, MY-ESO-1 TCR, MAGE A3 TCR, and the like.

Depending on the desired antigen to be targeted, the CAR of the invention can be engineered to include the appropriate antigen bind moiety that is specific to the desired antigen target. For example, if CD19 is the desired antigen that is to be targeted, an antibody for CD19 can be used as the antigen bind moiety for incorporation into the CAR of the invention.

Transmembrane Domain

With respect to the transmembrane domain, the CAR can be designed to comprise a transmembrane domain that is fused to the extracellular domain of the CAR. In one embodiment, the transmembrane domain that naturally is associated with one of the domains in the CAR is used. In some instances, the transmembrane domain can be selected or modified by amino acid substitution to avoid binding of such domains to the transmembrane domains of the same or different surface membrane proteins to minimize interac-tions with other members of the receptor complex.

The transmembrane domain may be derived either from a natural or from a synthetic source. Where the source is natural, the domain may be derived from any membrane-bound or transmembrane protein. Transmembrane regions of particular use in this invention may be derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, or from an immunoglobulin such as IgG4. Alternatively the transmem-brane domain may be synthetic, in which case it will comprise predominantly hydrophobic residues such as leu-cine and valine. Preferably a triplet of phenylalanine, tryp-tophan and valine will be found at each end of a synthetic transmembrane domain. Optionally, a short oligo- or poly-peptide linker, preferably between 2 and 10 amino acids in length may form the linkage between the transmembrane domain and the cytoplasmic signaling domain of the CAR. A glycine-serine doublet provides a particularly suitable linker.

Cytoplasmic Domain

The cytoplasmic domain or otherwise the intracellular signaling domain of the CAR of the invention is responsible for activation of at least one of the normal effector functions of the immune cell in which the CAR has been placed in. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Preferred examples of intracellular signaling domains for use in the CAR of the invention include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

It is known that signals generated through the TCR alone are insufficient for full activation of the T cell and that a secondary or co-stimulatory signal is also required. Thus, T cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs.

Examples of ITAM containing primary cytoplasmic signaling sequences that are of particular use in the invention include those derived from TCR zeta, FcR gamma, FcR beta, CD3 gamma, CD3 delta, CD3 epsilon, CD5, CD22, CD79a, CD79b, and CD66d. It is particularly preferred that cytoplasmic signaling molecule in the CAR of the invention comprises a cytoplasmic signaling sequence derived from CD3-zeta.

In a preferred embodiment, the cytoplasmic domain of the CAR can be designed to comprise the CD3-zeta signaling domain by itself or combined with any other desired cytoplasmic domain(s) useful in the context of the CAR of the invention. For example, the cytoplasmic domain of the CAR can comprise a CD3 zeta chain portion and a costimulatory signaling region. The costimulatory signaling region refers to a portion of the CAR comprising the intracellular domain of a costimulatory molecule. A costimulatory molecule is a cell surface molecule other than an antigen receptor or its ligands that is required for an efficient response of lymphocytes to an antigen. Examples of such molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like. Thus, while the invention in exemplified primarily with 4-1BB as the co-stimulatory signaling element, other costimulatory elements are within the scope of the invention.

The cytoplasmic signaling sequences within the cytoplasmic signaling portion of the CAR of the invention may be linked to each other in a random or specified order. Optionally, a short oligo- or polypeptide linker, preferably between 2 and 10 amino acids in length may form the linkage. A glycine-serine doublet provides a particularly suitable linker.

In one embodiment, the cytoplasmic domain is designed to comprise the signaling domain of CD3-zeta and the signaling domain of CD28. In another embodiment, the cytoplasmic domain is designed to comprise the signaling domain of CD3-zeta and the signaling domain of 4-1BB. In yet another embodiment, the cytoplasmic domain is designed to comprise the signaling domain of CD3-zeta and the signaling domain of CD28 and 4-1BB.

Vectors

The present invention encompasses a DNA construct comprising sequences of a CAR, wherein the sequence comprises the nucleic acid sequence of an antigen binding moiety operably linked to the nucleic acid sequence of an intracellular domain. An exemplary intracellular domain that can be used in the CAR of the invention includes but is not limited to the intracellular domain of CD3-zeta, CD28, 4-1BB, and the like. In some instances, the CAR can comprise any combination of CD3-zeta, CD28, 4-1BB, and the like.

In one embodiment, the CAR of the invention comprises an anti-cMet, IgG4 hinge domain, and CD28 transmembrane and CD28 and CD3zeta signaling domains. In another embodiment, the CAR of the invention comprises an anti-mesothelin, IgG4 hinge domain, and CD28 and CD3zeta signaling domains. In a further embodiment, the CAR of the invention comprises an anti-mesothelin, CD8a hinge domain, and CD28 transmembrane and CD28 and CD3zeta signaling domains. In yet another embodiment, the CAR of the invention comprises an anti-CD19, IgG4 hinge domain, and CD28 transmembrane and CD3zeta signaling domains. In still another embodiment, the CAR of the invention comprises an anti-CD19, CD8a hinge domain, and CD28 transmembrane and CD28 and CD3zeta signaling domains.

In one embodiment, the CAR of the invention comprises the nucleic acid sequence set forth in SEQ ID NO: 1. In another embodiment, the CAR of the invention comprises the nucleic acid sequence set forth in SEQ ID NO: 2. In a further embodiment, the CAR of the invention comprises the nucleic acid sequence set forth in SEQ ID NO: 3.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

The present invention also provides vectors in which a DNA of the present invention is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

In brief summary, the expression of natural or synthetic nucleic acids encoding CARs is typically achieved by operably linking a nucleic acid encoding the CAR polypeptide or portions thereof to a promoter, and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

The expression constructs of the present invention may also be used for nucleic acid immunization and gene therapy, using standard gene delivery protocols. Methods for gene delivery are known in the art. See, e.g., U.S. Pat. Nos.

5,399,346, 5,580,859, 5,589,466, incorporated by reference herein in their entireties. In another embodiment, the invention provides a gene therapy vector.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

Sources of T Cells

Prior to expansion and genetic modification of the T cells of the invention, a source of T cells is obtained from a subject. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available in the art, may be used. In certain embodiments of the present invention, T cells can be obtained from a unit of blood collected from a subject using any number of techniques known to the skilled artisan, such as Ficoll™ separation. In one preferred embodiment, cells from the circulating blood of an individual are obtained by apheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Again, surprisingly, initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, $Ca^{2+}$-free, $Mg^{2+}$-free PBS, PlasmaLyte A, or other saline solution with or without buffer. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as $CD3^+$, $CD28^+$, $CD4^+$, $CD8^+$, $CD45RA^+$, and $CD45RO^+T$ cells, can be further isolated by positive or negative selection techniques. For example, in one embodiment, T cells are isolated by incubation with anti-$CD3$/anti-CD28 (i.e., 3×28)-conjugated beads, such as DYNABEADS® M-450 CD3/CD28 T, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immune-compromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention. In certain embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4$^+$ cells by negative selection, a monoclonal antibody cocktail typically includes antibodies to CD14, CD20, CD11b, CD16, HLA-DR, and CD8. In certain embodiments, it may be desirable to enrich for or positively select for regulatory T cells which typically express CD4$^+$, CD25$^+$, CD62L$^{hi}$, GITR$^+$, and FoxP3$^+$.

Alternatively, in certain embodiments, T regulatory cells are depleted by anti-C25 conjugated beads or other similar method of selection.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain. For example, using high concentration of cells allows more efficient selection of CD8$^+$ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4$^+$ T cells express higher levels of CD28 and are more efficiently captured than CD8$^+$ T cells in dilute concentrations. In one embodiment, the concentration of cells used is 5×10$^6$/ml. In other embodiments, the concentration used can be from about 1×10$^5$/ml to 1×10$^6$/ml, and any integer value in between.

In other embodiments, the cells may be incubated on a rotator for varying lengths of time at varying speeds at either 2-10° C. or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In certain embodiments, cryopreserved cells are thawed and washed as described herein and allowed to rest for one hour at room temperature prior to activation using the methods of the present invention.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one embodiment a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T cells may be expanded, frozen, and used at a later time. In certain embodiments, samples are collected from a patient shortly after diagnosis of a particular disease as described herein but prior to any treatments. In a further embodiment, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1991; Henderson et al., Immun. 73:316-321, 1991; Bierer et al., Curr. Opin. Immun. 5:763-773, 1993). In a further embodiment, the cells are isolated for a patient and frozen for later use in conjunction with (e.g., before, simultaneously or following) bone marrow or stem cell transplantation, T cell ablative therapy using either chemotherapy agents such as, fludarabine, external-beam radiation therapy (XRT), cyclophosphamide, or antibodies such as OKT3 or CAMPATH. In another embodiment, the cells are isolated prior to and can be frozen for later use for treatment following B-cell ablative therapy such as agents that react with CD20, e.g., Rituxan.

In a further embodiment of the present invention, T cells are obtained from a patient directly following treatment. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

Activation and Expansion of T Cells

Whether prior to or after genetic modification of the T cells to express a desirable CAR, the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, the T cells of the invention are expanded by contact with a surface having attached thereto an agent that stimulates a CD3/TCR complex associated signal and a ligand that stimulates a co-stimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either $CD4^+$ T cells or $CD8^+$ T cells, an anti-CD3 antibody and an anti-CD28 antibody. Examples of an anti-CD28 antibody include 9.3, B-T3, XR-CD28 (Diaclone, Besancon, France) can be used as can other methods commonly known in the art (Berg et al., Transplant Proc. 30(8):3975-3977, 1998; Haanen et al., J. Exp. Med. 190(9):13191328, 1999; Garland et al., J. Immunol Meth. 227(1-2):53-63, 1999).

In certain embodiments, the primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In one embodiment, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-CD28 antibody or antigen-binding fragment thereof; and both agents are co-immobilized to the same bead in equivalent molecular amounts. In one embodiment, a 1:1 ratio of each antibody bound to the beads for $CD4^+$ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular embodiment an increase of from about 1 to about 3 fold is observed as compared to the expansion observed using a ratio of 1:1. In one embodiment, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e., the ratio of CD3:CD28 is less than one. In certain embodiments of the invention, the ratio of anti CD28 antibody to anti CD3 antibody bound to the beads is greater than 2:1. In one particular embodiment, a 1:100 CD3:CD28 ratio of antibody bound to beads is used. In another embodiment, a 1:75 CD3:CD28 ratio of antibody bound to beads is used. In a further embodiment, a 1:50 CD3:CD28 ratio of antibody bound to beads is used. In another embodiment, a 1:30 CD3:CD28 ratio of antibody bound to beads is used. In one preferred embodiment, a 1:10 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain embodiments the ratio of cells to particles ranges from 1:100 to 100:1 and any integer values in-between and in further embodiments the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In one embodiment, a ratio of particles to cells of 1:1 or less is used. In one particular embodiment, a preferred particle: cell ratio is 1:5. In further embodiments, the ratio of particles to cells can be varied depending on the day of stimulation. For example, in one embodiment, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular embodiment, the ratio of particles to cells is 1:1 on the first day of stimulation and adjusted to 1:5 on the third and fifth days of stimulation. In another embodiment, particles are added on a daily or every other day basis to a final ratio of 1:1 on the first day, and 1:5 on the third and fifth days of stimulation. In another embodiment, the ratio of particles to cells is 2:1 on the first day of stimulation and adjusted to 1:10 on the third and fifth days of stimulation. In another embodiment, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type.

In further embodiments of the present invention, the cells, such as T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one embodiment the cells (for example, $10^4$ to $10^9$ T cells) and beads (for example, DYNABEADS® M-450 CD3/CD28 T paramagnetic beads at a ratio of 1:1) are combined in a buffer, preferably PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present invention. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain embodiments. For example, using high concentration of cells allows more efficient selection of CD8+ T cells that normally have weaker CD28 expression.

In one embodiment of the present invention, the mixture may be cultured for several hours (about 3 hours) to about 14 days or any hourly integer value in between. In another embodiment, the mixture may be cultured for 21 days. In one embodiment of the invention the beads and the T cells are cultured together for about eight days. In another embodiment, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

T cells that have been exposed to varied stimulation times may exhibit different characteristics. For example, typical blood or apheresed peripheral blood mononuclear cell products have a helper T cell population ($T_H$, CD4+) that is greater than the cytotoxic or suppressor T cell population ($T_C$, CD8+). Ex vivo expansion of T cells by stimulating CD3 and CD28 receptors produces a population of T cells that prior to about days 8-9 consists predominately of $T_H$ cells, while after about days 8-9, the population of T cells comprises an increasingly greater population of $T_C$ cells. Accordingly, depending on the purpose of treatment, infusing a subject with a T cell population comprising predominately of $T_H$ cells may be advantageous. Similarly, if an antigen-specific subset of $T_C$ cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

Therapeutic Application

The present invention encompasses a cell (e.g., T cell) transduced with a lentiviral vector (LV). For example, the LV encodes a CAR that combines an antigen recognition domain of a specific antibody with an intracellular domain of CD3-zeta, CD28, 4-1BB, or any combinations thereof. Therefore, in some instances, the transduced T cell can elicit a CAR-mediated T-cell response.

The invention provides the use of a CAR to redirect the specificity of a primary T cell to a tumor antigen. Thus, the present invention also provides a method for stimulating a T cell-mediated immune response to a target cell population or tissue in a mammal comprising the step of administering to the mammal a T cell that expresses a CAR, wherein the CAR comprises a binding moiety that specifically interacts with a predetermined target, a zeta chain portion comprising for example the intracellular domain of human CD3zeta, and a costimulatory signaling region.

In one embodiment, the present invention includes a type of cellular therapy where T cells are genetically modified to express a CAR and the CAR T cell is infused to a recipient in need thereof. The infused cell is able to kill tumor cells in the recipient. Unlike antibody therapies, CAR T cells are able to replicate in vivo resulting in long-term persistence that can lead to sustained tumor control.

In one embodiment, the CAR T cells of the invention can undergo robust in vivo T cell expansion and can persist for an extended amount of time. In another embodiment, the CAR T cells of the invention evolve into specific memory T cells that can be reactivated to inhibit any additional tumor formation or growth. For example, it was unexpected that the CART19 cells of the invention can undergo robust in vivo T cell expansion and persist at high levels for an extended amount of time in blood and bone marrow and form specific memory T cells. Without wishing to be bound by any particular theory, CAR T cells may differentiate in vivo into a central memory-like state upon encounter and subsequent elimination of target cells expressing the surrogate antigen.

Without wishing to be bound by any particular theory, the anti-tumor immunity response elicited by the CAR-modified T cells may be an active or a passive immune response. In addition, the CAR mediated immune response may be part of an adoptive immunotherapy approach in which CAR-modified T cells induce an immune response specific to the antigen binding moiety in the CAR. For example, a CART19 cells elicits an immune response specific against cells expressing CD19.

While the data disclosed herein specifically disclose lentiviral vector comprising anti-CD19 scFv derived from FMC63 murine monoclonal antibody, human CD8α hinge and transmembrane domain, and human 4-1BB and CD3zeta signaling domains, the invention should be construed to include any number of variations for each of the components of the construct as described elsewhere herein. That is, the invention includes the use of any antigen binding moiety in the CAR to generate a CAR-mediated T-cell response specific to the antigen binding moiety. For example, the antigen binding moiety in the CAR of the invention can target a tumor antigen for the purposes of treat cancer.

Cancers that may be treated include tumors that are not vascularized, or not yet substantially vascularized, as well as vascularized tumors. The cancers may comprise non-solid tumors (such as hematological tumors, for example, leukemias and lymphomas) or may comprise solid tumors. Types of cancers to be treated with the CARs of the invention include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

Hematologic cancers are cancers of the blood or bone marrow. Examples of hematological (or hematogenous) cancers include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases).

In one embodiment, the antigen bind moiety portion of the CAR of the invention is designed to treat a particular cancer. For example, the CAR designed to target CD19 can be used to treat cancers and disorders including but are not limited to pre-B ALL (pediatric indication), adult ALL, mantle cell lymphoma, diffuse large B-cell lymphoma, salvage post allogeneic bone marrow transplantation, and the like. In another embodiment, the CAR can be designed to target CD22 to treat diffuse large B-cell lymphoma.

In one embodiment, cancers and disorders include but are not limited to pre-B ALL (pediatric indication), adult ALL, mantle cell lymphoma, diffuse large B-cell lymphoma, salvage post allogeneic bone marrow transplantation, and the like can be treated using a combination of CARs that target CD19, CD20, CD22, and ROR1.

In one embodiment, the CAR can be designed to target mesothelin to treat mesothelioma, pancreatic cancer, ovarian cancer, and the like. In another embodiment, the CAR can be designed to target CD33/IL3Ra to treat acute myelogenous leukemia and the like. In a further embodiment, the CAR can be designed to target cMet to treat triple negative breast cancer, non-small cell lung cancer, and the like.

In one embodiment, the CAR can be designed to target PSMA to treat prostate cancer and the like. In another embodiment, the CAR can be designed to target Glycolipid F77 to treat prostate cancer and the like. In a further embodiment, the CAR can be designed to target EGFRvIII to treat gliobastoma and the like.

In one embodiment, the CAR can be designed to target GD-2 to treat neuroblastoma, melanoma, and the like. In another embodiment, the CAR can be designed to target NY-ESO-1 TCR to treat myeloma, sarcoma, melanoma, and the like. In a further embodiment, the CAR can be designed to target MAGE A3 TCR to treat myeloma, sarcoma, melanoma, and the like.

However, the invention should not be construed to be limited to solely to the antigen targets and diseases disclosed herein. Rather, the invention should be construed to include any antigenic target that is associated with a disease where a CAR can be used to treat the disease.

The CAR-modified T cells of the invention may also serve as a type of vaccine for ex vivo immunization and/or in vivo therapy in a mammal. Preferably, the mammal is a human.

With respect to ex vivo immunization, at least one of the following occurs in vitro prior to administering the cell into a mammal: i) expansion of the cells, ii) introducing a nucleic acid encoding a CAR to the cells, and/or iii) cryopreservation of the cells.

Ex vivo procedures are well known in the art and are discussed more fully below. Briefly, cells are isolated from a mammal (preferably a human) and genetically modified (i.e., transduced or transfected in vitro) with a vector expressing a CAR disclosed herein. The CAR-modified cell can be administered to a mammalian recipient to provide a therapeutic benefit. The mammalian recipient may be a human and the CAR-modified cell can be autologous with respect to the recipient. Alternatively, the cells can be allogeneic, syngeneic or xenogeneic with respect to the recipient.

The procedure for ex vivo expansion of hematopoietic stem and progenitor cells is described in U.S. Pat. No. 5,199,942, incorporated herein by reference, can be applied to the cells of the present invention. Other suitable methods are known in the art, therefore the present invention is not limited to any particular method of ex vivo expansion of the cells. Briefly, ex vivo culture and expansion of T cells comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

In addition to using a cell-based vaccine in terms of ex vivo immunization, the present invention also provides compositions and methods for in vivo immunization to elicit an immune response directed against an antigen in a patient.

Generally, the cells activated and expanded as described herein may be utilized in the treatment and prevention of diseases that arise in individuals who are immunocompromised. In particular, the CAR-modified T cells of the invention are used in the treatment of CCL. In certain embodiments, the cells of the invention are used in the treatment of patients at risk for developing CCL. Thus, the present invention provides methods for the treatment or prevention of CCL comprising administering to a subject in need thereof, a therapeutically effective amount of the CAR-modified T cells of the invention.

The CAR-modified T cells of the present invention may be administered either alone, or as a pharmaceutical composition in combination with diluents and/or with other components such as IL-2 or other cytokines or cell populations. Briefly, pharmaceutical compositions of the present invention may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount," "an anti-tumor effective amount," "an tumor-inhibiting effective amount," or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, preferably $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments, it may be desired to administer activated T cells to a subject and then subsequently redraw blood (or have an apheresis performed), activate T cells therefrom according to the present invention, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocol may serve to select out certain populations of T cells.

The administration of the subject compositions may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i.v.) injection, or intraperitoneally. In one embodiment, the T cell compositions of the present invention are administered to a patient by intradermal or subcutaneous injection. In another embodiment, the T cell compositions of the present invention are preferably administered by i.v. injection. The compositions of T cells may be injected directly into a tumor, lymph node, or site of infection.

In certain embodiments of the present invention, cells activated and expanded using the CARs and methods described herein, or other methods known in the art where T cells are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1991; Henderson et al., Immun. 73:316-321, 1991; Bierer et al., Curr. Opin. Immun. 5:763-773, 1993). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAM-PATH. In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The dosage of the above treatments to be administered to a patient will vary with the precise nature of the condition being treated and the recipient of the treatment. The scaling of dosages for human administration can be performed according to art-accepted practices. The dose for CAM-PATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766).

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1

Constitutive CAR T Cell Proliferation

Adoptive immunotherapy has potent antitumor effects that are dependent on engraftment and proliferation of the transferred T cells in the host. The results presented herein demonstrate that certain chimeric antigen receptors (CARs) endow T cells with the ability to undergo long-term autonomous proliferation. Transduction of human T cells with second generation CARs encoding the CD28 and CD3ζ endodomains resulted in sustained proliferation for up to three months following a single stimulation through the TCR. This numeric expansion was independent of antigen stimulation and did not require the addition of exogenous cytokines or feeder cells. Both gene array and functional assays have identified that the prolonged growth is partially mediated by constitutive cytokine production. Microarray analysis identified a unique molecular signature of CAR T cells with the constitutive proliferative phenotype. Sustained expression of the endogenous IL-2 locus has not previously been reported in primary T cells. The CD28 and CD3 endodomains appear critical as constitutive signaling through NFkB, Akt, Erk and NFAT is observed. Further, not all CARs that signal through CD28 and CD3ζ could sustain ligand independent T-cell proliferation. The propagated CAR+ T cells retain a diverse TCR repertoire and transformation was not observed. The density of CAR expression at the cell surface is an important variable in determining whether the CAR has a constitutive or inducible growth phenotype. The identification of CAR designs that permit extensive T-cell proliferation without exogenous cytokine administration or feeder cells may have implications to either exploit or avoid CARs with constitutive activity.

The materials and methods used in this example are now described.

Materials and Methods

Construction of Lentiviral Vectors with Differing Eukaryotic Promoters and CARs

Figure 1A:
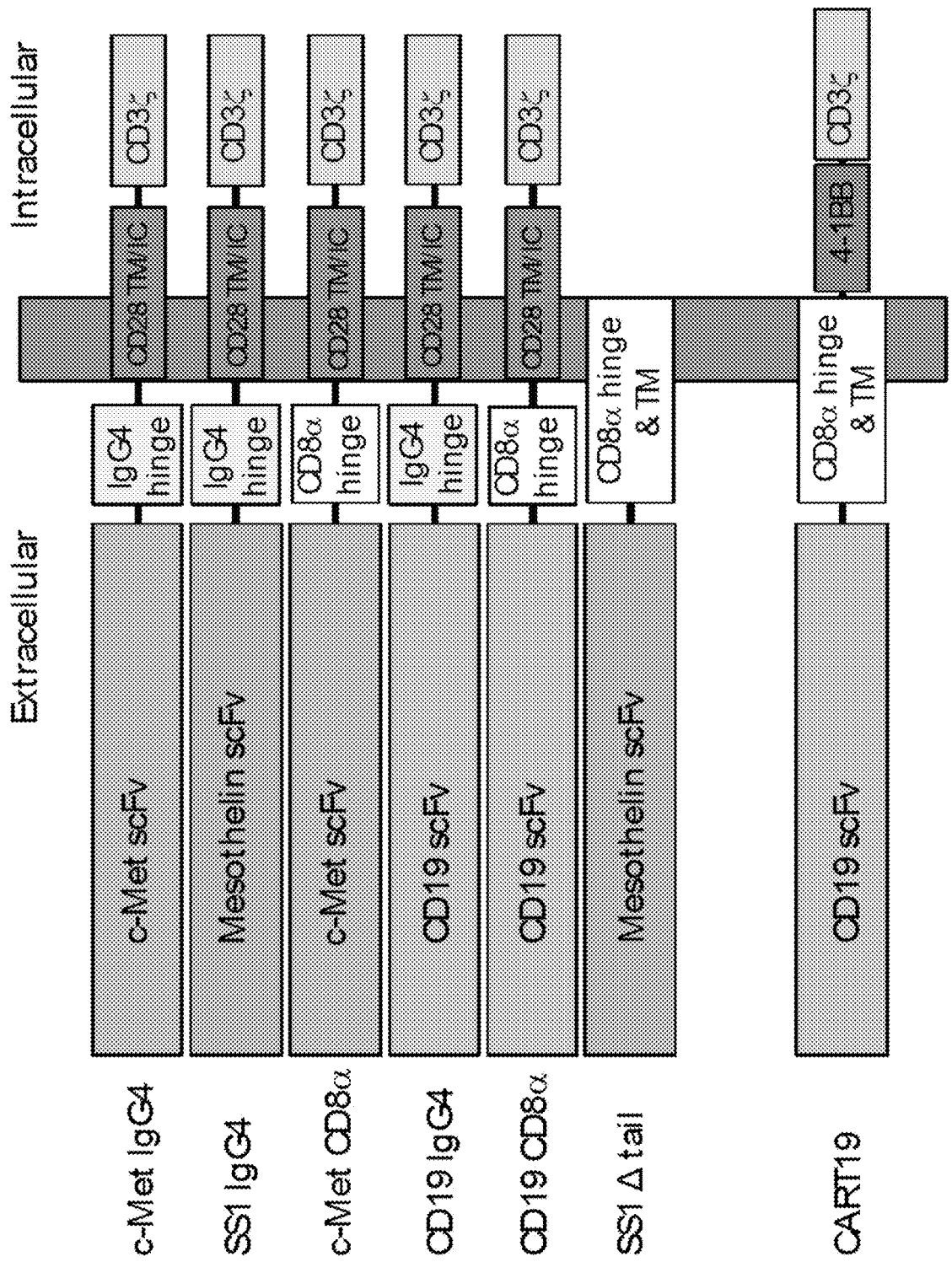
FIGS. 1A-1B are a series of images depicting chimeric antigen receptor constructs and relative expression levels.

FIG. 1A shows schematic diagrams of the CARs used in this study. All CARs contain a scFv that recognizes either the human CD19, mesothelin or c-Met antigen. Lentiviral vectors from previously published work were used to encode the anti-CD19 FMC63 CD8α (Tammana et al., 2010, Hum Gene Ther 21:75-86), the anti-mesothelin SS1 CD8α, and the anti-mesothelin SS1 CD8α Δtail CAR constructs (Carpenito et al., 2009, Proc Natl Acad Sci USA 106:3360-3365). The c-Met 5D5 IgG4 construct was used as a template to generate the SS1 IgG4 and CD19 IgG4 CAR constructs through PCR splicing and overlap extension. Restriction sites were introduced via PCR primers, which allowed for cloning into third generation self-inactivating lentiviral plasmids. The cytomegalovirus (CMV) and elongation factor-1α (EF-1α) promoter sequences were amplified via PCR from previously constructed plasmids and introduced into pre-existing CAR containing constructs (Milone et al., 2009, Mol Ther 17:1453-1464) using standard molecular biology techniques. Representative CARs are depicted below.

cMet IgG4 28z (SEQ ID NO: 1)

```
atgctgctgctggtgaccagcctgctgctgtgtgagctgccccacccccgc ctttctgctgatccccgacatccagatgacccagagccccagcagcgtga gcgccagcgtgggcgaccgggtgaccatcacctgccgggccagccagggc atcaacacctggctggcctggtatcagcagaagcccggcaaggcccccaa gctgagatctacgccgccagcagcctgaagagcggcgtgcccagccggtt tagcggctaggctaggcgccgacttcaccctgaccatcagcagcctgcag cccgaggacttcgccacctactactgccagcaggccaacagcttcccccct gacctttggcggcggaacaaaggtggagatcaagggcagcacctccggca
```

-continued gcggcaagcctggcagcggcgagggcagcaccaagggccaggtgcagagg tgcagagcggagccgaggtgaagaagcctggcgcctccgtcaaggtgtcc tgcgaggccagcggctacaccttcaccagctacggcttcagagggtgcgg caggcaccaggccaggcctcgaatggatgggctggatcagcgccagcaa cggcaacacctactacgcccagaagagcagggcagggtcaccatgaccac cgacaccagcaccagcagcgcctacatggaactgcggagcctgagaagcg acgacaccgccgtgtactactgcgccagggtgtacgccgactacgccgat tactggggccagggcaccaggtgaccgtgagcagcgagagcaagtacggc caccagcccccttgccagccccgagttcctgggcggacccagcgtgtt cctgttccccccaagcccaaggacaccctgatgatcagccggaccccg aggtgacctgtgtggtggtggacgtgtcccaggaggaccccgaggtccag ttcaactggtacgtggacggcgtggaggtgcacaacgccaagaccaagcc ccgggaggagcagttcaatagcacctaccgggtggtgtccgtgctgaccg tgctgcaccaggactggctgaacggcaaggaatacaagtgtaaggtgtcc aacaagggcctgcccagcagcatcgagaaaaccatcagcaaggccaaggg ccagcctcgggagccccaggtgtacaccagcccctagccaagaggagat gaccaagaaccaggtgtccctgacctgcctggtgaagggcttctacccca gcgacatcgccgtggagtgggagagcaacggccagcccgagaacaactac aagaccacccccctgtgctggacagcgacggcagcttcttcctgtacag ccggctgaccgtggacaagagccggtggcaggagggcaacgtattagctg accgtgatgcacgaggccagcacaaccactacacccagaagagcctgagc ctgtccctgggcaagatgttctgggtgctggtcgttgtgggcggcgtgct ggcctgctacagcctgctggtgacagtggccttcatcatcttttgggtga ggagcaagcggagcagactgctgcacagcgactacatgaacatgaccccc cggaggcctggccccacccggaagcactaccagccctacgcccctcccag ggatttcgccgcctaccggagccgggtgaagttcagccggagcgccgacg cccctgcctaccagcagggccagaaccagagtacaacgagctgaacctgg gccggagggaggagtacgacgtgctggacaagcggagagggccgggaccct gagatgggcggcaagccccggagaaagaaccccaggagggcctgtataa cgaactgcagaaagacaagatggccgaggcctacagcgagatcggcatga agggcgagcggaggcggggcaagggccacgacggcctgtaccagggcctg agcaccgccaccaaggataccctacgacgccagcacatgcaggccagcccc ccagatga SS1 IgG4 28z (SEQ ID NO: 2)

atggccttaccagtgaccgccttgacctgccgctggccttgctgaccacg ccgccaggccgggatcccaggtacaactgcagcagtagggcctgagagga gaagcctggcgcttcagtgaagatatcctgcaaggcttctggttactcat tcactggctacaccatgaactgggtgaagcagagccatggaaagagcctt gagtggattggacttattactccttacaatggtgcttctagctacaacca gaagttcaggggcaaggccacattaactgtagacaagtcatccagcacag -continued cctacatggacctcctcagtagacatctgaagactctgcagtctatttct gtgcaaggggggttacgacgggaggggttttgactactggggccaaggg accacggtcaccgtctcctcaggtggaggcggttcaggcggcggtggctc tagcggtggtggatcggacatcgagctcactcagtctccagcaatcatgt ctgcatctccaggggagaaggtcaccatgacctgcagtgccagctcaagt gtaagttacatgcactggtaccagcagaagtcaggcacctcccccaaaag atggatttatgacacatccaaactggcttctggagtcccaggtcgcttca gtggcagtgggtctgggaaactcttactctctcacaatcagcagcgtggag gctgaagatgatgcaacttattactgccagcagtggagtaagcaccctct cacgtacggtgctgggacaaagttggaaatcaaaagcagcgagagcaagt acggccctcccctgcccccttgccctgccccgagttcctgggcggaccc agcgtgttcctgttccccccaagcccaaggacaccctgatgatcagccg gaccccgaggtgacctgtgtggtggtggacgtgtcccaggaggaccccg aggtccagttcaactggtacgtggacggcgtggaggtgcacaacgccaag accaagccccgggaggagcagttcaatagcacctaccgggtggtgtccgt gctgaccgtgctgcaccaggactggctgaacggcaaggaatacaagtgta aggtgtccaacaagggcctgcccagcagcatcgagaaaaccatcagcaag gccaagggccagcctcgggagccccaggtgtacaccctgcccccagcca agaggagatgaccaagaaccaggtgtccctgacctgcctggtgaagggat ctaccccagcgacatcgccgtggagtgggagagcaacggccagcccgaga acaactacaagaccacccccctgtgctggacagcgacggcagcttatcc tgtacagccggctgaccgtggacaagagccggtggcaggagggcaacgtc tttagctgctccgtgatgcacgaggccctgcacaaccactacacccagaa gagcctgagcctgtccctgggcaagatgttctgggtgctggtcgttgtgg gcggcgtgctggcctgctacagcctgctggtgacagtggccttcatcatc ttttgggtgaggagcaagcggagcagactgctgcacagcgactacatgaa catgaccccccggaggcctggccccacccggaagcactaccagccctacg cccctcccagggatttcgccgcctaccggagccgggtgaagttcagccgg agcgccgacgcccctgcctaccagcagggccagaaccagctgtacaacga gctgaacctgggccggagggaggagtacgacgtgctggacaagcggagag gccgggaccctgagatgggcggcaagccccggagaaagaaccccaggag ggcctgtataacgaactgcagaaagacaagatggccgaggcctacagcga gatcggcatgaagggcgagcggaggcggggcaagggccacgacggcctgt accagggcctgagcaccgccaccaaggatacctacgacgccctgcacatg caggccctgccccccagatga CD19 IgG4 28z (SEQ ID NO: 3)

atggccttaccagtgaccgccttgctcctgccgctggccttgctgctcca cgccgcaggccgacatccagatgacacagactacatcctccctgtctg cctctctgggagacagagtcaccatcagttgcagggcaagtcaggacatt agtaaatatttaaattggtatcagcagaaaccagatggaactgttaaact cctgatctaccatacatcaagattacactcaggagtcccatcaaggttca -continued

```
gtggcagtgggtctggaacagattattctctcaccattagcaacctggag caagaagatattgccacttacttttgccaacagggtaatacgcttccgta cacgttcggagggggaccaagctggagatcacaggtggcggtggctcgg gcggtggtgggtcgggtggcggcggatctgaggtgaaactgcaggagtca ggacctggcctggtggcgccctcacagagcctgtccgtcacatgcactgt ctcagggtctcattacccgactatggtgtaagctggattcgccagcctc cacgaaagggtctggagtggctgggagtaatatggggtagtgaaaccaca tactataattcagctctcaaatccagactgaccatcatcaaggacaactc caagagccaagtttttcttaaaaatgaacagtctgcaaactgatgacacag ccatttactactgtgccaaacattattactacggtggtagctatgctatg gactactggggccaaggaacctcagtcaccgtctcctcaagcagcgagag caagtacggccctccctgccccccttgccctgccccgagttcctgggcg gacccagcgtgttcctgttcccccccaagcccaaggacacctgatgatc agccggaccccgaggtgacctgtgtggtggtggacgtgtcccaggagga ccccgaggtccagttcaactggtacgtggacggcgtggaggtgcacaacg ccaagaccaagcccgggaggagcagttcaatagcacctaccgggtggtg tccgtgctgaccgtgctgcaccaggactggctgaacggcaaggaatacaa gtgtaaggtgtccaacaagggcctgcccagcagcatcgagaaaaccatca gcaaggccaagggccagcctcgggagcccaggtgtacaccctgccccct agccaagaggagatgaccaagaaccaggtgtccctgacctgcctggtgaa gggcttctaccccagcgacatcgccgtggagtgggagagcaacgccagc ccgagaacaactacaagaccacccccctgtgctggacagcgacggcagc ttcttcctgtacagccggctgaccgtggacaagagccggtggcaggaggg caacgtctttagctgctccgtgatgcacgaggccctgcacaaccactaca cccagaagagcctgagcctgtccctgggcaagatgttctgggtgctggtc gttgtgggcggcgtgctggcctgctacagcctgctggtgacagtggccttt catcatcttttgggtgaggagcaagcggagcagactgctgcacagcgact acatgaacatgacccccggaggcctggccccacccggaagcactaccag ccctacgcccctcccagggatttcgccgcctaccggagccgggtgaagtt cagccggagcgccgacgccctgcctaccagcagggccagaaccagctgt acaacgagctgaacctgggccggagggaggagtacgacgtgctggacaag cggagaggccgggaccctgagatgggcggcaagcccggagaagaaccc ccaggagggcctgtataacgaactgcagaaagacaagatggccgaggcct acagcgagatcggcatgaagggcgagcggaggcggggcaagggccacgac ggcctgtaccagggcctgagcaccgccaccaaggatacctacgacgccct gcacatgcaggccctgccccccagatga
```

Microarray Studies

Sample Collection. Human CD4+ T cells from three normal donors were stimulated and transduced with either the c-Met IgG4 or CD19 CD8α CAR construct. Cell pellets were collected and frozen on day 0 prior to stimulation, day 6 and day 11 at rest down for all samples and 24 for the c-Met IgG4 CAR.

Microarray Target Preparation and Hybridization. Microarray services were provided by the UPenn Microarray Facility, including quality control tests of the total RNA samples by Agilent Bioanalyzer and Nanodrop spectrophotometry. All protocols were conducted as described in the Affymetrix GeneChip Expression Analysis Technical Manual. Briefly, 100 ng of total RNA was converted to first-strand cDNA using reverse transcriptase primed by poly(T) and random oligomers that incorporated the T7 promoter sequence. Second-strand cDNA synthesis was followed by in vitro transcription with T7 RNA polymerase for linear amplification of each transcript, and the resulting cRNA was converted to cDNA, fragmented, assessed by Bioanalyzer, and biotinylated by terminal transferase end labeling. cRNA yields ranged from 36-89 µg, and cDNA was added to Affymetrix hybridization cocktails, heated at 99° C. for 5 min and hybridized for 16 h at 45° C. to Human Gene 1.0ST GeneChips (Affymetrix Inc., Santa Clara, Calif.). The microarrays were then washed at low (6×SSPE) and high (100 mM MES, 0.1M NaCl) stringency and stained with streptavidin-phycoerythrin. A confocal scanner was used to collect fluorescence signal after excitation at 570 nm.

Initial Data Analysis. Affymetrix Command Console and Expression Console were used to quantify expression levels for targeted genes; default values provided by Affymetrix were applied to all analysis parameters. Border pixels were removed, and the average intensity of pixels within the 75th percentile was computed for each probe. The average of the lowest 2% of probe intensities occurring in each of 16 microarray sectors was set as background and subtracted from all features in that sector. Probe sets for positive and negative controls were examined in Expression Console, and Facility quality control parameters were confirmed to fall within normal ranges. Probes for each targeted gene were averaged and inter-array normalization performed using the RMA algorithm.

Analysis of Terminal Telomeric Restriction Fragment Lengths

Telomeric restriction fragment length analysis was performed essentially as described (Lukens et al., 2009, Alzheimers Dement 5:463-469). Briefly, 2 µg of genomic DNA was digested with RsaI+HinfI and resolved on a 0.5% agarose gel, which was then dried and probed with a $^{32}$P-labeled (CCCTAA) 4 oligonucleotide. After washing, the samples were visualized with a Phosphor imager.

Statistical Analysis

Raw data obtained from microarray core was normalized with robust multichip average (RMA). Analysis was performed using a 3-way mixed model ANOVA with factors being sample date, treatment group and donor ID. An interaction term between sample and collection date was added. In conjunction with the multiple pair wise contrasts that were looked at a p-value and fold change were determined. For all p-values we calculated the FDR corrected p-value using the method of Benjamin and Hochberg as implemented by Partek Genomic Suite (Partek). For transcription factor and cytokine dot plots the normalized absolute log(2) gene expression intensities were plotted. Cluster analysis was performed using Euclidean distance of median normalized log(2) gene expression intensities with average linkage. All growth curves, MFI and engraftment plots were plotted using Prism (GraphPad Software). All error bars are representative of standard deviation. A two tailed Mann-Whitney test was performed for the in vivo engraftment studies.

Cell Lines and Culture

Blood samples were obtained from the Human Immunology Core of the University of Pennsylvania where peripheral blood CD4+ T cells were negatively isolated using RosetteSep Kits (Stem cell Technologies). Cells were cultured in R10 (RPMI 1640 media supplemented with 10% FCS, 100-U/ml penicillin, 100 μg/ml streptomycin sulfate, 10 mM Hepes) in a 37° C. and 5% $CO_2$ incubator. For stimulation, CD4+ T cells were cultured with activating beads coated with antibodies to CD3 and CD28 at a 1:3 cell to bead ratio. Cells were transduced with lentiviral vectors containing CAR constructs approximately 24 hrs following stimulation. T cells were monitored, kept at a concentration of 0.75×$10^6$/mL and were considered rested when MCV<175. The M30 and NCI-H522 tumor lines were used in cell killing assays. The M30 cell line (Crisanti et al., 2009, Mol Cancer Ther 8:2221-2231) is a mesothelial tumor derived at the University of Pennsylvania from mesothelioma tumor tissues from individual patients and was cultured in E-media (10% FDCS, 1X ITES, 10 m HEPES, 0.5 mM Na Pyruvate, 0.1 mMMEM NEAAs, 100 ug/mL Pen/Strep, 1 ng/mL EGF, 18 ng/mL HC, 0.1 nM T3 in RPMI) while the NCI-H522 (adenocarcinoma) was obtained from the National Cancer Institute and cultured in R10. Jurkat cell line stably transfected with a plasmid containing d2EGFP under the control of a minimal promoter bearing the NFAT consensus binding sequence (pNFAT-d2EGFP) was kindly provided by Arthur Weiss (University of California at San Francisco).

Flow Cytometry and Antibodies

CAR surface staining was performed in FACS buffer (PBS with 3% fetal calf serum) using biotin conjugated polyclonal antibody (Jackson ImmunoResearch). Rabbit anti-human IgG (H+L) was used for cMet IgG4, SS1 IgG4, and CD19 IgG4, while goat anti-mouse (Fab')2 was used as primary for SS1 CD8α, CD19 CD8α, and SS1 Δtail. Secondary stain for CAR was done using streptavadin-APCeFluor780 (eBioscience). Cell surface marker analysis was done using CD25 PerCp-Cy5.5 (eBioscience, clone BC96), CD70 PE (BD, clone Ki-24), PD-1 PerCP-eFluor710 (eBioscience, clone J105), CD45RO eFluor450 (eBioscience, clone UCHL1), CD27 v450 (BD, clone M-T271), CD28 FITC (eBioscience, clone CD28.2), CD62L PE (eBioscience, clone DREG-56), CCR7 FITC (BD, clone 150503), Crtam APC (Biolegend, clone Cr24.1) and c-Met PE (R&D systems, clone 95106) at the recommended concentrations. c-Met antigen staining was done using monoclonal anti-human HGF R/c-MET-PE (R&D, clone #95106), and mesothelin expression was analyzed with primary monoclonal mouse anti-human CAK1 (Covance) at 1:50 followed by polyclonal goat anti-mouse PE (BD) at 1:100. Samples were analyzed on a LSR II (BD) and analyzed with FlowJo software (TreeStar).

PhosFlow was performed on days 6, 10 and 25. Cells were fixed using BD cytofix buffer (BD) for 10 min at 37C followed by permeabilization using BD Phosflow Perm Buffer III (BD) at 4C for 30 minutes. Cells were stained at RT for 30 min in the dark using PE anti-Erk1/2 (pT202/pY204) (BD, clone 20A), PE conjugated anti-Akt (pS473) (BD, clone M89-61), PE conjugated anti-NF-kB p65 (pS529) (BD, clone K10-895.12.50), or PE conjugated anti-S6 (pS235/pS236) (BD, clone N7-548) at manufactures recommended concentrations. Positive controls were samples from each group stimulated for 10 min using PMA/Ionomycin prior to fixation, while negative controls were fully stimulated T cells stained using PE conjugated IgG2b kappa isotype control (BD, clone 27-35). Samples were run on a LSR II (BD Bio-sciences) and analyzed with FlowJo software (TreeStar).

Cytokine Measurements

CD4+ T cells were transduced with CAR constructs as described elsewhere herein. On days 6, 10, and 30 one million cells were taken from each group, pelleted, washed in R10 and plated at 1×10^6/mL in fresh media. At 24 hrs supernatant was collected and frozen at −80° C. Quantification of soluble cytokine factors was performed using Luminex bead array technology and kits purchased from Life Technologies (Invitrogen 30-plex). Assays were performed as per the manufacturer protocol with 9-point standard curve generated using a 3-fold dilution series and according to laboratory SOP. Each sample was evaluated in duplicate at 1:3 dilution; calculated % CV for the duplicate measures was in most cases less than 5% and always less than 15%. Data were acquired on a FlexMAP-3D and analyzed using XPonent 4.0 software and 5-parameter logistic regression analysis. Standard curve quantification ranges were determined by the 80-120% (observed/expected value) range.

Conditioned Media Transfer

Supernatant from c-Met IgG4 transduced. T cell cultures was collected on day 56, filtered through a 70 μm filter and frozen at −80° C. in 10 mL aliquots. Day 56 media was thawed and added to unstimulated naïve CD4+ T cells in culture to reach a final concentration of 12.5%, 25%, and 50% c-Met IgG4 supernatant relative to starting media. As controls, media with and without 100115 of IL-2 was also included, as well as CD3/CD28 bead stimulated cells kept in culture with initial stimulation on day 0 and re-stimulation on day 12. Mean cell volumes were determined and cell media was readjusted every two days to maintain IL-2 concentration within control group and appropriate c-Met IgG4 media transfer ratio described elsewhere herein.

Vβ Diversity Determination

CD4+ human T cells were isolated, stimulated and transduced with c-Met IgG4 CAR as described elsewhere herein. Donor matched untransduced cells were stimulated and expanded simultaneously as control. Untransduced controls required two additional bead stimulations to maintain in culture. Cells were cryopreserved at D0, D13 and D34. Cells were thawed simultaneously and allowed to rest overnight. TCR Vβ analysis was performed using the IOTest Beta Mark TCR V kit (Beckman Coulter) which contains directly-conjugated antibodies specific for the following VP families: 1, 2, 3, 4, 5.1, 5.2, 5.3, 7.1, 7.2, 8, 9, 11, 12, 13.1, 13.2, 13.6, 14, 16, 17, 18, 20, 21.3, 22, and 23. Samples were run on a LSR II (BD) with subsequent analysis in FlowJo (TreeStar) to determine percent of total population.

Cytotoxicity Assay

A mix of CD4+ and CD8+ human T cells electroporated with mRNA encoding the indicated CAR were used for in vitro killing. CD19 CD8α and c-Met IgG4 CARs were subcloned into a pGEM.64A-based vector previously described (Zhao et al., 2006, Mol Ther 13:151-159). The SS1 CD8α CAR mRNA was made as described (Zhao et al., 2010, Cancer Res 70:9062-9072). The replaced CAR cDNAs were confirmed by direct sequencing and linearized by SpeI digestion prior to RNA IVT. mScript RNA System (Epicentre, Madison, Wis.) was used to generate capped IVT RNA. The IVT RNA was purified using an RNeasy Mini Kit (Qiagen, Inc., Valencia, Calif.), and purified RNA was eluted in RNase-free water at 1-2 mg/ml. Human T cells were stimulated by CD3/CD28 beads as described (Carpenito et al., 2009, Proc Natl Acad Sci USA 106:3360-3365). On day 0 the stimulated T cells were washed three times with Opti-MEM and resuspended in Opti-MEM at the final concentration of 1-3 ×10$^8$/ml prior to electroporation. Subsequently, the stimulated T cells were mixed with 10 μg/0.1 ml of IVT RNA (as indicated) and electroporated in a 2-mm cuvette (Harvard Apparatus BTX, Holliston, Mass.) using an ECM830 Electro Square Wave Porator (Harvard Apparatus BTX). Tumor lines were then harvested with trypsin and plated in a 6 well dish at 0.2×10^6/mL. 24 hours post T cell electroporation and tumor plating T cells were combined with target cells at increasing effector:target (E:T) ratios in a 6 well plate as well, alongside a no T cell control. Cells were incubated at 37° C. for 18 hrs. Cells were collected after incubation, wells were re-trypsinized and washed repeatedly to collect all tumor and T cells. Cells mixtures were stained for tumor with anti-EpCAM (BD, clone EBA-1), T cells with anti-CD45 (BD, clone 2D1), and with 7-AAD (Invitrogen). Cells were resuspended in 400 uL FACS buffer containing counting beads (Invitrogen) to normalize data acquisition across samples. Samples were then filtered through a 35 μm filter (BD Falcon) and put on ice for analysis. Cells were run on a LSR II (BD) and collection was performed by collecting 1500 bead events for all samples. Analysis was performed by gating on EpCAM (+), CD45(−), and 7-AAD(−) cells in FlowJo (TreeStar). Percent lysis was calculated by dividing total live cells in no T cell control group, by each experimental condition of increasing E:T ratio.

In Vivo T Cell Persistence Experiments

All animal experiments were approved by the University of Pennsylvania Institutional Animal Care and Use Committee. NSG mice (NOD.Cg-Prkdc$^{scid}$Il2$^{tmlWjl}$/SzJ) were used for engraftment and persistence experiments. The mice were housed under specific pathogen-free conditions in microisolator cages and given unrestricted access to autoclaved food and acidified water. Animals of both sexes were used for experiments at approximately 20 weeks of age. Human CD4+ T cells were isolated, stimulated and transduced as previously described. A total of 10×10$^6$ cells/mouse were injected peripherally by tail vein injections of which 50% were CAR (+) in the c-Met IgG4 group. Peripheral bleeds were done after 60 days and TruCounts (BD) were done using anti-human CD45 APC-H7 staining for absolute quantification. Samples were analyzed on a LSR II (BD Bioscience) and quantification was performed using FlowJo (TreeStar).

DNA Isolation and Q-PCR Analysis

Q-RT/PCR analysis: RNA was isolated from cell lines using RNAqueous RNA isolation kits (Ambion), and cDNA synthesized using iScript cDNA synthesis kits (Bio-Rad). Samples were analyzed for expression of c-met, mesothelin, and PP1B (housekeeping transcript) using ABI Taqman-based technologies and the following ABI recommended gene specific primer probe sets which span exon/intron boundaries: c-met: Hs01565584_m1*; mesothelin: HS00245879_m1*, and PP1B: Hs00168719_m1*. All amplification reactions were performed using an ABI 7500 FAST instrument (ABI-Life technologies), and established laboratory protocols. Each transcript was evaluated in triplicate. Ct values for each amplification reaction were determined using pre-established assay-specific threshold values, with a minimum of ⅔ replicates with % CV<15% required to record a Ct value. Average Ct values were calculated and reported. RQ (relative quantification) values for each transcript was determined according to the formula: RQ=2−−ΔCt, with −ΔCt=−ΔCtsample−−ΔCtreference, with −ΔCtsample=Ctsample−Ctsample normalizer and −ΔCtreference=Ctreference−Ctreference normalizer (Pfaffl, 2001, Nucleic Acids Res 29(9):e45). For all analyses, the ovarian carcinoma cell line OV79 (positive for both MAGE-A3) served as the reference sample. The ovarian carcinoma-derived cell line OV-79 has been previously described (Bertozzi et al., 2006, In Vitro Cell Dev Biol Anim 42(3-4):58-62).

The results of this experimental example are now described.

Construction and Characterization of Chimeric Antigen Receptors

Figure 1B:
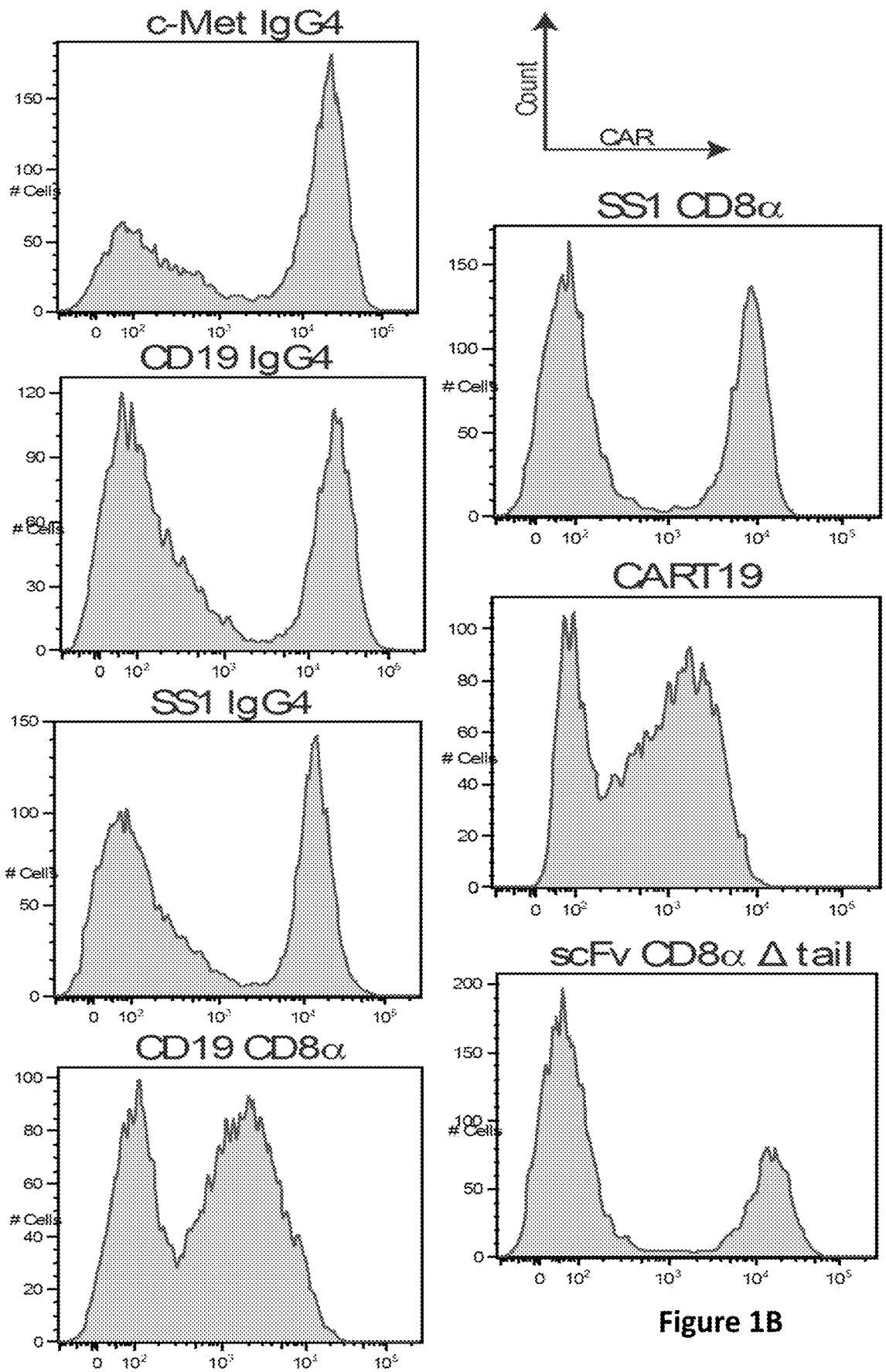
Figure 8:
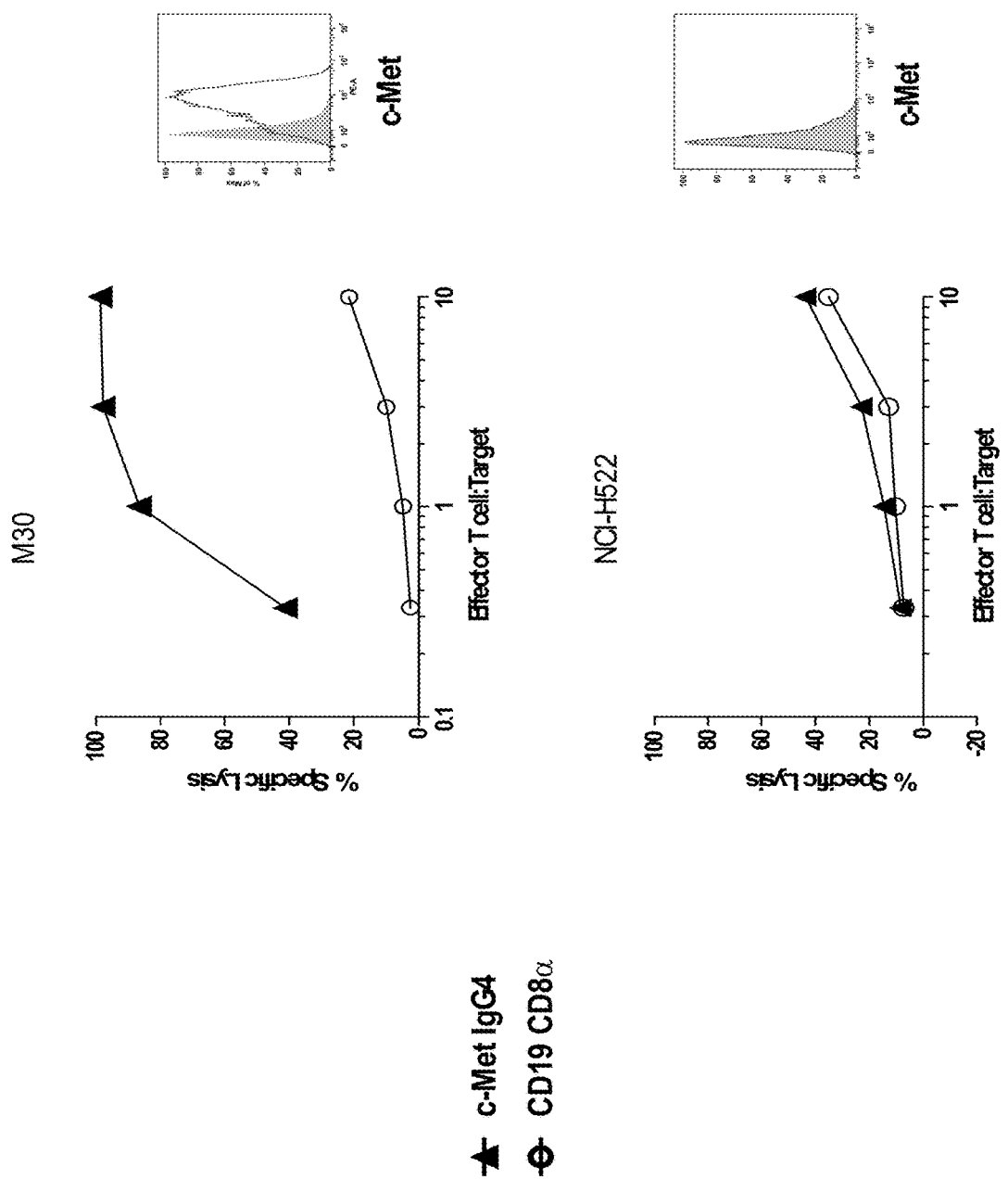
FIG. 8 is an image showing CAR T cells with constitutive proliferation retain specific cytotoxicity. The M30 tumor line (endogenous expression of c-Met), and the NCI-H522 tumor line (lacking c-Met expression) were cultured at the indicated effector to target ratio with c-Met IgG4 CAR T cells. CD19 CD8α CAR T cells were used as specificity controls to exclude allogeneic effects. Inset boxes: c-Met expression on M108 and NCI-H522.

A plethora of CARs have been generated that express CD28 and CD3ζ downstream of antibody fragments that mediate surrogate antigen recognition (Geiger et al., 2001, Blood 98:2364-2371; Arakawa et al., 2002, Anticancer Research 4285-4289; Haynes et al., 2002, J Immunol 169 (10):5780-6; Maher et al., 2002, Nature Biotechnology 20:70-75; Finney et al, 2004, J Immunol 172:104-113; Gyobu et al., 2004, Cancer Res 64:1490-1495; Moeller et al., 2004, Cancer Gene Ther 11:371-379; Teng et al., 2004, Hum Gene Ther 15:699-708; Friedmann-Morvinski et al., 2005, Blood 105:3087-3093; Pule et al., 2005, Molecular Therapy 12:933-941; Westwood et al., 2005, Proc Natl Acad Sci USA 102:19051-19056; Willemsen et al., 2005, J Immunol 174:7853-7858; Kowolik et al, 2006, Cancer Res 66:10995-11004; Loskog et al., 2006, Leukemia 20:1819-1828; Shibaguchi et al., 2006, Anticancer Res 26:4067-4072; Teng et al., 2006, Human Gene Therapy 17:1134-1143; Brentjens et al., 2007, Clin Cancer Res 13:5426-5435). Given that these transgenes were constructed differently and by different investigators at different institutes, it remains unknown how these CARs would perform with a common expression system and a standardized culture system that has been optimized for clinical use. Therefore, a set of CARs targeting c-Met, mesothelin and CD19 was expressed in primary human CD4+ T cells (FIG. 1A). The CARs encoded IgG4 or CD8α hinge domains, CD28 or CD8α transmembrane domains and the signaling domains were comprised of CD28 and CD3ζ. A CAR with a truncated signaling domain, and a CD19 4-1BB:CD3ζ CAR used in a previous clinical trial (Porter et al., 2011, N Engl J Med 365:725-733) served as controls. All CARs were expressed constitutively using an EF-1α promoter, and in a typical experiment 50% of the cells initially expressed the CAR and had similar levels of expression on the surface by day 6 after transduction (FIG. 1B). The c-Met CAR T cells had specific and potent cytotoxicity (FIG. 8), and previous studies have shown that the CARs specific for CD19 and mesothelin have similarly potent effector functions (Carpenito et al., 2009, Proc Natl Acad Sci USA 106:3360-3365; Milone et al., 2009, Mol Ther 17:1453-1464).

Figure 2A:
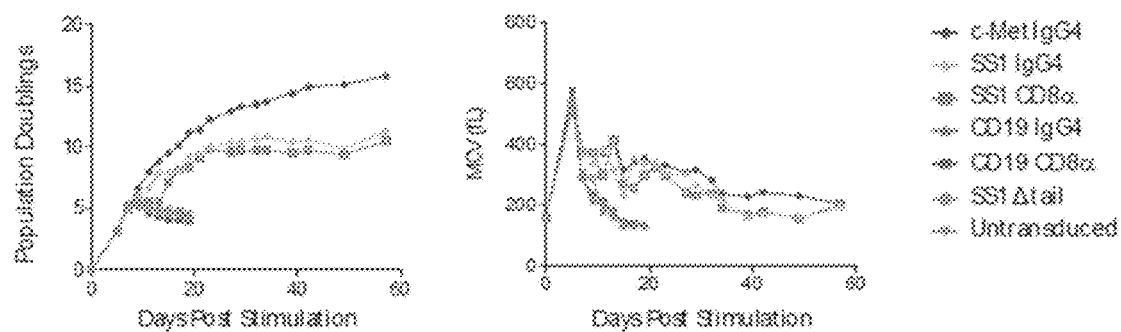
FIGS. 2A-2D are a series of images depicting induction of constitutive, ligand independent CD4 CAR T cell proliferation.
Figure 2B:
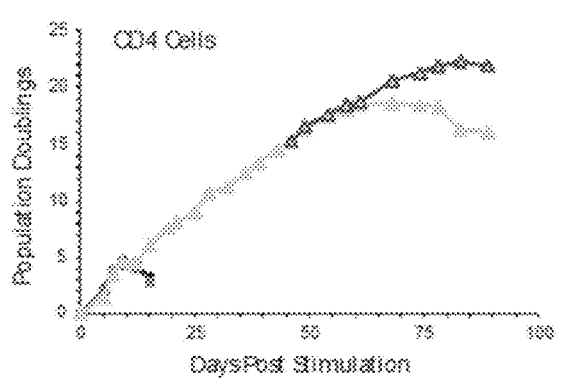
Figure 2C:
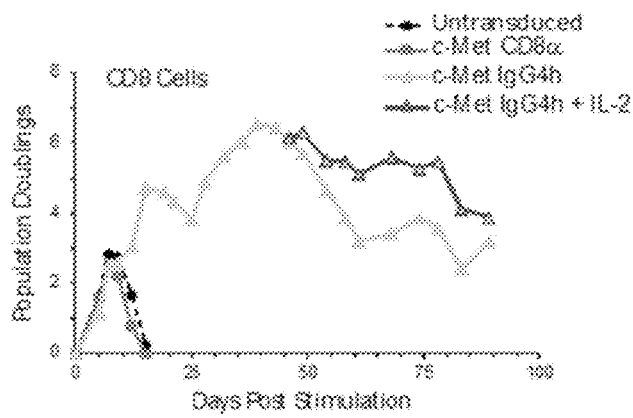
Figure 2D:
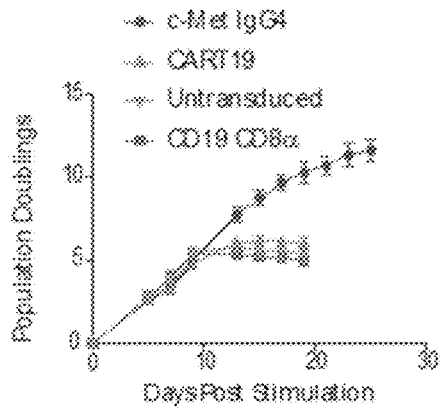

Chimeric Antigen Receptors with CD28 and CD3 can Induce Constitutive T Cell Proliferation Previous studies suggested that antitumor effects after CAR T cell infusions require sustained expansion of CAR T cells in vivo after adoptive transfer (Kalos et al., 2011, Sci Transl Med 3:95ra73). To determine the proliferative capacity of the CAR T cells, CD4+ T cells were activated with anti-CD3 and CD28 beads, transduced with the lentiviral vector encoding the CAR and then propagated without further stimulation in the absence of exogenous cytokines or feeder cells. Unexpectedly, constitutive proliferation of some of the CAR T cell populations was observed (FIG. 2A, left). Exponential growth was observed for 60 to 90 days in CAR T cells transduced with the c-Met IgG4 construct that encoded CD28 and CD3ζ signaling domains (FIGS. 2A and 2B). Similarly, the T cells expressing the anti-mesothelin SS1:IgG4 and SS1:CD8α CARs that signaled through chimeric CD28 and CD3ζ domains also had sustained proliferation that was independent of supplementation with exogenous growth factors. Long-term proliferation of CD8+ T cells that was independent of antigen stimulation and did not require the addition of exogenous cytokines or feeder cells was also observed (FIG. 2C). However, in order to minimize experimental variables, the rest of the experiments in this study were carried using bulk CD4+ T cells.

In contrast, the cultures with the other CAR T cell populations had an initial period of exponential proliferation at the same rate, and after day 10, a decreasing rate of growth followed by death of the culture within 20 days (FIGS. 2A and 2B). For simplicity and clarity the CAR constructs that induce constitutive proliferation are henceforth referred to as "continuous CARs", while the CARs that exhibit inducible proliferation similar to previous reports are referred to as "classic CARs".

Figure 9:
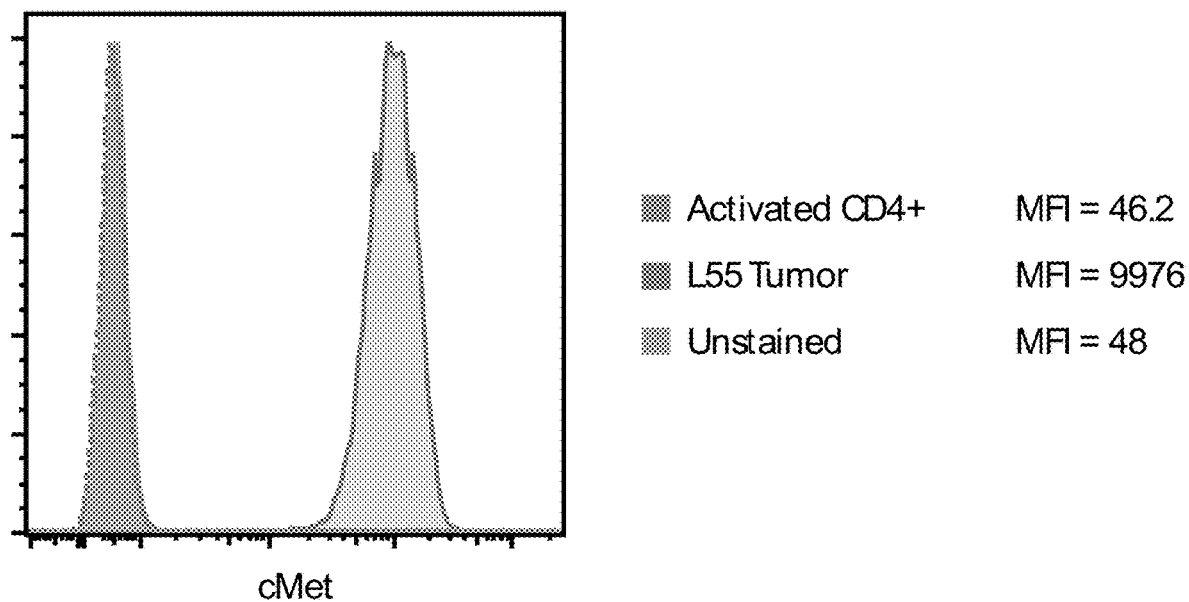
FIG. 9 is an image demonstrating that c-Met and mesothelin expression is not detected on human CD4+ T cells. CD4+ T cells do not express detectable levels of c-Met or mesothelin. Samples were compared to L55, a non-small cell lung tumor cell line, as well as unstained CD4+ T cells. Following activation, human CD4+ T cells and tumor lines were stained for c-Met (PE) or mesothelin (PE). Histograms depict unstained activated CD4+ T cells, activated CD4+ T cells, and the L55 tumor stained for described antigen. The mean fluorescence intensity is indicated.
Figure 9:
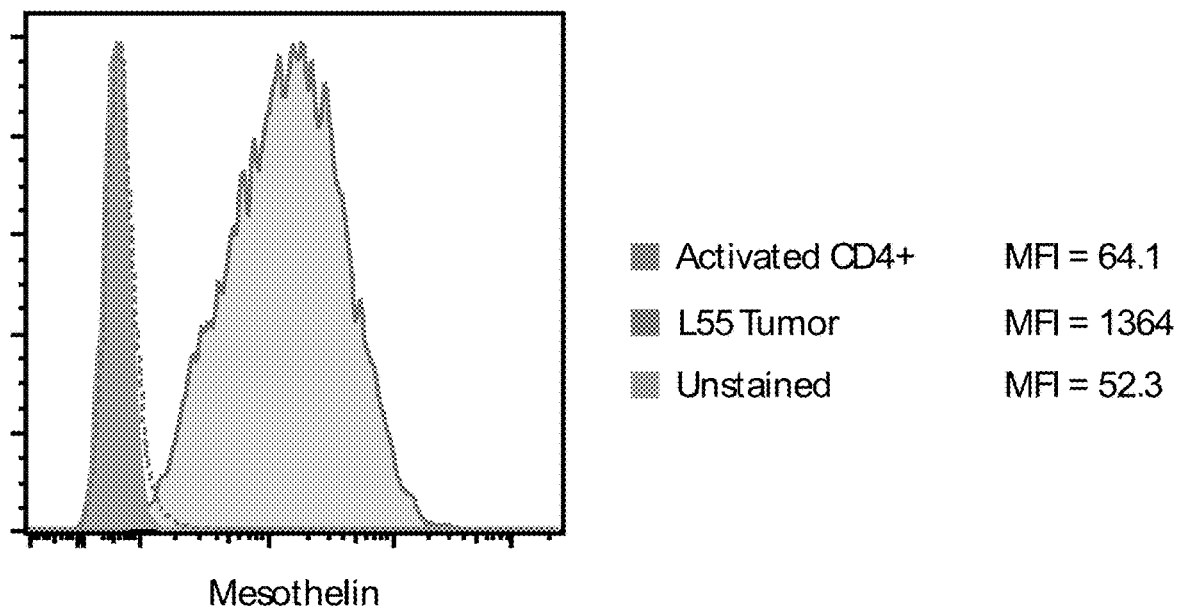

The mean cell volumes were monitored at frequent intervals as a measure of metabolic status and cell cycle (FIG. 2A, right). All T cell cultures transduced with the various CAR constructs increased from a resting (G0) cell volume of ~190 fl to nearly 600 fl by day 6 of culture, consistent with the induction of DNA synthesis and the exponential increase in cell numbers. However, the classic CAR T cells and non-transduced T cells rapidly returned to a resting cell volume, while the continuous CAR T cells (c-Met IgG4, SS1 IgG4 and SS1 CD8α) failed to return to a resting cell volume, consistent with the continued cellular proliferation. On day 20 of culture, the mean cell volume in the cultures of continuous CARs and classic CARs was ~400 fl and 180 fl, respectively. Notably, the long term proliferation of the CAR T cells was ligand independent, because the surrogate ligands cMet and mesothelin are not expressed at detectable levels on the surface of activated human CD4+ T cells (FIG. 9), consistent with previous reports (Skibinski et al., 2001, Immunology 102:506-514). Q-PCR analysis did not detect transcripts for mesothelin or c-Met in resting CD4 T cells. However, activated T cells, either mock transduced or transduced with a continuous CAR and cultured under the conditions that lead to long term growth expressed very low but detectable transcripts specific for c-Met, while mesothelin transcripts remained undetectable. Given that both c-Met and mesothlelin-specific CARs displayed the continuous growth phenotype, the low level of c-Met expression in activated T cells is unlikely to be necessary for the sustained growth of the T cells. In addition, the absence of fratricide in the cultures is consistent with ligand-independent continuous growth.

Figure 10:
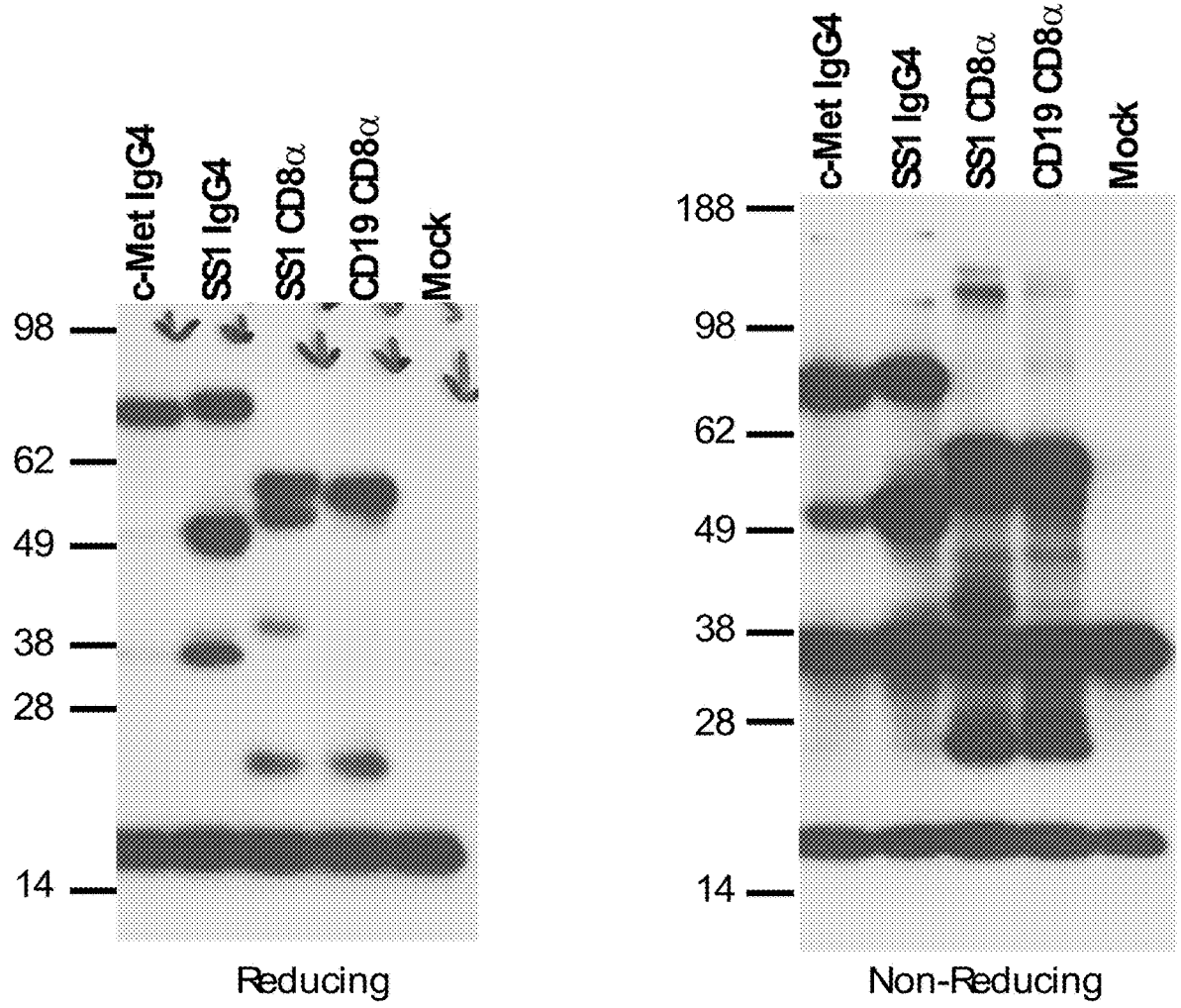
FIG. 10 is an image of a Western blot analysis of CARs with constitutive or inducible proliferative phenotype. Western blot was performed under reducing and non-reducing conditions probing for CD3ζ using mouse anti-human CD3ζ at 0.250ug/mL followed by anti-mouse HRP at 1:5000 on lysates from day 8 post transduction samples. CAR monomers (50 to 70 kD) under reducing conditions (left) and dimers and monomers under non-reducing conditions (right). Endogenous CD3ζ as internal loading control.
Figure 11:
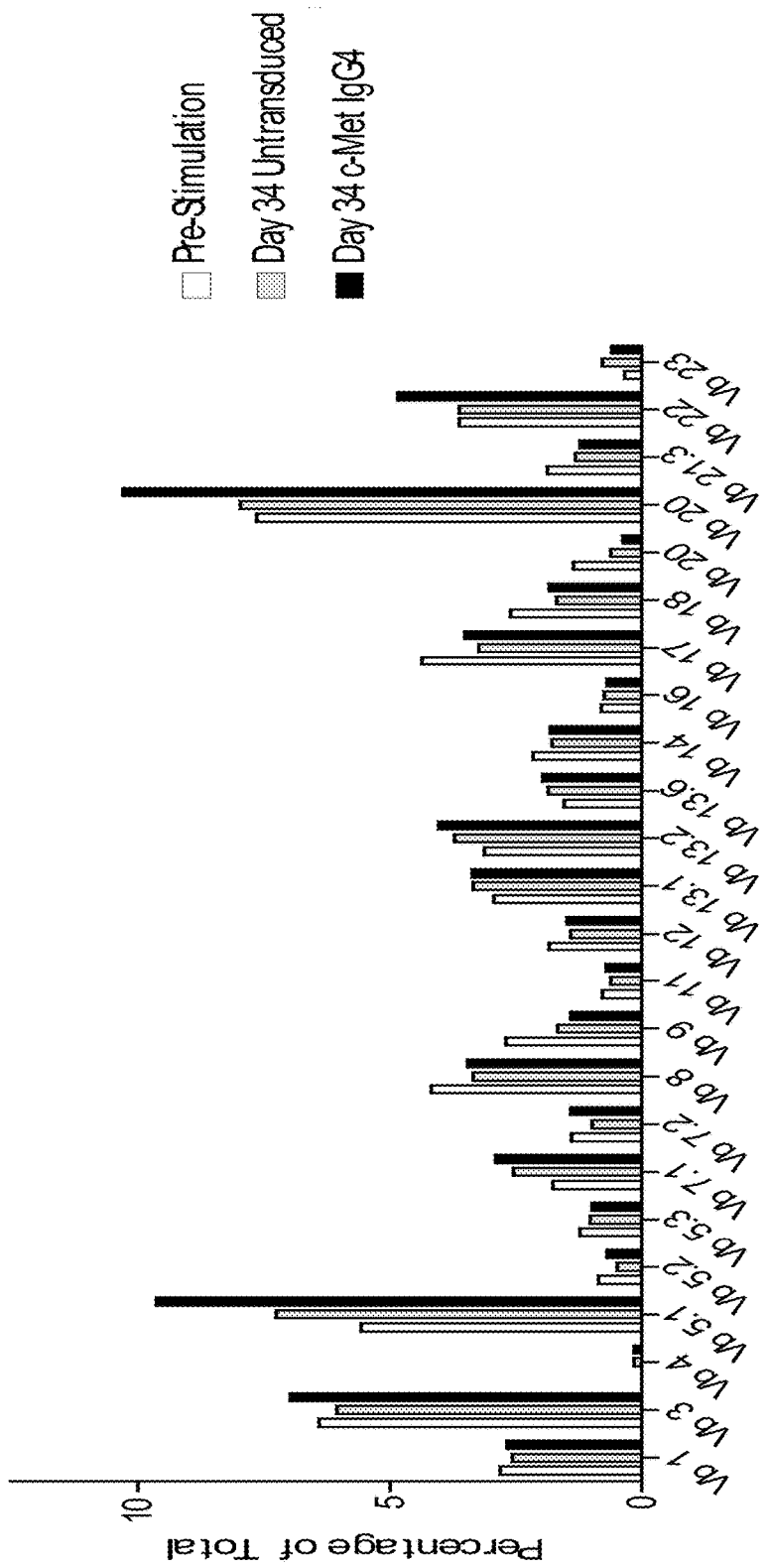
FIG. 11 is an image demonstrating that CAR T cells with a constitutive growth phenotype retain a diverse TCR Vβ repertoire. Human CD4 T cells were isolated, stimulated with anti-CD3/CD28, transduced with c-Met IgG4 CAR, and maintained in culture without exogenous cytokines as described. Donor matched mock transduced cells were stimulated and expanded simultaneously as control, however these cultures required additional stimulations to maintain in culture. Cells were cryopreserved at days 0, 13 and 34 after which they were simultaneously thawed and TCR Vβ analysis was performed using the IOTest Beta Mark TCR V kit.

Both continuous and classic CARs migrated at the predicted size as determined by Western blots probed with an anti-CD3ζ antibody. The CARs encoding the longer IgG4 hinge migrated more slowly than the CARs encoding CD8α hinges (FIG. 10). Under non-reducing conditions, these CARs exist as homodimers and monomers. The continuous cytokine-independent polyclonal CD4+ T cell proliferation mediated by the CD28:CD3ζ CARs was independent of the specificity of the endogenous TCR, and was not the result of clonal outgrowth because the T cell populations remained diverse during culture (FIG. 11). Finally the above results were reproducible on T cells obtained from at least 10 different healthy donors.

Constitutive Expression of IL-2 and a Diverse Array of Cytokines and Chemokines

Figure 3A:
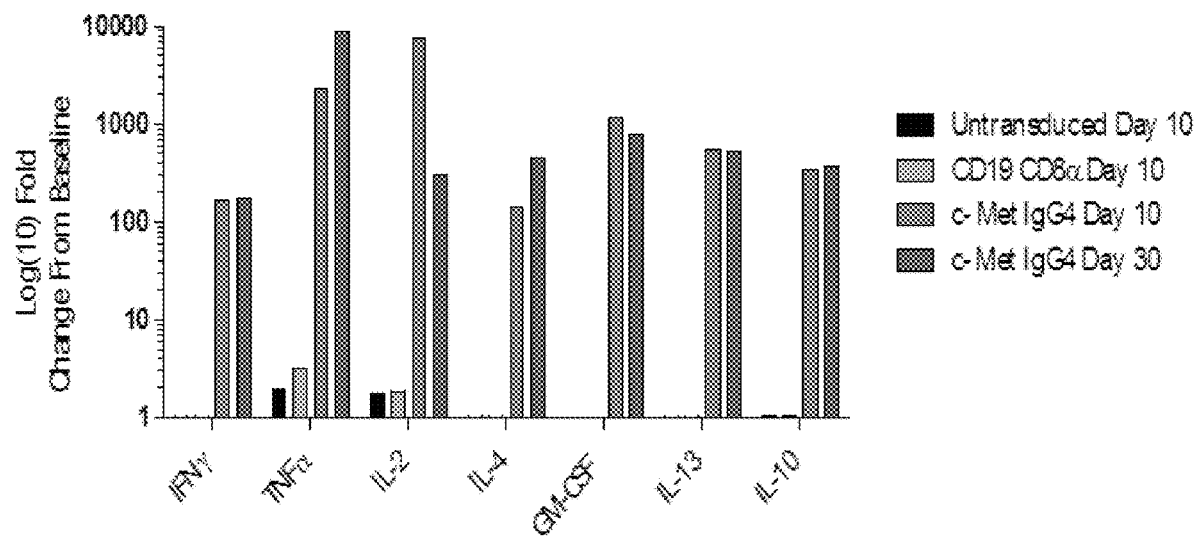
FIGS. 3A-3B are a series of images demonstrating that CAR T cells with continuous T cell proliferation have constitutive cytokine secretion.
Figure 3B:
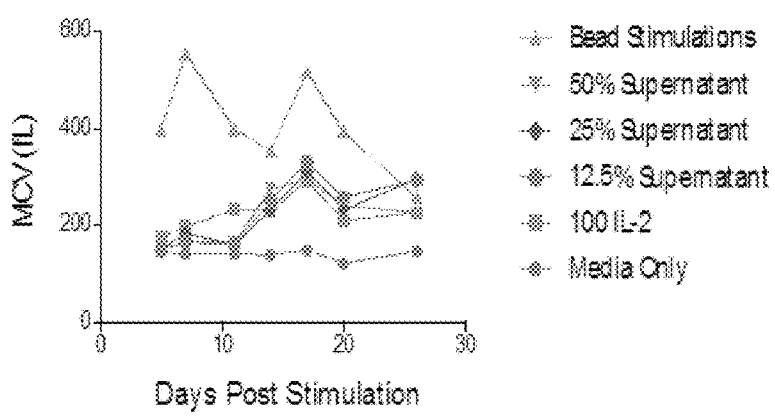
Figure 4A:
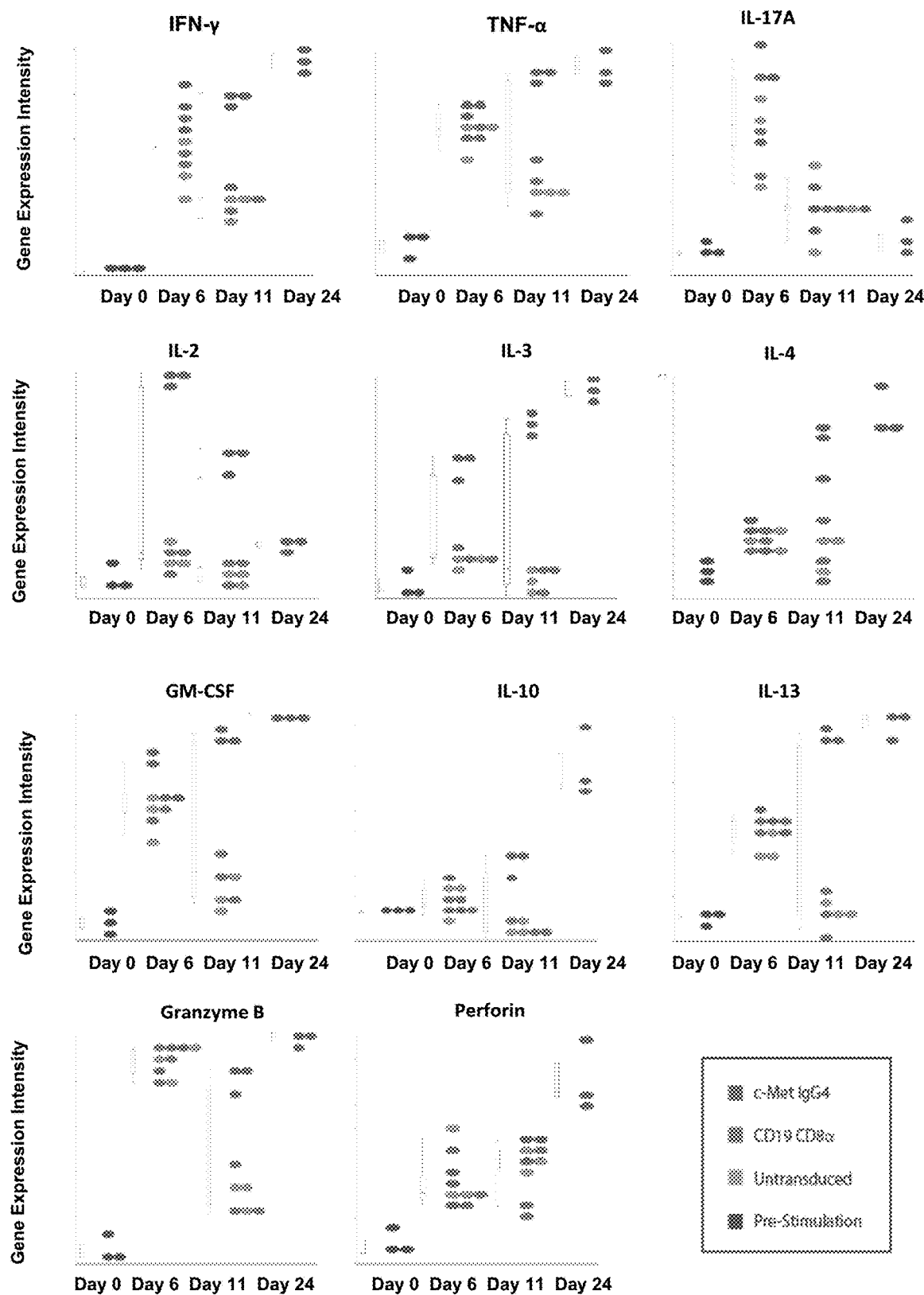
FIGS. 4A-4B are a series of images demonstrating that CARs with a constitutive growth phenotype display a unique gene signature.
Figure 5A:
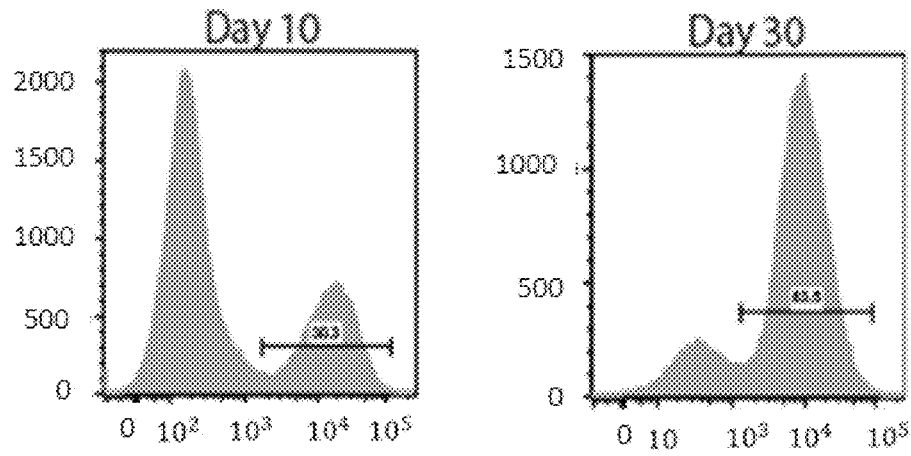
FIGS. 5A-5B are a series of images demonstrating that constitutive activation of AKT, NF-kB and MAPK signaling pathways is associated with the CAR T cell proliferative phenotype.

Without wishing to be bound by any particular theory, it is believed that the observation of CARs being able to mediate long term constitutive proliferation of primary T cells has not previously been reported. To begin to understand the mechanism of this phenomenon, experiments were designed to determine the levels of various cytokines and other immune-related factors in the supernatants from the cultures that might be sustaining their unusual longevity in culture. Analysis at the protein level revealed that the culture supernatants from continuous CARs contained high levels of cytokines characteristic of both Th1 and Th2 CD4+ T cells (FIG. 3A). In contrast, the cultures of classic CAR T cells had low levels of cytokines that decreased with time of culture. The differences were large in magnitude, as the cytokine concentrations in the cultures of continuous CARs were 100 to >1000-fold higher than the concentrations in the classic CAR cultures. The cytokines likely contributed to the proliferation because transfer of day 56 conditioned medium from continuous CAR T cell cultures induced activation of unstimulated naïve CD4+ T cells (FIG. 3B). These results were confirmed at the transcriptional level, with prominent expression of transcripts for IFN-γ, TNF-α, IL-2, IL-4, IL-13, IL-3 and GM-CSF in the cells isolated from the constitutively proliferating CAR T cells compared to the classic CAR T cells (FIG. 4A). Consistent with this finding, it was observed that continuous CAR T cells outgrew normal T cells in cultures that were initially comprised of mixtures of CAR T cells and T cells that did not express the CAR (FIG. 5A). In addition to the sustained transcription and secretion of cytokines and chemokines, the continuous CAR CD4+ T cells had elevated levels of granzyme B and perforin (FIG. 4A), consistent with the potent cytotoxic effector function that was observed (FIG. 8) and previously reported (Carpenito et al., 2009, Proc Natl Acad Sci USA 106:3360-3365).

Molecular Signature of Constitutive CAR T Cell Proliferation

Figure 4B:
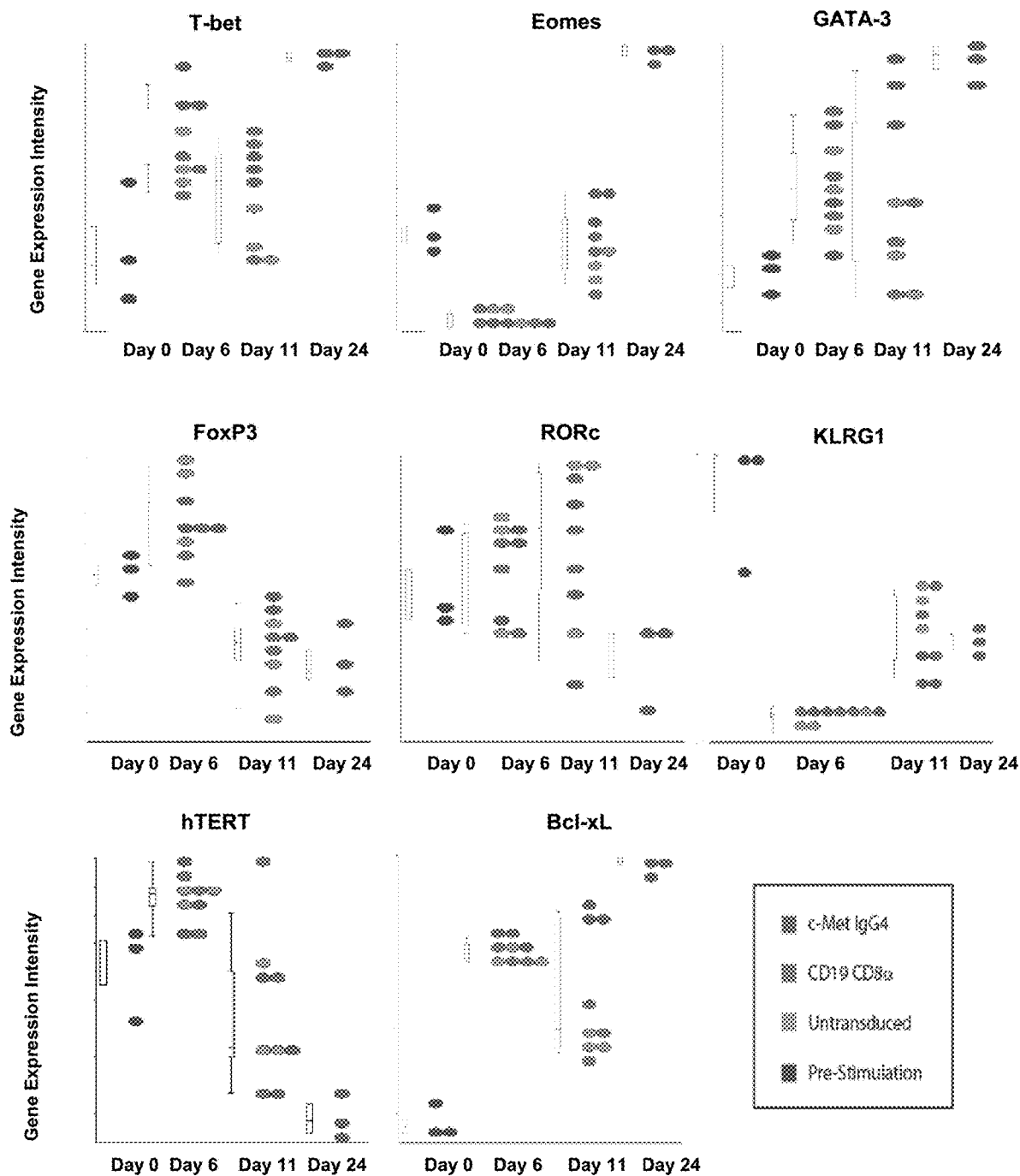

To further investigate the mechanism of the long term CAR T cell proliferation, experiments were designed to performed gene array analysis. The molecular signature of key transcription factors and genes involved in T cell polarization, growth and survival is shown in FIG. 4B. The master transcription factors T-bet (TBX21), Eomes, and GATA-3 were induced and maintained at high levels in the continuous CAR CD4+ T cells. In contrast, FoxP3 and RORC were expressed in continuous CAR T cells at comparable levels to untransduced activated T cells and T cells with the transient T cell proliferative phenotype. As early as day 11, Bcl-xL was highly expressed in the continuous CAR T cells compared to the classic CAR and other control T cell populations (p<0.001), suggesting that resistance to apoptosis as well as enhanced proliferation contributes to the long term proliferation of CAR T cells. Continuous CAR T cells also maintained low level expression of KLRG1, a gene often expressed in terminally differentiated and senescent CD4+ T cells (Voehringer et al., 2002, Blood 100:3698-3702), further emphasizing their proliferative capacity.

Figure 6A:
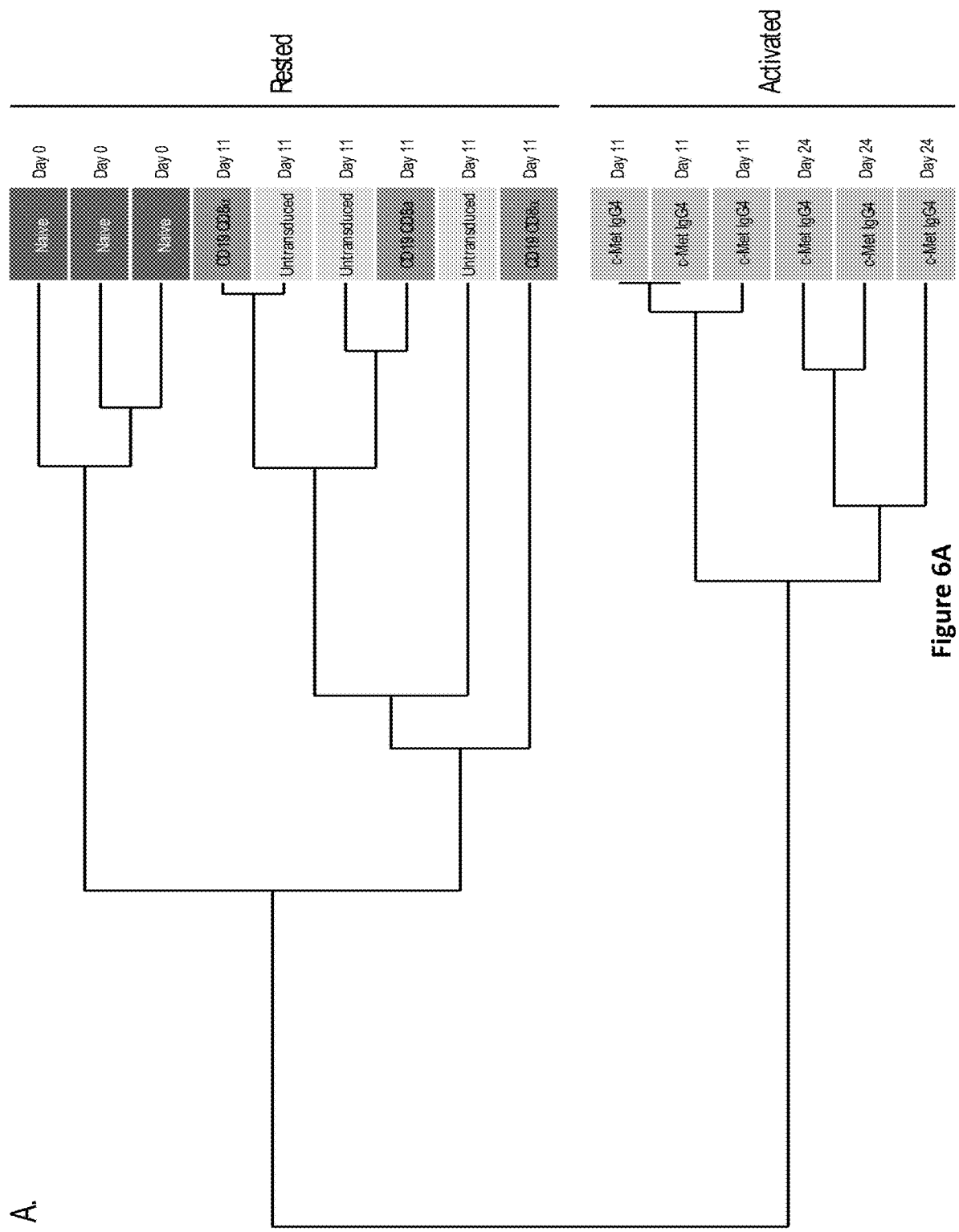

Hierarchical clustering analysis of the microarray data set indicates that the CAR T cells with constitutive T cell proliferation have a unique molecular signature (FIG. 6). It is notable that by day 11, cMet IgG4 CAR T cells with the long term growth phenotype closely cluster in the dendrogram. In contrast, naïve T cells were most closely related to untransduced T cells and classic CARs with un-sustained growth phenotypes on day 11 of culture (FIG. 6A). Similarly, fully activated day 6 T cells from all groups cluster together, while T cells expressing the continuous CAR constructs diverge by day 11 to display a unique RNA signature that differs from the genes expressed in untransduced or classic CAR T cells on day 6 (FIG. 6B).

Figure 6C:
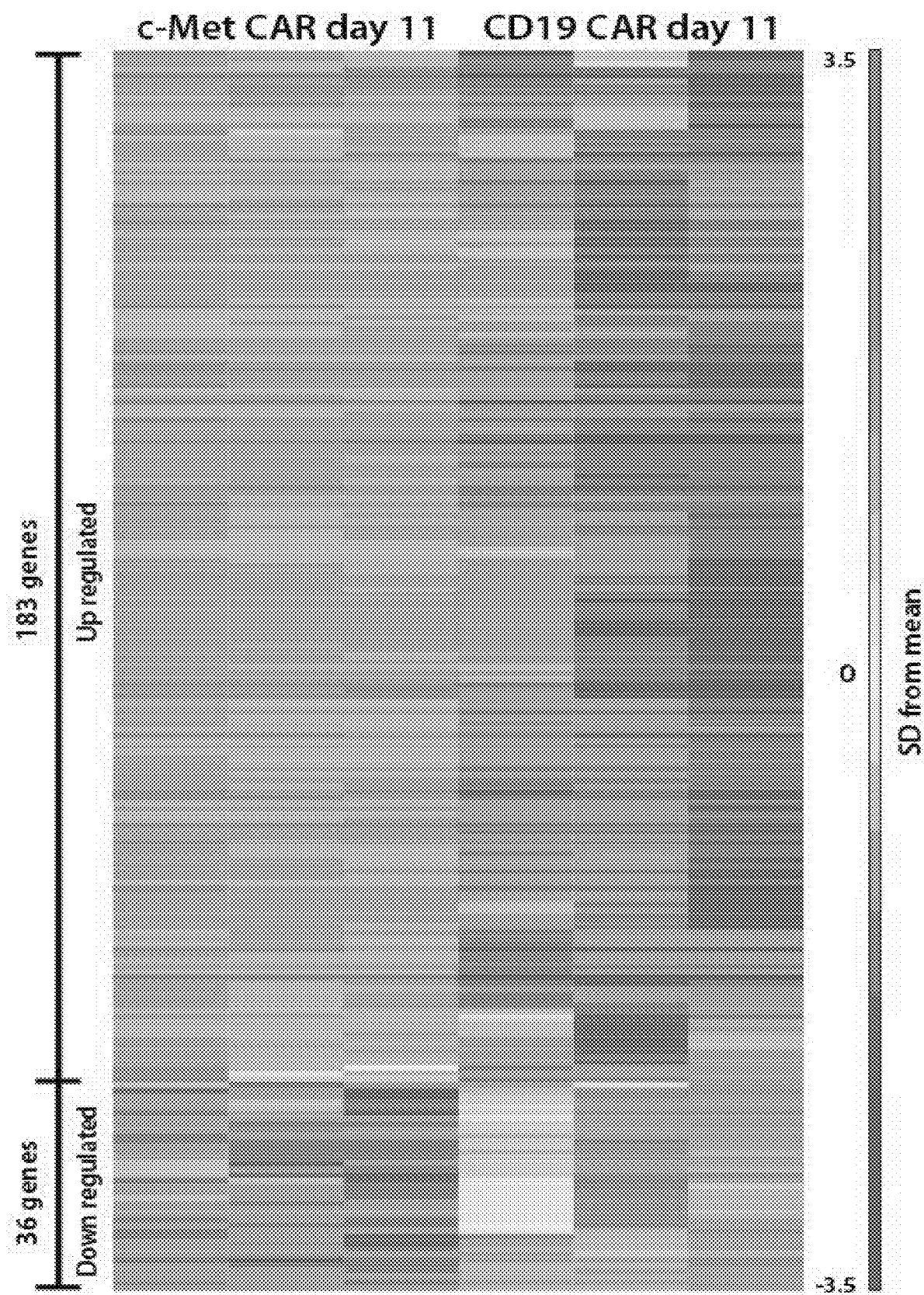

The differentially expressed genes in the continuous CAR (c-Met IgG4) and classic CAR (CD19 CD8α) T cells were plotted as a heat map to depict the relationship of the two populations (FIG. 6C). When analyzed using a stringent 5-fold cutoff on day 11 of culture, 183 genes were upregulated and 36 genes were down regulated in continuous CARs compared to the classic CAR T cells. Most notably the continuous CAR T cells are enriched for genes related to control of the cell cycle and a diverse group of cytokines.

Constitutive Induction of Signal Transduction by Continuous CARs

Figure 5B:
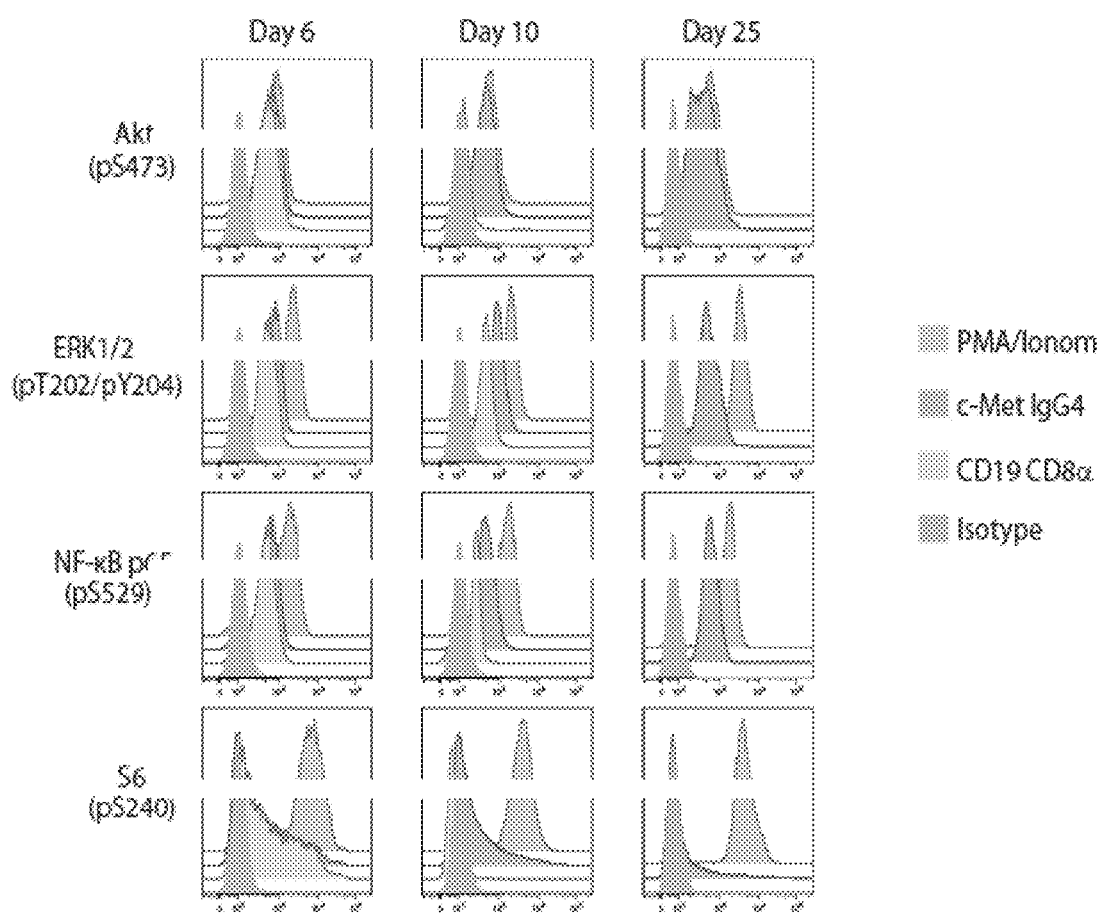

To further investigate the mechanisms of the continuous CAR dependent and ligand-independent T cell growth, experiments were designed to interrogate the canonical signal transduction pathways that are implicated in T cell activation and growth (FIG. 5B). T cells expressing classic or continuous CARs had similar levels of phosphorylation on Akt, ERK1/2, NF-κB p65 (RelA) and S6 on day 6 of culture. In contrast, only the continuous CAR T cells had sustained activation of Akt pS473, ERK1/2 pT202 and pY204, and RelA pS529 at days 10 and 25 of culture. However, the expression of continuous CARs in cells had only a minor effect on S6 pS240 phosphorylation, indicating that the CARs do not lead to universal activation of T cell signaling pathways. The constitutive signal transduction together with the above results demonstrating sustained cytokine secretion suggest that both cell intrinsic and extrinsic effects of the CAR can lead to the long term expansion of primary human T cells.

In the above experiments, primary human T cells were subjected to a single round of activation with anti-CD3 and CD28 beads, and then followed in culture without the addition of exogenous cytokines. This method of culture was chosen because it has been used in clinical trials, and the initial activation is necessary to mediate high efficiency CAR expression. To determine if the initial activation of the T cells by anti-CD3 and anti-CD28 signaling is required for the subsequent constitutive signaling by the CARs, we expressed the various CARs in a Jurkat T cell line that stably expresses GFP under the control of the NFAT promoter (FIG. 12). The cells were analyzed 3 days after transduction, and only the continuous CARs as classified by the growth phenotype in primary T cells, led to constitutive NFAT activation in Jurkat cells. This effect was cell intrinsic as only the Jurkat cells that expressed CARs on the surface had GFP expression. In contrast, expression of classic CARs (SS1 CAR with a truncated cytosolic domain and the CD19 CARs) did not lead to constitutive NFAT activation in Jurkat cells.

Figure 7A:
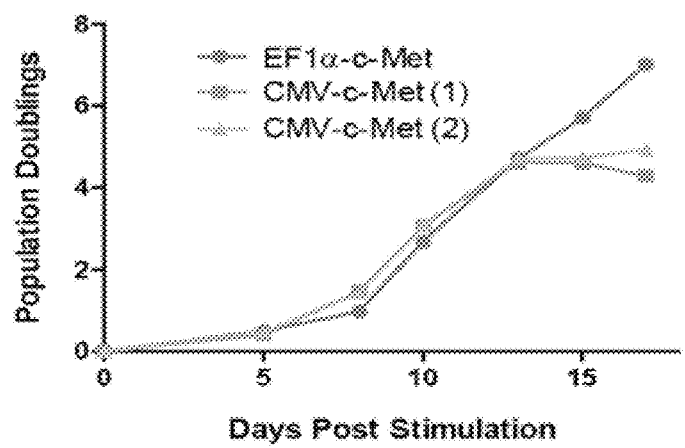
FIGS. 7A-7C are a series of images demonstrating that transgene expression levels are sufficient to convey the constitutive CAR growth phenotype. In vitro proliferation of human CD4+ T cells following 5 days of anti-CD3 plus CD28 stimulation and lentiviral transduction with c-MET expressing CARs under the indicated promoter. CM V(1) and CMV(2) represent replications of lentiviral vector production in the same human donor.
Figure 7B:
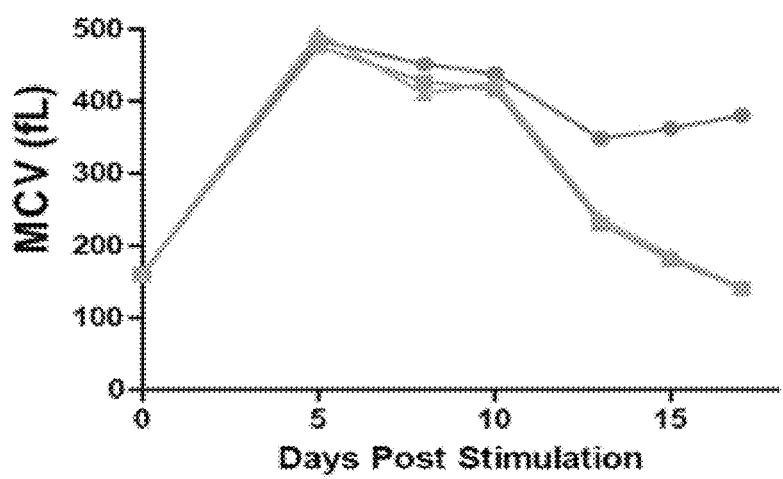
Figure 7C:
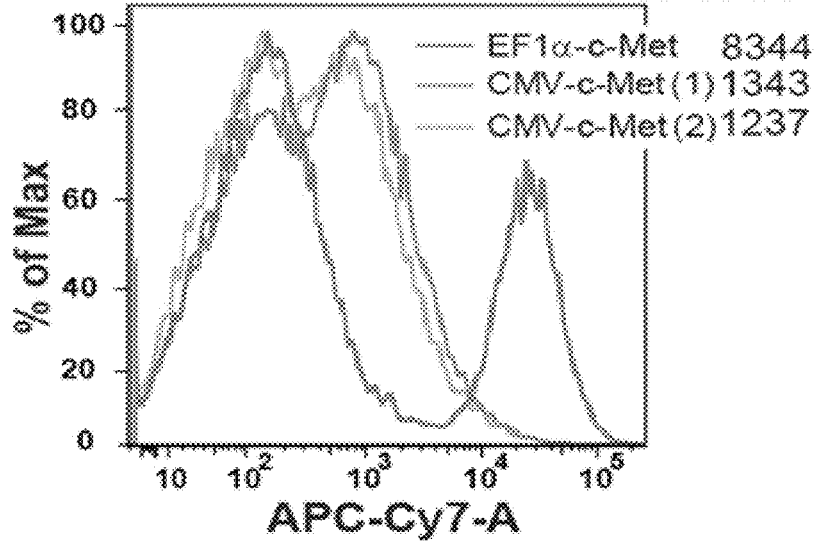

Level of Surface Expression Contributes to Classic or Continuous CAR T Cell Phenotype It has been shown that CARs expressed under the control of different eukaryotic promoters in primary T cells had widely varying levels of surface expression (Milone et al., 2009, Mol Ther 17:1453-1464). To determine if the level of surface expression contributed to the continuous CAR phenotype, CARs were expressed using the EF-1α or CMV promoter, resulting in a higher or lower expression (FIG. 7A). The c-Met CAR displayed a continuous phenotype when under the control of EF-1α (FIGS. 7B and 7C). In contrast, the same CAR reverted to a classic CAR phenotype when expressed under the control of the CMV promoter, resulting in approximately a 5-fold reduction in surface expression. However, without wishing to be bound by any particular theory, it is believed that bright surface expression may not be sufficient for the continuous CAR phenotype. Thus high levels of expression at the cell surface may be necessary but are not sufficient for a continuous CAR phenotype.

Figure 13:
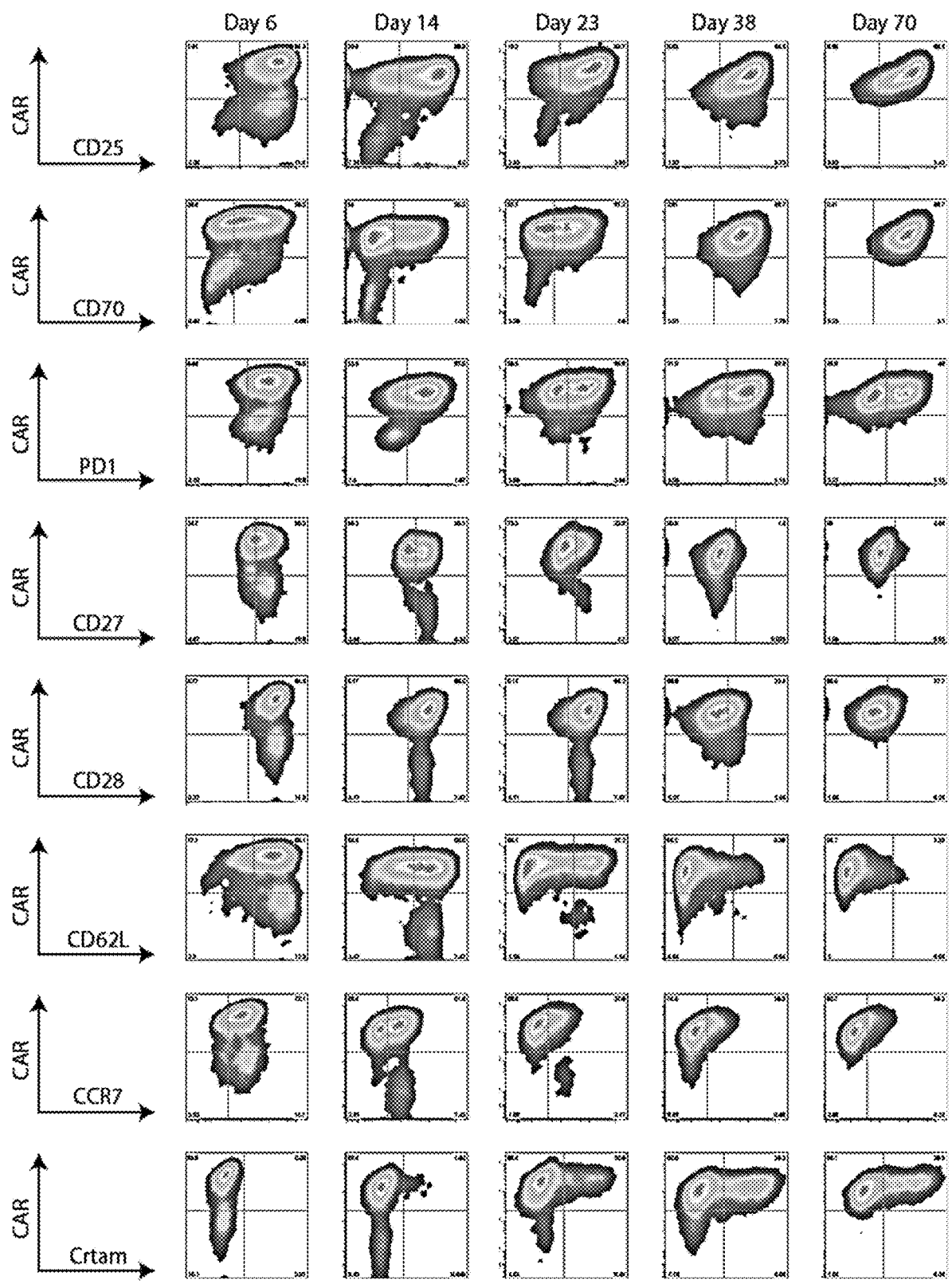
FIG. 13 is an image demonstrating that constitutive CAR T cell proliferation results in differentiation and evolution of a distinct cell surface phenotype. CD4 T cells were stimulated and transduced with the c-Met IgG4 CAR construct as previously described. Pre-stimulation cells were cryopreserved for later analysis. Cell samples were isolated at day 6, 14, 23, 38 and 70 and cryopreserved. Cells were thawed simultaneously and allowed to rest overnight without addition of cytokines. Cells were stained for CAR as well as CD25, CD70, PD-1, CD27, CD28, CD62L, CCR7 and Crtam.
Figure 14:
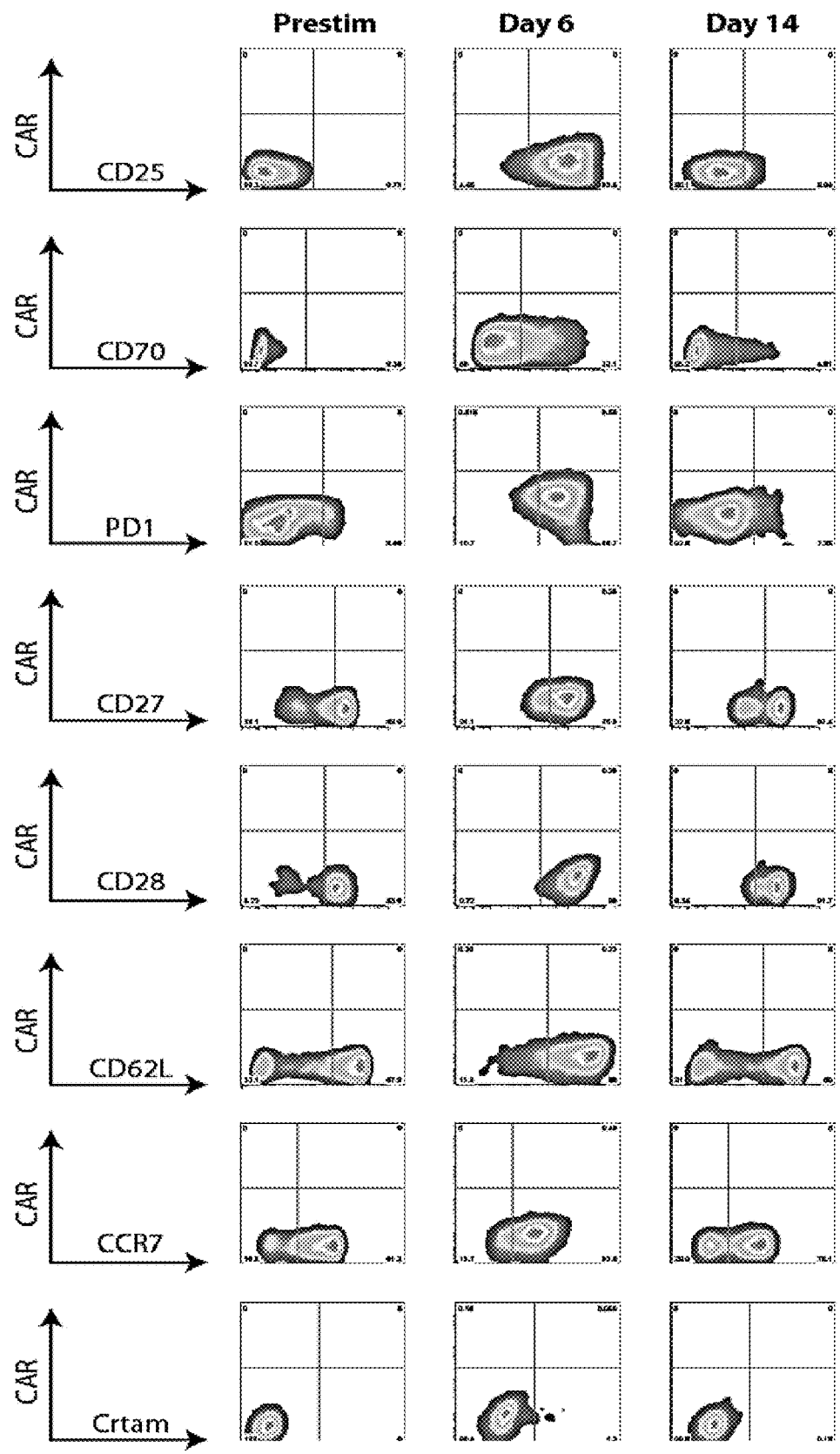
FIG. 14 is an image depicting effects of stimulation and cell culture on differentiation of non-transduced T cells.

Continuous CARs Induce T Cell Differentiation and Proliferation Without Transformation Polychromatic flow cytometry was used to further characterize the CAR T cells with constitutive proliferation. The expression of T cell molecules associated with activation and differentiation was examined on cultures of cells expressing or not expressing the CAR (FIG. 13). Additionally, untransduced T cells were followed over time after a single round of stimulation with anti-CD3 and CD28 beads (FIG. 14). The results show that a progressive enrichment for CAR T cells was observed, so that by day 23 of culture, essentially all cells expressed the CAR. This was associated with bright expression of CD25 at all times on the CART cells, whereas CD25 became undetectable by day 14 in the non-transduced companion control culture (FIG. 14). Similarly, CD70 was expressed at progressively higher frequencies in the CAR T cell culture, a feature not observed in the control culture. In contrast, CD27, the ligand for CD70, was expressed in the control cultures, while CD27 progressively decreased in the CAR T cell cultures. CD28, CD62L and CCR7 expression was maintained in the control cultures while many of the continuous CAR T cells became dim or negative for these molecules. In contrast, PD-1 was transiently expressed in the control cultures at day 6, while the CAR T cells had a prominent subpopulation of cells that retained expression of PD-1. Finally, Crtam, a molecule associated with cell polarity regulation (Yeh et al., 2008, Cell 132:846-859), was induced in the continuous CAR T cell cultures and expression of Crtam was notably restricted to the T cells expressing CARs at the surface.

The potential for the CAR T cells to transform was assessed by observation of long term cultures in vitro and by transfer of CART cells to immunodeficient mice. The long term cultured CAR T cells do not have constitutive expression of telomerase, as assessed by hTERT expression (FIG. 4B), and telomere length decreases with time in cultures of continuous CAR T cells (FIG. 15). In contrast, transformed human T cells have been reported to have constitutive telomerase activity (Hsu et al., 2007, Blood 109:5168-5177). To date, in more than 20 experiments, transformation has not been observed with T cells transduced with continuous CARs.

As a potentially more sensitive assay to detect the potential for transformation, NSG (NOD-SCID-γc−/−) mice were used, as previous studies have shown that adoptively transferred transformed and malignant T cells can form tumors in immunodeficient mice (Newrzela et al., 2011, Mol Med 17:1223-1232). Groups of mice were infused with fully activated T cells or with continuous CAR T cells and proliferation assessed by quantification of T cells in the mice and effector function assessed by the induction of xenogeneic graft versus host disease in the mice (FIG. 16). By day 60, xeno-reactivity (grade 1-3 xGVHD) was observed in 5/10 mice in the untransduced group compared to 3/10 in the c-Met IgG4 CAR group. Tumor formation was not observed at necropsy, and the levels of T cell engraftment were similar (p=0.39) in the mice engrafted with continuous CAR T cells or untransduced primary T cells that were stimulated with anti-CD3 and CD28.

Chimeric Antigen Receptors can Sustain Long Term T-Cell Proliferation Without Transformation The results presented herein relate to the unexpected finding that expression of some CARs containing CD28 and CD3ζ tandem signaling domains led to constitutive activation and proliferation of primary human T cells. It was observed that some CAR T cells exhibited constitutive secretion of large amounts of diverse cytokines and consequently do not require the addition of exogenous cytokine or feeder cells in order to maintain proliferation. This was surprising because in the numerous previous reports that described CARs endowed with CD28 domains (Krause et al, 1998, J Exp Med 188:619-626; Finney et al., 1998, Journal of Immunology 161:2791-2797; Geiger et al., 2001, Blood 98:2364-2371; Arakawa et al., 2002, Anticancer Research 4285-4289; Haynes et al., 2002, J Immunol 169(10):5780-6; Maher et al., 2002, Nature Biotechnology 20:70-75; Finney et al, 2004, J Immunol 172:104-113; Feldhaus et al., 1997, Gene Ther 4:833-838; Moeller et al., 2004, Cancer Gene Ther 11:371-379; Teng et al., 2004, Hum Gene Ther 15:699-708; Friedmann-Morvinski et al., 2005, Blood 105:3087-3093; Westwood et al., 2005, Proc Natl Acad Sci USA 102:19051-19056; Pule et al., 2005, Molecular Therapy 12:933-941; Willemsen et al., 2005, J Immunol 174:7853-7858; Loskog et al., 2006, Leukemia 20:1819-1828; Kowolik et al, 2006, Cancer Res 66:10995-11004; Shibaguchi et al., 2006, Anticancer Res 26:4067-4072; Teng et al., 2006, Human Gene Therapy 17:1134-1143; Brentjens et al., 2007, Clin Cancer Res 13:5426-5435; Alvarez-Vallina et al., 1996, Eur J Immunol 26:2304-2309; Gyobu et al., 2004, Cancer Res 64:1490-1495), the proliferation of such tandem CARs has been ligand dependent, and required restimulation of the CAR T cells in order to maintain proliferation. Here, the results show that one mechanism that can result in the phenotype of CARs with continuous T cell proliferation is the density of the CAR at the cell surface.

It is believed that this is the first description of "continuous CARs", i.e. primary T cells that exhibit prolonged exponential expansion in culture that is ligand independent and independent of the addition of exogenous cytokines or feeder cells. The constitutive secretion of large amounts of cytokines for several months by non-transformed T cells was unexpected. The continuous CAR T cells progressively differentiate during culture towards terminal effector cells and transformation has not been observed. The mechanism of the growth phenotype involves continuous ligand-independent signal transduction involving canonical TCR and CD28 signal transduction pathways. One mechanism identified that leads to continuous CAR T cells is the level of scFv surface expression, as CARs expressed brightly at the cell surface had sustained proliferation, while CARs expressed at lower levels did not exhibit sustained proliferation and cytokine secretion.

These results are notable for several reasons. The nature of the scFv has a role in the phenotype, as we have observed the continuous CAR phenotype with scFvs that are specific for c-Met and mesothelin but not in the case of FMC63 that is specific for CD19. An implication of this finding is that one cannot assume that the behavior of a signaling domain coupled to a given scFv will be the same when expressed with a distinct scFv. The method of CAR expression also has an unexpected contribution to the growth phenotype. To date, constitutive growth of T cells when the CARs are expressed by electroporation of mRNA or plasmids encoding Sleeping Beauty transposons have not observed (Zhao et al., 2010, Cancer Res 70:9062-9072; Huang et al., 2006, Blood 107:483-491; Singh et al., 2008, Cancer Research 68:2961-2971). When expressed using lentiviral vectors, continuous growth in vectors that employ the EF-1α promoter have only been observed. In previous studies comparing several promoters in lentiviral vectors, it was found that this promoter resulted in more stable and higher level expression in primary CD4 and CD8 T cells (Milone et al., 2009, Mol Ther 17:1453-1464). The particular design of the hinge and extracellular domain does not appear to have a major contribution to the continuous growth phenotype as this phenomenon with CARs that encode either the longer IgG4 hinge or the shorter CD8α scaffold have been observed. High level expression of the CAR appears to be necessary for the continuous growth phenotype.

It is believed that this is the first report of constitutive expression of the endogenous IL-2 gene in primary non-transformed T cells. Previous studies have shown that constitutive expression of IL-2 and CD25 occurs under conditions that lead to transformation of T cells, most prominently in HTLV-1 infection (McGuire et al, 1993, J Virol 67(3):1590-1599). It is likely that sustained signaling of the CD28 cytosolic domain encoded by the CAR is responsible for the constitutive secretion of IL-2 and numerous other cytokines. It is interesting that both HTLV-1 mediated expression of IL-2 by tax and IL-2 secretion driven by the endogenous CD28 pathway have been reported to be resistant to cyclosporine (Good et al., 1997, J Biol Chem 272(3):1425-1428; June et al., 1987, Mol Cell Biol 7(12):4472-4481), an immunosuppressant that inhibits the calcineurin phosphatase.

The results presented herein suggest that overexpression of the CD28 transmembrane and cytosolic domains in the context of some CARs can lead to constitutive signaling. Thus, it is likely that the regulation of endogenous CD28 gene expression is a critical determinant of T cell homeostasis, consistent with studies showing that overexpression of CD28 ligands leads to T cell hyperplasia in mice (Yu et al., 2000, J Immunol 164:3543-3553).

It is poorly understood why human T cells progressively downregulate CD28 expression with age and cell division (Goronzy et al., 2012, Semin Immunol 24(5):365-72). The constitutive CAR T cells maintained CAR expression at bright levels and had far more rapid downregulation of the endogenous CD28 molecule than classic CARs or non-transduced T cells. A dileucine motif in CD28 contributes to limiting expression of CARs on mouse T cells, and mutating this sequence leads to increased expression of the CAR (Nguyen et al., 2003, Blood 102(13):4320-5). The constitutive CAR T cells that have been tested employed the wild type dileucine motif in the CD28 endodomain.

The data presented herein indicates that given a permissive scFv, a 5-fold change in the level of expression can lead to the continuous CAR phenotype. This may explain why other laboratories have not detected this phenomenon using other expression systems.

Previous studies have tested tumor infiltrating lymphocytes (TIL) that were transduced to constitutively express IL-2, and the IL-2 TIL did not have better efficacy than conventional TIL in patients with metastatic melanoma (Heemskerk et al., 2008, Human Gene Therapy 19:496-510). Similarly, constitutive expression of IL-15 in human CD8 T cells led to the clonal outgrowth in the absence of exogenous cytokine after retroviral transduction with the IL-15 gene (Hsu et al., 2007, Blood 109:5168-5177).

The safety and clinical benefit with CD19 CARs that use the 4-1BB signaling domain have been reported (Porter et al., 2011, N Engl J Med 365:725-733; Kalos et al., 2011, Sci Transl Med 3:95ra73). T cells expressing this CAR have enhanced ligand-independent proliferation (Milone et al., 2009, Mol Ther 17:1453-1464) but do not have the long term continuous growth phenotype that has been described herein. CARs containing CD28 signaling domains have now been tested with safety in several clinical trials (Savoldo et al., 2011, J Clin Invest 121:1822-1825; Brentjens et al., 2011, Blood 118:4817-4828; Kochenderfer et al., 2010, Blood 116:4099-4102; Till et al., 2012, Blood 119:3940-3950; Kochenderfer et al., 2012, Blood 119:2709-2720). However it is important to note that those trials expressed the CARs after manufacturing with a different cell culture system and with a retroviral vector rather than the lentiviral vector that were used in the present work. Experiments can be conducted to determine whether continuous CARs such as those reported here would be useful and safe the clinical setting.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method for eliciting constitutive proliferation of an engineered T cell, the method comprising transducing a T cell with a lentiviral vector comprising a first nucleic acid comprising a constitutive promoter and a nucleotide sequence encoding a chimeric antigen receptor (CAR) comprising an anti-c-Met antibody or fragment thereof, an IgG4 hinge domain, a CD28 transmembrane domain, a CD28 costimulatory signaling region, and a CD3 zeta signaling domain, wherein the constitutive promoter controls expression of the CAR and the constitutive promoter is not a cytomegalovirus (CMV) promoter, thereby obtaining an engineered T cell, wherein the CAR is expressed on the surface of the engineered T cell, and wherein the engineered T cell constitutively proliferates in the absence of exogenous growth factors, exogenous cytokines, feeder cells, or exogenous antigen for at least 10 days but not more than 90 days after the transducing.

2. A method for increasing proliferation or number of progeny of an engineered T cell, the method comprising transducing the T cell with a lentiviral vector comprising a nucleic acid comprising a constitutive promoter and a nucleotide sequence encoding a chimeric antigen receptor (CAR) comprising an anti-c-Met antibody or fragment thereof, an IgG4 hinge domain, a CD28 transmembrane domain, a CD28 costimulatory signaling region, and a CD3 zeta signaling domain, wherein the constitutive promoter controls expression of the CAR and the constitutive promoter is not a cytomegalovirus (CMV) promoter, and wherein the CAR is expressed on the surface of the T cell, thereby obtaining an engineered T cell, wherein the engineered T cell has at least increased proliferation compared to the proliferation of an untransfected T cell or increased number of progeny compared to the number of progeny from the untransfected T cell.

3. A method for increasing mean cell volume (MCV) of a first engineered T cell, the method comprising transducing a first T cell with a first lentiviral vector comprising a first nucleic acid comprising a constitutive promoter and a nucleotide sequence encoding a continuous chimeric antigen receptor (CAR) comprising an anti-c-Met antibody or fragment thereof, an IgG4 hinge domain, a CD28 transmembrane domain, a CD28 costimulatory signaling region, and a CD3 zeta signaling domain, wherein the constitutive promoter of the first nucleic acid controls expression of the CAR and the constitutive promoter is not a cytomegalovirus (CMV) promoter, thereby obtaining a first engineered T cell, wherein the CAR is expressed on the surface of the first engineered T cell, and wherein the engineered T cell has increased mean cell volume (MCV) at 20 days after the transducing compared to the MCV of a second engineered T cell obtained at 20 days after transducing a second T cell with a second lentiviral vector comprising a second nucleic acid comprising the constitutive promoter and SEQ ID NO: 3, wherein the constitutive promoter of the second nucleic acid controls expression of SEQ ID NO: 3.

4. A method of producing an engineered T cell, the method comprising transducing the T cell with a lentiviral vector comprising a nucleic acid comprising a constitutive promoter and a nucleotide sequence encoding a chimeric antigen receptor (CAR) comprising an anti-c-Met antibody or fragment thereof, an IgG4 hinge domain, a CD28 transmembrane domain, a CD28 costimulatory signaling region, and a CD3 zeta signaling domain, wherein the constitutive promoter controls expression of the CAR and the constitutive promoter is not a cytomegalovirus (CMV) promoter, thereby obtaining the engineered T cell, wherein the CAR is expressed on the surface of the engineered T cell, and wherein the engineered T cell activates independent of exogenous antigen.

5. The method of any one of claims 2 and 3, wherein the increased proliferation, the increased number of progenitor cells, or the increased MCV occurs in absence of an exogenous cytokine,. an exogenous growth factor, exogenous antigen, or feeder cells.

6. A method for treating a subject with a cancer, the method comprising administering to the subject a first engineered T cell transduced with a first lentiviral vector comprising a first nucleic acid sequence comprising a constitutive promoter and a nucleotide sequence encoding a chimeric antigen receptor (CAR) comprising an anti-c-Met antibody or fragment thereof, an IgG4 hinge domain, a CD28 transmembrane domain, a CD28 costimulatory signaling region, and a CD3 zeta signaling domain, wherein the constitutive promoter of the first nucleic acid controls expression of the CAR and the constitutive promoter is not a cytomegalovirus (CMV) promoter, thereby obtaining the first engineered T cell, wherein the CAR is expressed on the surface of the first engineered T cell, and wherein the first engineered T cell has at least one of:
1) constitutive proliferation in the absence of exogenous growth factors, exogenous cytokines, feeder cells, or exogenous antigen for at least 10 days but not more than 90 days after the transducing;
2) increased proliferation compared to the proliferation of an untransfected T cell;
3) increased number of progeny compared to the number of progeny from the untransfected T cell;

4) increased mean cell volume (MCV) at 20 days after the transducing compared to the MCV of a second engineered T cell obtained at 20 days after transducing a second T cell with a second lentiviral vector comprising a second nucleic acid comprising the constitutive promoter and SEQ ID NO: 3, wherein the constitutive promoter of the second nucleic acid controls expression of SEQ ID NO: 3; and 5) activation independent of exogenous antigen.

7. The method of claim 6, wherein the cancer is selected from the group consisting of triple negative breast cancer and non-small cell lung cancer.

8. The method of any one of claims 1-4, wherein the CAR comprises an amino acid sequence encoded by the nucleic acid sequence of SEQ ID NO: 1.

9. The method of any one of claims 1 2 and 4, wherein the engineered T cell exhibits a cytokine signature comprising at least one cytokine selected from the group consisting of IFN-γ, TNF-α, IL-17A, IL-2, IL-3, IL-4, GM-CSF, IL-10, IL-13, Granzyme B, Perforin, and any combination thereof.

10. The method of any one of claims 1 2 and 4, wherein the engineered T cell exhibits an anti-tumor immunity when the anti-c-Met antibody or fragment thereof binds c-Met.

11. The method of claim 10, wherein the anti-c-Met antibody or fragment thereof is a single chain variable fragment (scFv).

12. The method of claim 4, wherein the activation independent of exogenous antigen occurs in absence of an exogenous cytokine, an exogenous growth factor, or feeder cells.

13. The method of 3, wherein the first engineered T cell exhibits a cytokine signature comprising at least one cytokine selected from the group consisting of IFN-γ, TNF-α, IL-17A, IL-2, IL-3, IL-4, GM-CSF, IL-10, IL-13, Granzyme B, Perforin, and any combination thereof.

14. The method of 3, wherein the first engineered T cell exhibits an anti-tumor immunity when the anti-c-Met antibody or fragment thereof binds c-Met.

* * * * *

UNITED STATES PATENT AND TRADEMARK OFFICE
CERTIFICATE OF CORRECTION

PATENT NO. : 10,800,840 B2
APPLICATION NO. : 16/014804
DATED : October 13, 2020
INVENTOR(S) : Matthew J. Frigault et al.

Page 1 of 1

It is certified that error appears in the above-identified patent and that said Letters Patent is hereby corrected as shown below:

In the Specification

On Column 1, Line 22, "STATEMENT REGARDING FEDERALLY SPONSORED RESEARCH OR DEVELOPMENT" please replace the existing paragraph with the following:
-- STATEMENT REGARDING FEDERALLY SPONSORED RESEARCH OR DEVELOPMENT
This invention was made with government support under grant number CA120409 awarded by the National Institutes of Health. The government has certain rights in the invention. --

Signed and Sealed this
Thirtieth Day of November, 2021

Drew Hirshfeld
*Performing the Functions and Duties of the*
*Under Secretary of Commerce for Intellectual Property and*
*Director of the United States Patent and Trademark Office*